(12) United States Patent
De Taboada et al.

(10) Patent No.: US 10,188,872 B2
(45) Date of Patent: *Jan. 29, 2019

(54) LIGHT-EMITTING DEVICE AND METHOD FOR PROVIDING PHOTOTHERAPY TO THE BRAIN

(75) Inventors: Luis De Taboada, Carlsbad, CA (US); Jackson Streeter, Reno, NV (US)

(73) Assignee: Pthera LLC, Newark, DE (US)

( * ) Notice: Subject to any disclaimer, the term of this patent is extended or adjusted under 35 U.S.C. 154(b) by 1171 days.

This patent is subject to a terminal disclaimer.

(21) Appl. No.: 12/496,571

(22) Filed: Jul. 1, 2009

(65) Prior Publication Data
US 2010/0016841 A1 Jan. 21, 2010

Related U.S. Application Data

(63) Continuation of application No. 11/385,988, filed on Mar. 21, 2006, now Pat. No. 7,575,589.
(Continued)

(51) Int. Cl.
*A61N 5/06* (2006.01)
*A61B 18/00* (2006.01)
(Continued)

(52) U.S. Cl.
CPC ......... *A61N 5/0613* (2013.01); *A61N 5/0622* (2013.01); *A61B 2018/00005* (2013.01);
(Continued)

(58) Field of Classification Search
CPC .. A61N 5/0613; A61N 5/0618; A61N 5/0622; A61N 2005/0632;
(Continued)

(56) References Cited

U.S. PATENT DOCUMENTS

| 554,470 A | 2/1896 | Weatherwax |
|---|---|---|
| 653,731 A | 7/1900 | Cunningham |

(Continued)

FOREIGN PATENT DOCUMENTS

| DE | 2 133 975 | 1/1973 |
|---|---|---|
| DE | 320 0584 A1 | 7/1983 |

(Continued)

OTHER PUBLICATIONS

U.S. Appl. No. 10/448,262, filed May 29, 2003, Oron et al.
(Continued)

*Primary Examiner* — Ahmed Farah
(74) *Attorney, Agent, or Firm* — Fish & Richardson P.C.

(57) ABSTRACT

An apparatus is provided for irradiating at least a portion of a patient's brain with electromagnetic radiation to treat stroke, Parkinson's Disease, Alzheimer's Disease, or depression. The apparatus includes a source of the electromagnetic radiation. The apparatus further includes an output optical element including a rigid and substantially thermally conductive material and a surface configured to be in thermal communication with the patient's body. The apparatus further includes a cooler thermally coupled to the output optical element to remove heat from the output optical element. The apparatus further includes a heat sink thermally coupled to the cooler, wherein the heat sink is positioned so that the electromagnetic radiation from the source propagates through the heat sink and through the output optical element.

14 Claims, 54 Drawing Sheets

Related U.S. Application Data

(60) Provisional application No. 60/763,261, filed on Jan. 30, 2006.

(51) Int. Cl.

| | |
|---|---|
| A61B 18/22 | (2006.01) |
| A61N 5/00 | (2006.01) |
| A61N 5/067 | (2006.01) |
| A61B 90/00 | (2016.01) |

(52) U.S. Cl.
CPC . *A61B 2018/2244* (2013.01); *A61B 2090/065* (2016.02); *A61N 2005/007* (2013.01); *A61N 2005/067* (2013.01); *A61N 2005/0647* (2013.01); *A61N 2005/0659* (2013.01)

(58) Field of Classification Search
CPC .... A61N 2005/0643; A61N 2005/0645; A61N 2005/0647; A61N 2005/0659; A61B 2018/0005; A61B 2018/0047; A61B 2018/00089; A61B 2018/000315; A61B 2018/000321
USPC ........ 607/88–91, 93, 108–110; 606/3, 10–13
See application file for complete search history.

(56) References Cited

U.S. PATENT DOCUMENTS

| | | |
|---|---|---|
| 1,856,969 A | 5/1932 | Reiter et al. |
| 3,375,755 A | 4/1968 | Hunt et al. |
| 3,735,755 A | 5/1973 | Eggleton et al. |
| 3,810,367 A | 5/1974 | Peterson |
| 4,076,393 A | 2/1978 | Bates |
| 4,230,125 A | 10/1980 | Schneider |
| 4,315,514 A | 2/1982 | Drewes et al. |
| 4,343,301 A | 8/1982 | Indech |
| 4,432,368 A | 2/1984 | Russek |
| 4,535,784 A | 8/1985 | Rohlicek et al. |
| 4,537,198 A | 8/1985 | Corbett |
| 4,539,987 A | 9/1985 | Nath et al. |
| 4,630,273 A | 12/1986 | Inoue et al. |
| 4,633,872 A | 1/1987 | Chaffee et al. |
| 4,639,987 A | 2/1987 | Georgopoulos |
| 4,669,466 A | 6/1987 | L'Esperance |
| 4,671,285 A | 6/1987 | Walker |
| 4,686,986 A | 8/1987 | Fenyo et al. |
| 4,798,215 A | 1/1989 | Turner |
| 4,836,203 A | 6/1989 | Muller et al. |
| 4,846,196 A | 7/1989 | Wiksell et al. |
| 4,850,351 A | 7/1989 | Herman et al. |
| 4,930,504 A | 6/1990 | Diamantopoulos et al. |
| 4,951,482 A | 8/1990 | Gilbert |
| 4,951,653 A | 8/1990 | Fry et al. |
| 4,966,144 A | 10/1990 | Rochkind et al. |
| 4,998,930 A | 3/1991 | Lundahl |
| 5,029,581 A | 7/1991 | Kaga et al. |
| 5,037,374 A | 8/1991 | Carol |
| 5,047,006 A | 9/1991 | Brandston et al. |
| 5,054,470 A | 10/1991 | Fry et al. |
| 5,125,925 A | 6/1992 | Lundahl |
| 5,150,704 A | 9/1992 | Tatebayashi et al. |
| 5,259,380 A | 11/1993 | Mendes et al. |
| 5,265,598 A | 11/1993 | Searfoss et al. |
| 5,267,294 A | 11/1993 | Kuroda et al. |
| 5,282,797 A | 2/1994 | Chess |
| 5,344,434 A | 9/1994 | Talmore |
| 5,358,503 A | 10/1994 | Bertwell et al. |
| 5,368,555 A | 11/1994 | Sussman et al. |
| 5,401,270 A | 3/1995 | Muller et al. |
| 5,405,368 A | 4/1995 | Eckhouse |
| 5,441,495 A | 8/1995 | Liboff et al. |
| 5,445,146 A | 8/1995 | Bellinger |
| 5,445,608 A | 8/1995 | Chen et al. |
| 5,447,528 A | 9/1995 | Gerardo |
| 5,464,436 A | 11/1995 | Smith |
| 5,474,528 A | 12/1995 | Meserol |
| 5,501,655 A | 3/1996 | Roit et al. |
| 5,503,637 A | 4/1996 | Kyricos et al. |
| 5,511,563 A | 4/1996 | Diamond |
| 5,540,737 A | 7/1996 | Fenn |
| 5,562,719 A | 10/1996 | Lopez-Claros |
| 5,570,445 A * | 10/1996 | Chou et al. ............ 385/92 |
| 5,571,152 A | 11/1996 | Chen et al. |
| 5,580,550 A | 12/1996 | Gough et al. |
| 5,580,555 A | 12/1996 | Schwartz |
| 5,601,526 A | 2/1997 | Chapelon et al. |
| 5,616,140 A | 4/1997 | Prescott |
| 5,617,258 A | 4/1997 | Negus et al. |
| 5,621,091 A | 4/1997 | Kunkel et al. |
| 5,622,168 A | 4/1997 | Keusch et al. |
| 5,627,870 A | 5/1997 | Kopecky |
| 5,640,978 A | 6/1997 | Wong |
| 5,643,334 A | 7/1997 | Eckhouse et al. |
| 5,720,894 A | 2/1998 | Neev et al. |
| 5,728,090 A | 3/1998 | Martin et al. |
| 5,735,844 A | 4/1998 | Anderson et al. |
| 5,755,752 A | 5/1998 | Segal |
| 5,762,867 A | 6/1998 | D'Silva |
| 5,766,233 A | 6/1998 | Thiberg |
| 5,769,878 A | 6/1998 | Kamei |
| 5,800,479 A | 9/1998 | Thiberg |
| 5,817,008 A | 10/1998 | Rafert et al. |
| 5,824,024 A | 10/1998 | Dial |
| 5,830,208 A | 11/1998 | Muller |
| 5,842,477 A | 12/1998 | Naughton et al. |
| 5,843,073 A | 12/1998 | Sinofsky |
| 5,849,585 A | 12/1998 | Mather et al. |
| 5,871,521 A | 2/1999 | Kaneda et al. |
| 5,879,376 A | 3/1999 | Miller |
| 5,902,741 A | 5/1999 | Purchio et al. |
| 5,928,207 A | 7/1999 | Pisano et al. |
| 5,928,845 A | 7/1999 | Feumi-Jantou |
| 5,928,945 A | 7/1999 | Seliktar et al. |
| 5,951,596 A | 9/1999 | Bellinger |
| 5,954,762 A | 9/1999 | Di Mino et al. |
| 5,957,964 A | 9/1999 | Ceravolo |
| 5,958,761 A | 9/1999 | Yogev et al. |
| 5,983,141 A | 11/1999 | Sluijter et al. |
| 5,989,245 A | 11/1999 | Prescott |
| 5,993,442 A | 11/1999 | Omori |
| 6,013,096 A | 1/2000 | Tucek |
| 6,015,404 A | 1/2000 | Altshuler et al. |
| 6,027,495 A | 2/2000 | Miller |
| 6,030,767 A | 2/2000 | Wagner et al. |
| 6,033,431 A | 3/2000 | Segal |
| 6,042,531 A | 3/2000 | Holcomb |
| 6,045,575 A | 4/2000 | Rosen et al. |
| 6,046,046 A | 4/2000 | Hassanein |
| 6,059,820 A | 5/2000 | Baronov |
| 6,060,306 A | 5/2000 | Flatt et al. |
| 6,063,108 A | 5/2000 | Salansky et al. |
| 6,074,411 A | 6/2000 | Lai et al. |
| 6,084,242 A | 6/2000 | Brown et al. |
| 6,100,290 A | 8/2000 | Levy et al. |
| 6,107,325 A | 8/2000 | Chan et al. |
| 6,107,608 A | 8/2000 | Hayes |
| 6,112,110 A | 8/2000 | Wilk |
| 6,117,128 A | 9/2000 | Gregory |
| 6,129,748 A | 10/2000 | Kamei |
| 6,143,878 A | 11/2000 | Koopman et al. |
| 6,146,410 A | 11/2000 | Nagypal et al. |
| 6,149,679 A | 11/2000 | Di Mino et al. |
| 6,156,028 A | 12/2000 | Prescott |
| 6,162,211 A | 12/2000 | Tankovich et al. |
| 6,179,771 B1 | 1/2001 | Mueller |
| 6,179,830 B1 | 1/2001 | Kokubu |
| 6,187,210 B1 | 2/2001 | Lebouitz et al. |
| 6,198,958 B1 | 3/2001 | Ives et al. |
| 6,210,317 B1 | 4/2001 | Bonlie |
| 6,210,425 B1 | 4/2001 | Chen |
| 6,213,998 B1 | 4/2001 | Shen et al. |
| 6,214,035 B1 | 4/2001 | Streeter |
| 6,221,095 B1 | 4/2001 | Van Zuylen et al. |

(56) References Cited

U.S. PATENT DOCUMENTS

| | | | |
|---|---|---|---|
| 6,223,071 B1 | 4/2001 | Lundahl et al. | |
| 6,235,015 B1* | 5/2001 | Mead et al. | 606/9 |
| 6,238,425 B1 | 5/2001 | Thiberg | |
| 6,264,649 B1 | 7/2001 | Whitcroft et al. | |
| 6,267,779 B1 | 7/2001 | Gerdes | |
| 6,267,780 B1 | 7/2001 | Streeter | |
| 6,273,884 B1 | 8/2001 | Altshuler et al. | |
| 6,273,885 B1 | 8/2001 | Koop et al. | |
| 6,273,905 B1 | 8/2001 | Streeter | |
| 6,277,974 B1 | 8/2001 | Lo et al. | |
| 6,290,713 B1 | 9/2001 | Russell | |
| 6,290,714 B1 | 9/2001 | Streeter | |
| 6,306,130 B1* | 10/2001 | Anderson et al. | 606/27 |
| 6,312,451 B1 | 11/2001 | Streeter | |
| 6,344,050 B1 | 2/2002 | Chen | |
| 6,358,272 B1 | 3/2002 | Wilden | |
| 6,363,285 B1 | 3/2002 | Wey | |
| 6,364,907 B1 | 4/2002 | Obochi et al. | |
| 6,379,295 B1 | 4/2002 | Woo | |
| 6,379,376 B1 | 4/2002 | Lubart | |
| 6,391,023 B1 | 5/2002 | Weber et al. | |
| 6,395,016 B1 | 5/2002 | Oron et al. | |
| 6,397,107 B1 | 5/2002 | Lee et al. | |
| 6,402,678 B1 | 6/2002 | Fischell et al. | |
| 6,421,562 B1 | 7/2002 | Ross | |
| 6,432,101 B1 | 8/2002 | Weber et al. | |
| 6,436,094 B1 | 8/2002 | Reuter | |
| 6,440,121 B1 | 8/2002 | Weber et al. | |
| 6,443,974 B1 | 9/2002 | Oron et al. | |
| 6,443,977 B1 | 9/2002 | Jaillet | |
| 6,443,978 B1 | 9/2002 | Zharov | |
| 6,447,537 B1 | 9/2002 | Hartman | |
| 6,458,120 B1 | 10/2002 | Shen et al. | |
| 6,471,716 B1 | 10/2002 | Pecukonis | |
| 6,494,900 B1 | 12/2002 | Salansky et al. | |
| 6,508,813 B1 | 1/2003 | Altschuler | |
| 6,511,475 B1 | 1/2003 | Altschuler et al. | |
| 6,514,220 B2 | 2/2003 | Melton, Jr. et al. | |
| 6,530,920 B1 | 3/2003 | Whitcroft et al. | |
| 6,537,301 B1 | 3/2003 | Kamei | |
| 6,537,302 B1 | 3/2003 | Thiberg | |
| 6,537,304 B1 | 3/2003 | Oron | |
| 6,542,524 B2 | 4/2003 | Miyake | |
| 6,551,308 B1 | 4/2003 | Muller et al. | |
| 6,554,853 B2 | 4/2003 | Chen | |
| 6,571,735 B1 | 6/2003 | Wilkinson | |
| 6,602,245 B1 | 8/2003 | Thiberg | |
| 6,602,274 B1 | 8/2003 | Chen | |
| 6,602,275 B1 | 8/2003 | Sullivan | |
| 6,632,219 B1 | 10/2003 | Baronov et al. | |
| 6,638,272 B2 | 10/2003 | Cho et al. | |
| 6,653,618 B2 | 11/2003 | Zenzie | |
| 6,663,659 B2 | 12/2003 | McDaniel | |
| 6,666,878 B2 | 12/2003 | Carlgren | |
| 6,676,655 B2 | 1/2004 | McDaniel | |
| 6,679,877 B2 | 1/2004 | Ota et al. | |
| 6,685,702 B2 | 2/2004 | Quijano et al. | |
| 6,689,062 B1 | 2/2004 | Mesallum | |
| 6,692,486 B2 | 2/2004 | Jaafar et al. | |
| 6,692,517 B2 | 2/2004 | Cho et al. | |
| 6,733,492 B2 | 5/2004 | Ota et al. | |
| 6,743,222 B2 | 6/2004 | Durkin et al. | |
| 6,758,845 B1 | 7/2004 | Weekwerth et al. | |
| 6,770,069 B1 | 8/2004 | Hobart et al. | |
| 6,817,997 B2 | 11/2004 | Furuno et al. | |
| 6,832,111 B2 | 12/2004 | Tu et al. | |
| 6,860,896 B2 | 3/2005 | Leber et al. | |
| 6,866,678 B2 | 3/2005 | Shenderova et al. | |
| 6,872,221 B2 | 3/2005 | Lytle | |
| 6,878,144 B2 | 4/2005 | Altshuler et al. | |
| 6,899,723 B2 | 5/2005 | Chen | |
| 6,918,922 B2 | 7/2005 | Oron | |
| 6,921,413 B2 | 7/2005 | Mahadevan-Jansen et al. | |
| 6,974,224 B2 | 12/2005 | Thomas-Benedict | |
| 6,974,450 B2 | 12/2005 | Weber et al. | |
| 6,974,451 B2 | 12/2005 | Altshuler et al. | |
| 6,976,985 B2 | 12/2005 | Altshuler et al. | |
| 7,037,326 B2 | 5/2006 | Lee | |
| 7,041,094 B2 | 5/2006 | Connors et al. | |
| 7,051,738 B2 | 5/2006 | Oron et al. | |
| 7,066,929 B1 | 6/2006 | Azar et al. | |
| 7,070,611 B2 | 7/2006 | Biel | |
| 7,077,840 B2 | 7/2006 | Altshuler et al. | |
| 7,081,128 B2 | 7/2006 | Hart et al. | |
| 7,083,610 B1 | 8/2006 | Murray et al. | |
| 7,100,615 B1 | 9/2006 | Kert | |
| 7,101,384 B2 | 9/2006 | Benedict | |
| 7,118,563 B2 | 10/2006 | Weckwerth et al. | |
| 7,150,710 B2 | 12/2006 | Haber et al. | |
| 7,192,279 B2 | 3/2007 | Rogovsky | |
| 7,217,266 B2 | 5/2007 | Anderson et al. | |
| 7,220,254 B2 | 5/2007 | Altshuler et al. | |
| 7,282,060 B2 | 10/2007 | DeBenedictis et al. | |
| 7,288,108 B2 | 10/2007 | DiMauro et al. | |
| 7,303,578 B2 | 12/2007 | De Taboada et al. | |
| 7,311,722 B2 | 12/2007 | Larsen | |
| 7,311,723 B2 | 12/2007 | Seibel et al. | |
| 7,316,922 B2 | 1/2008 | Streeter | |
| 7,344,555 B2 | 3/2008 | Anders et al. | |
| 7,351,253 B2 | 4/2008 | DiMauro et al. | |
| 7,389,776 B2 | 6/2008 | Maksimovich | |
| 7,402,167 B2 | 7/2008 | Nemenov et al. | |
| 7,412,141 B2 | 8/2008 | Gowda et al. | |
| 7,463,916 B2 | 12/2008 | Kawasaki et al. | |
| 7,534,255 B1 | 5/2009 | Streeter et al. | |
| 7,559,945 B2 | 7/2009 | Breden et al. | |
| 7,575,589 B2* | 8/2009 | De Taboada et al. | 607/88 |
| 7,695,469 B2 | 4/2010 | Boutoussov et al. | |
| 7,695,504 B2 | 4/2010 | Anders et al. | |
| 7,703,458 B2* | 4/2010 | Levernier et al. | 128/898 |
| 7,744,590 B2 | 6/2010 | Eells et al. | |
| 7,848,035 B2 | 12/2010 | DeLapp et al. | |
| 8,025,687 B2 | 9/2011 | Streeter et al. | |
| 2001/0044623 A1 | 11/2001 | Chen | |
| 2002/0029071 A1 | 3/2002 | Whitehurst | |
| 2002/0058976 A1 | 5/2002 | Lee | |
| 2002/0068927 A1 | 6/2002 | Prescot | |
| 2002/0087205 A1 | 7/2002 | Chen | |
| 2002/0123781 A1 | 9/2002 | Shanks et al. | |
| 2002/0156371 A1 | 10/2002 | Hedlund et al. | |
| 2002/0161418 A1 | 10/2002 | Wilkens et al. | |
| 2002/0188334 A1 | 12/2002 | Carlgren | |
| 2002/0198575 A1 | 12/2002 | Sullivan | |
| 2003/0004556 A1 | 1/2003 | McDaniel | |
| 2003/0021124 A1 | 1/2003 | Elbrecht et al. | |
| 2003/0023283 A1 | 1/2003 | McDaniel | |
| 2003/0109906 A1 | 6/2003 | Streeter | |
| 2003/0114872 A1 | 6/2003 | Mueller et al. | |
| 2003/0125782 A1 | 7/2003 | Streeter | |
| 2003/0125783 A1 | 7/2003 | Moran | |
| 2003/0144712 A1 | 7/2003 | Streeter | |
| 2003/0167080 A1 | 9/2003 | Hart et al. | |
| 2003/0181962 A1 | 9/2003 | Streeter | |
| 2003/0212442 A1 | 11/2003 | Streeter | |
| 2003/0216797 A1 | 11/2003 | Oran | |
| 2004/0010300 A1 | 1/2004 | Masotti et al. | |
| 2004/0014199 A1 | 1/2004 | Streeter | |
| 2004/0015214 A1 | 1/2004 | Simkin et al. | |
| 2004/0030325 A1 | 2/2004 | Cahir et al. | |
| 2004/0044384 A1 | 3/2004 | Leber et al. | |
| 2004/0073278 A1 | 4/2004 | Pachys | |
| 2004/0093042 A1 | 5/2004 | Altshuler et al. | |
| 2004/0116909 A1 | 6/2004 | Neuberger et al. | |
| 2004/0132002 A1 | 7/2004 | Streeter | |
| 2004/0138727 A1 | 7/2004 | Taboada et al. | |
| 2004/0153130 A1 | 8/2004 | Oron et al. | |
| 2004/0153131 A1 | 8/2004 | Yorke | |
| 2004/0158300 A1 | 8/2004 | Gardiner | |
| 2004/0162596 A1 | 8/2004 | Altshuler et al. | |
| 2004/0167501 A1 | 8/2004 | Island et al. | |
| 2004/0220513 A1 | 11/2004 | Streeter | |
| 2004/0236226 A1 | 11/2004 | Maki et al. | |
| 2004/0260367 A1 | 12/2004 | Taboada et al. | |
| 2005/0005626 A1 | 1/2005 | McMahon | |

(56) References Cited

U.S. PATENT DOCUMENTS

| | | |
|---|---|---|
| 2005/0009161 A1 | 1/2005 | Streeter |
| 2005/0024853 A1 | 2/2005 | Thomas-Benedict |
| 2005/0216072 A1 | 3/2005 | Mahadevan-Jansen et al. |
| 2005/0107851 A1 | 5/2005 | Da Taboada et al. |
| 2005/0143792 A1 | 6/2005 | Jay |
| 2005/0159793 A1 | 7/2005 | Streeter |
| 2005/0187595 A1 | 8/2005 | Streeter |
| 2005/0203595 A1 | 9/2005 | Oron |
| 2006/0155348 A1 | 7/2006 | deCharms |
| 2006/0167532 A1 | 7/2006 | Parker |
| 2006/0200116 A1* | 9/2006 | Ferren et al. .............. 606/9 |
| 2006/0223155 A1 | 10/2006 | Streeter |
| 2006/0253177 A1 | 11/2006 | De Taboada et al. |
| 2007/0129778 A1 | 1/2007 | Dougal |
| 2007/0066996 A1 | 3/2007 | Katzman et al. |
| 2007/0100403 A1* | 5/2007 | Felice et al. .............. 607/96 |
| 2007/0114872 A1 | 5/2007 | Han |
| 2007/0142881 A1 | 6/2007 | Hennings |
| 2007/0159592 A1 | 7/2007 | Rylander et al. |
| 2007/0162093 A1 | 7/2007 | Porter et al. |
| 2007/0179570 A1 | 8/2007 | De Taboada et al. |
| 2007/0179571 A1 | 8/2007 | De Taboada |
| 2007/0198004 A1 | 8/2007 | Altshuler et al. |
| 2007/0219605 A1 | 9/2007 | Yaroslaysky et al. |
| 2007/0255359 A1 | 11/2007 | Neev |
| 2007/0260295 A1 | 11/2007 | Chen et al. |
| 2007/0288072 A1 | 12/2007 | Pascual-Leone et al. |
| 2008/0004565 A1 | 1/2008 | Streeter et al. |
| 2008/0033412 A1 | 2/2008 | Whelan et al. |
| 2008/0033513 A1 | 2/2008 | Man et al. |
| 2008/0051858 A1 | 2/2008 | Haber et al. |
| 2008/0077199 A1 | 2/2008 | Shefi et al. |
| 2008/0070229 A1 | 3/2008 | Streeter |
| 2008/0114419 A1 | 5/2008 | Crowley |
| 2008/0125836 A1 | 5/2008 | Streeter et al. |
| 2008/0140164 A1 | 6/2008 | Oberreiter et al. |
| 2008/0208297 A1 | 8/2008 | Gertner et al. |
| 2008/0221211 A1 | 9/2008 | Streeter |
| 2008/0287930 A1 | 11/2008 | Rapoport |
| 2009/0054955 A1 | 2/2009 | Kopell et al. |
| 2009/0088680 A1 | 4/2009 | Aravanis et al. |
| 2009/0112280 A1 | 4/2009 | Wingeier et al. |
| 2009/0163982 A1 | 6/2009 | deCharms |
| 2009/0216301 A1 | 8/2009 | Streeter et al. |
| 2009/0222067 A1 | 9/2009 | Toselli et al. |
| 2009/0254068 A1 | 10/2009 | Karni et al. |
| 2009/0254154 A1 | 10/2009 | De Taboada et al. |
| 2009/0270776 A1 | 10/2009 | Chang |
| 2010/0010592 A1 | 1/2010 | De Taboada et al. |
| 2010/0010594 A1 | 1/2010 | De Taboada |
| 2010/0016841 A1 | 1/2010 | De Taboada |
| 2010/0067128 A1 | 3/2010 | Delapp |
| 2010/0094384 A1 | 4/2010 | De Taboada |
| 2010/0105977 A1 | 4/2010 | DeTaboada et al. |
| 2010/0152820 A1 | 6/2010 | Anders et al. |
| 2010/0161017 A1 | 6/2010 | Choi et al. |
| 2010/0204762 A1 | 8/2010 | De Taboada et al. |
| 2010/0211136 A1 | 8/2010 | De Taboada et al. |
| 2010/0331928 A1 | 12/2010 | Dunning et al. |
| 2011/0060266 A1 | 3/2011 | Streeter |
| 2011/0102916 A1 | 5/2011 | DeLapp |
| 2011/0144723 A1 | 6/2011 | Streeter et al. |
| 2011/0245897 A1 | 10/2011 | Streeter |

FOREIGN PATENT DOCUMENTS

| | | |
|---|---|---|
| DE | 41 08 328 A1 | 9/1992 |
| DE | 42 13 053 A1 | 10/1993 |
| DE | 295 15 096 U1 | 1/1996 |
| EP | 0130950 A2 | 1/1985 |
| EP | 0 130 950 | 4/1990 |
| EP | 0 763 371 A2 | 3/1997 |
| EP | 0 783 904 A2 | 7/1997 |
| EP | 0 827 716 | 3/1998 |
| EP | 1 074 275 | 2/2001 |
| EP | 1101450 A1 | 5/2001 |
| EP | 1 226 787 A2 | 7/2002 |
| EP | 2 082 696 | 7/2009 |
| JP | 04023634 | 2/1992 |
| JP | 2000300684 A | 10/2000 |
| JP | 2001046527 A | 2/2001 |
| JP | 2002511323 A | 4/2002 |
| JP | 2004527362 A | 9/2004 |
| WO | WO 92/03964 | 3/1992 |
| WO | WO 96/36397 | 11/1996 |
| WO | WO 1996/36397 | 11/1996 |
| WO | WO 96/36396 | 1/1997 |
| WO | WO 98/04321 | 2/1998 |
| WO | WO 98/22573 | 5/1998 |
| WO | WO 98/33556 | 8/1998 |
| WO | WO 9916369 A1 | 4/1999 |
| WO | WO 99/42178 | 8/1999 |
| WO | WO 99/46005 | 9/1999 |
| WO | WO 9952594 A1 | 10/1999 |
| WO | WO 99/62599 | 12/1999 |
| WO | WO 00/25684 | 5/2000 |
| WO | WO 00/35534 | 6/2000 |
| WO | WO 0045701 A1 | 8/2000 |
| WO | WO 01/00271 A1 | 1/2001 |
| WO | WO 0130296 A1 | 5/2001 |
| WO | WO 01/68172 | 9/2001 |
| WO | WO 02/37449 A1 | 5/2002 |
| WO | WO 02/055149 | 7/2002 |
| WO | WO 02/092509 | 11/2002 |
| WO | WO 02/098509 | 12/2002 |
| WO | WO 04/022154 A2 | 3/2004 |
| WO | WO 2004075681 | 9/2004 |
| WO | WO 2004075731 | 9/2004 |
| WO | WO 05/025672 A1 | 3/2005 |
| WO | WO 2005025672 | 3/2005 |
| WO | WO 05/118067 A1 | 12/2005 |
| WO | WO 06/024038 A2 | 3/2006 |
| WO | WO 2006076506 | 7/2006 |
| WO | WO 06/087633 | 8/2006 |
| WO | WO 06/105254 | 10/2006 |
| WO | WO 06/115761 | 11/2006 |
| WO | WO 06/138659 | 12/2006 |
| WO | WO 2007089744 | 8/2007 |
| WO | WO 08/049905 | 5/2008 |
| WO | WO 08/054812 | 5/2008 |
| WO | WO 08/141296 | 11/2008 |
| WO | WO 09/019710 | 2/2009 |
| WO | WO 09/067323 A1 | 5/2009 |
| WO | WO 10/009452 A1 | 1/2010 |
| WO | WO 10/031777 | 3/2010 |

OTHER PUBLICATIONS

U.S. Appl. No. 10/723,171, filed Nov. 26, 2003, Streeter.

Agov, B. S., et al., "On the mechanism of therapeutic action of helium-neon laser in ischemic heart disease", *Klin Med* (Mosc), pp. 102-105, 1985.

Arvidsson, Andreas, et al., "Neuronal replacement from endogenous precursors in the adult rat brain after stroke", *Nature Medicine*, vol. 8, No. 9, Sep. 2002, pp. 963-970.

Asahi, Minoru, et al., Expression of Interleukin B Converting Enzyme Gene Family and bcl-2 Gene Family in the Rat Brain Following Permanent Occlusion of the Middle Cerebral Artery, *Journal of Cerebral Blood Flow & Metabolism*, vol. 17, No. 1, Jan. 1997.

Assia, E. et al., "Temporal Parameters of Low Energy Laser Irradiation for Optimal Delay of Post-Traumatic Degeneration of Rat Optic Nerve", Brain Research, vol. 476, 1989, pp. 205-212.

Basford, Jeffrey R., M.D., Ph.D., "Lasers in Orthopedic Surgery—Laser Therapy: Scientific Basis and Clinical Role", May 1993, vol. 16, No. 5, pp. 541-547.

Belkin, M. et al., "A Critical Review of Low Energy Laser Bioeffects", Lasers and Light in Ophthalmology, vol. 2, No. 1, pp. 63-71, 1988.

Bevilacqua et al.; "In Vivo Local Determiniation of Tissue Optical Properties: Applications to the Human Brain"; *Applied Optics*; vol. 28, No. 22; Aug. 1, 1999; pp. 4939-4950.

(56) References Cited

OTHER PUBLICATIONS

Bibikova, A. et al., "Enhancement of Muscle Regeneration in the Toad (*Bufo viridis*) Gastrocnemius Muscle by Low-Energy Laser Irradiation", The Anatomical Reocrd, vol. 235, 1993, pp. 374-380.

Bibikova, A. et al., "Enhancement of Angiogenesis in Regenerating Gastroenemius Muscle of the Toad (*Bufo viridis*) by Low-Energy Laser Irradiation", Anatomy and Embryology (1994), vol. 190, pp. 597-602.

Brazzle, John, et al., Active Microneedles with Integrated Functionality, *Technical Digest of the 2000 Solid-State Sensor and Actuator Workshop*, Department of Bioengineering, University of Utah, Salt Lake City, Utah 84112, 2000 (five pages).

Brill, G.E., et al., Modifying influence of low level laser irradiation on the relationships in endothelial cell-blood platelet system, *10th Congress of the European Society for Photobiology*, Vienna, Austria (one page). Jun. 8, 2004.

Byrnes, K.R., et al., Light Therapy Promotes Axonal Regeneration After Acute Spinal Cord Injury in Adult Rats, Program No. 275.2, *Society for Neuroscience*, 2003, Abstract.

Chance et al.: "Comparison of Time-Resolved and -Unresolved Measurements of Deoxyhemoglobin in Brain"; *Proc. Natl Acad. Sc.i USA;* vol. 85; ul. 1988; pp. 4971-4975.

Cohen, Michael A., Method of Forming Microneedles and other Micron-Scale Transdermal Probes, Office of Technology Licensing, University of California, Berkeley, http://otl.berkeley.edu/technology/inventiondetail. Php/1000335, Abstract (two pages) Dec. 5, 2003.

Conlan, M.J. et al., Biostimulation of Wound Healing by Low-Energy Laser Irradiation:, Journal of Clin. Periodontology, vol. 23, 1996, pp. 492-496.

Dirnagl, Ulrich, et al., Pathobiology of ischaemic stroke: an integrated view, *TINS*, vol. 22, No. 9, 1999, pp. 391-397.

Dobson, J., et al., Theory and Applications of a Magnetic Force Bioreactor, *European Cells and Materials*, vol. 4, Suppl. 2, 2002 (pp. 42-44).

Eells, J.T., et al., Therapeutic photobiomodulation for methanol-induced retinal toxicity, *Proceedings National Academy of Science (PNAS)*, vol. 100, No. 6, Mar. 18, 2003, pp. 3439-3444.

Elimadi, Aziz, et al., Trimetazidine Counteracts the Hepatic Injury Associated with Ischemia-Reperfusion by Michondrial Function, *Journal of Phamacology and Experimental Therapeutics*, vol. 286, No. 1, 1998, pp. 23-28.

Firbank et al.; "A Theoretical Study of the Signal Contributions of Regions of the Adult Head to Near-Infrared Spectroscopy Studies of Visual Evoked Responses"; *Neuroimage;* No. 8; 1998; pp. 69-78.

Fisher, M., "Characterizing the Target of Acute Stroke Therapy", Stroke, 1997, vol. 28, pp. 866-872.

Gage, Fred H., Brain, Repair Yourself, *Scientific American*, Sep. 2003, pp. 47-53.

Gasparyan, Levon V., Biochemical and Biophysical Effects of Low Level Laser Irradiation, *MAL 2000*, Helsinki, Finland (three pages), Sep. 28-30, 2000.

Gasparyan, Levon V., et al., Low Level Laser Therapy of Male Genital Tract Chronic Inflammations, *WALT 2-nd Congress* (Kansas City, USA), 1998 (two pages).

Gasparyan, Levon V., et al., The influence of LED irradiation at different wavelengths on functional activity of blood platelets, *10th Congress of the European Society of Photobiology*, Vienna, Austria, 2003 (one page).

Gasparyan, Levon V., et al., The influence of LED irradiation at different wavelengths with antioxidants on functional activity of blood platelets, Laser, Florence, 2003 (one page).

Gasparyan, Levon V., Experience of Russian (former USSR) Scientists in LLLT and UV Blood Irradiation, *MAL 2000*, Helsinki, Finland (four pages), Sep. 28-30, 2000.

Gasparyan, Levon V., Investigation of Sensations, Associated with Laser Blood Irradiation, *WALT 2-nd Congress* (Kansas City, USA), 1998 (two pages).

Gasparyan, Levon V., Millimeter Wave Therapy, *MAL 2000*, Helsinki, Finland (three pages). Sep. 28-30, 2000.

Gordon, G. A., "The Use of low power lasers in sports medicine", *Clinical Sports Medicine 2*, 53-61 (1990).

Gross, Garrett J., et al., Mechanisms of Postischemic Contractile Dysfunction, Myocardial Protection From Surgical Ischemic-Reperfusion Injury, *An International Symposium*, Asheville, North Carolina, Sep. 21-24, 1997, pp. 1898-1904.

Iadecola, Costantino, et al., Inhibition of inducible nitric oxide synthase ameliorates ischemic damage, *Am. J. Physiol.*, vol. 268, 1995, pp. R286-R292.

Karu, T.I., Low power laser therapy, in *Biomedical Photonics Handbook*, Ch. 48, Editor-in-Chief Tuan Vo-Dinh, Boca Raton, CRC Press, 2003.

Karu, Tiina, Mechanisms of interaction of monochromatic visible light with cells, *Proc. SPIE*, vol. 2630, pp. 2-9, 1996.

Karu, Tiina, Mechanisms of Low-Power Laser Light Action on Cellular Level, Effects of Low-Power Light on Biological Systems V, *Proceedings of SPIE*, Jul. 7, 2000, vol. 4159 pp. 1-17.

Karu, Tiina, Photobiological Fundamentals of Low Power Laser Therapy, *IEEE Journal of Quantum Electronics*, vol. QE-23, No. 10, Oct. 1987, pp. 1703-1717.

Karu, et al., Biostimulation of HeLa Cells by Low-Intensity Visible Light. II. Stimulation of DNA and RNA Synthesis in a Wide Spectral Range. IL Nuovo Cimento. (1984) p. 309-318.

Laser Exchange: Delivering the medicine of the future, http://www.laserexchange.co.uk/laser-therapy/ultrasound.htm; 42 pages, Oct. 13, 2004.

Leung, Mason C.P., et al., Treatment of Experimentally Induced Transient Cerebral Ischemia with Low Energy Laser Inhibits Nitric Oxide Synthase Activity and Up-Regulates the Expression of Transforming Growth Factor-Beta 1, *Laser in Surgery and Medicine*, 31:283-288 (2002).

Lychagov, Vladislav V., et al. Experimental study of NIRtransmittance of the human skull, *Proc. Of SPIE*, vol. 6085, 2006 (five pages).

Mester, E., et al., Effect of Laser Rays on Wound Healing, *The American Journal of Surgery*, vol. 122, Oct. 1971, pp. 532-535.

Mochizuki-Oda, Noriko, et al., Effects of near-infra-red laser irradiation on adenosine triphosphate and adenosine diphosphate contents of rat brain tissue, *Neuroscience Letters 323*, May 3, 2002, pp. 207-210.

Nishioka, Norman S., et al., Reflection and Transmission of Laser Light From the Esophagus: The Influence of Incident Angle, *Gastroenterology*, vol. 94, 1988, pp. 1180-1185.

Nissan, M. et al., "HeNe Laser Irradiation Delivered Transcutaneously: Its Effect on the Sciatic Nerve of Rats", Lasers in Surgery and Medicine, vol. 6, pp. 435-438, 1986.

Olesin, AI, et al., Laser irradiation of venous blood for production of reperfusion syndrome in myocardial infarction, *Patologisheskaia fiziologiia*, Sep.-Dec. 1992 (5-6) p. 20-3, ISSN 0031-2991 Journal Code: 0376421, English abstract of Russian article).

Oron, Uri, et al., Attenuation of Infarct Size in Rats and Dogs after Myocardial Infarction by Low-Energy Laser Irradiation, *Lasers in Surgery and Medicine*, vol. 28, 2001, pp. 204-211.

Oron, Uri, et al., Low-Energy Laser Irradiation Reduces Formation of Scar Tissue After Myocardial Infarction in Rats and Dogs, Circulation, vol. 103, Jan. 16, 2001, pp. 296-301.

Park, James L., Ph.D., et al., Mechanisms of Myocardial Reperfusion Injury, The Annals of Thoracic Surgery, *Official Journal of Thoracic Surgeons and the Southern Thoracic Surgical Association*, vol. 68, No. 5, Nov. 1999, pp. 1905-1912.

International Search Report for PCT/CA99/00156, dated Jun. 11, 1999.

International Search Report and Written Opinion for PCT/US2007/002219, dated Jul. 5, 2007.

International Preliminary Report on Patentability for PCT/US2007/002219, dated May 2, 1998.

International Search Report and Written Opinion for PCT/US2007/002474, dated Sep. 28, 2007.

International Preliminary Report on Patentability for PCT/US2007/002474, dated Apr. 16, 2008.

International Search Report for PCT/US02/36808, dated Apr. 2, 2003.

(56) References Cited

OTHER PUBLICATIONS

International Search Report for PCT/US03/00747, dated May 14, 2003.
International Preliminary Report on Patentability for PCT/US04/029724, dated Mar. 23, 2006.
International Preliminary Report on Patentability for PCT/US2005/004873, dated Sep. 14, 2006.
International Search Report and Written Opinion for PCT/US2005/004873 , dated Sep. 5, 2005.
Physical Therapy, The Efficacy of Laser Therapy for Musculoskeletal and Skin Disorders: A Criteria-Based Metanalysis of Randomized Clinical Trials, vol. 72, No. 7, Jul. 1992, pp. 483/12-491/21.
Pogue et al.: "Comparison of Image Geometries for Diffuse Optical Tomography of Tissue"; *Optics Express;* vol. 4, No. 8; Apr. 12, 1999; pp. 270-286.
Semenza, Gregg L., et al., Regulation of Mammalian O2 Homeostatis by Hypoxia-Inducible Factor 1, *Ann. Rev. Cell Dev. Biol.,* vol. 15, 1999, pp. 551-578.
Smith, Kendric C., "The Photobiological Basis of Low Level Laser Radiation Therapy", *Photobiological Basis of LLLT,* pp. 1-7, 1991.
Stys, Peter K., Anoxis and Ischemic Injury of Myelinated Axons in CNS White Matter: From Mechanistic Concepts to Therapeutics, *J. Cereb. Blood Flow Metab.,* vol. 18, No. 1, Jan. 1998, 42 pages. (037C1 lists pp. 2-25).
Thor: Is LLT Different from Ultrasound?, http://www.thorlaser.com/LLLT/is-LLLT-diff-from-ultrasound.htm, 2 pages, Oct. 13, 2004.
Thor, Specification, 30mW Red Laser probe, www.thorlaser.com/specs/680.html, web page (1 page), Oct. 6, 1999.
Thor Laser, 100mW, Thor, lllt, LLLT, Low Level Laser Therapy, low level laser therapy, Lazer, Thorl., http://www.thorlaser.com/specs/_100m_W.html, Oct. 6, 1999, p. 1.
Thor, Specification, 200mW/810nm Laser probe, http://www.thorlaser.com/specs/_200mWhtml, web page (1 page), Oct. 6, 1999.
Thor, Specification, 200mW/650nm Laser probe, http://www.thorlaser.com/specs/200mW650nm.html, web page (1 page), Oct. 6, 1999.
Thor, Specification, 500mW/810nm Laser probe, http://www.thorlaser.com/specs/_500mW.html, web page (1 page), Oct. 6, 1999.
Thor Laser, Specifications, Thor: Specifications, Thor, lllt, LLLT, Low Level Laser Therapy, low level laser therapy, http://www.thorlaser.com/specs, Oct. 6, 1999, pp. 1-2.
Thor: Product List, Thor, lllt, LLLT, Low Level Laser Therapy, Laz., http://www.thorlaser.com/prodlist/index.html, Oct. 6, 1999, pp. 1-4.
Toon, John, Taking the "Ouch" Out of Needles: Arrays of Micron-Scale "Microneedles" Offer New Technique for Drug Delivery, *Georgia Tech Research News,* Jun. 22, 1998 (three pages).
Toricelli, P., et al., Laser Biostimulation of cartilage: in vitro evaluation, *Biomed. Pharmacother.,* 2001, vol. 55, pp. 117-120.
Tuchin, Valery, Tissue Optics: Light Scattering Methods and Instruments for Medical Diagnosis, SPIE Press, Tutorial Texts in *Optical Engineering,* vol. TT38, 2000, pp. 3-11.
Tunér, Jan, et al., Low Level Laser Therapy, Clinical Practice and Scientific Background, Prima Books in Sweden AB, 1999, pp. 1-9, 45-58, 62-114, 113-116, 118, 132-134, 134-135, 149-151, 151-156, 185, 334-364.
Van Breugel, Hans H.F.I., et al., Power Density and Exposure Time of He—Ne Laser Irradiation are More Important than Total Energy Dose in Photo-Biomoducation of Human Fibroblasts InVitro, *Lasers in Surgery and Medicine* (1992), Wiley-Liss, Inc., pp. 528-537.
Van Breugel et al. "He—Ne laser irradiation affects proliferation of cultured rat-Schwann cells in a dose-dependent manner," Journal of Neurocytology 22, 185-190 (1993).
Weiss, N. et al., "Enhancement of Muscle Regeneration in the Rat Gastrocnemius Muscle by Low Energy Laser Irradiation", Anat. Embroyl. (1992), vol. 186, pp. 497-503.
Wong-Riley, Margaret T.T., et al., Light-emitting diode treatment reverse the effect of TTX on cytochrome oxidase in neurons, *NeuroReport,* vol. 12, No. 14, Oct. 8, 2001, pp. 3033-3037.
Yaakobi, Tali, et al., Long-term effect of low energy laser irradiation on infarction and reperfusion injury in the rat heart, *J. Appl. Physiol.,* vol. 90, 2001, pp. 2411-2419.

EPO Extended Search Report re EP Application No. 09170679.6, dated Jan. 4, 2010. in 6 pages.
"Is Laser Therapy Overtaking Ultrasound?" http://www.laser.uk.com/laser, Therapy vs. ultrasound.html, dated Feb. 20, 1999.
"Association of outcome with early stroke treatment: pooled analysis of Atlantis, ECASS, and NINDS rt-PA stroke trials," The Lancet, vol. 363, Mar. 6, 2004, pp. 768-774.
"Laser Exposure Limits & Hazard Calculations," Excerpts from OSHA Technical Manual, Chapter 6: Laser Hazards, date unknown.
Accelrys, "Optical Absorption Spectra of Melanins—a Comparison of Theoretical and Experimental Results," Chemicals Case Study, Accelyrys, Oct. 5, 2005, http://accelrys.com/references/case-studies/archive/studies/melanins_partII.pdf.
Adachi, Naoto, "Cerebral ischemia and brain histamine," Brain Research Reviews 50 (2005) 275-286.
Adamic, Metka et al., "Vascular lasers and IPLS: Guidelines for care from the European Society for Laser Dermatology (ESLD)," Journal of Cosmetic and Laser Therapy, 2007; 9: 113-124.
Albertini, R. et al., "COX-2 mRNA expression decreases in the subplantar muscle of rat paw subjected to carrageenan-induced inflammation after low level laser therapy," Inflammation Research, 56 (2008) pp. 228-229.
Albrecht-Buehler, Guenter. "Reversible, excitation light-induced enhancement of fluorescence of live mammalian mitochondria," The FASEB Journal, vol. 14, Oct. 2000, pp. 1864-1866.
Alerstam, Erik et al., "Parallel computing with graphics processing units for high-speed Monte Carlo simulation of photon migration," Journal of Biomedic Optics, vol. 13(6), Nov./Dec. 2008.
Alexopoulous, George S. et al., "Clinically Defined Vascular Depression," American Journal of Psychiatry, 154:4, Apr. 1997, pp. 562-565.
Amat, Albert et al., "Modification of the intrinsic fluorescence and the biochemical behavior of ATP after irradiation with visible and near-infrared laser light," Journal of Photochemistry and Photobiology B: Biology 81 (2005) 26-32.
Anders et al., Low power laser irradiation alters the rate of regeneration of the rat facial nerve, Laser Surg. Med., 13:72-82 (1993).
Anders, Juanita J., "The Potential of Light Therapy for Central Nervous System Injury and Disease," Photomedicine and Laser Surgery, vol. 27, No. 3 (2009) pp. 379-380.
Anonymous, "Engineer, heal thyself," News Brief, Optoelectronics Report 3, www.optoelectronics-world.com, Nov. 1, 1999.
Anonymous, "Practice Guideline for the Treatment of Patients With Major Depressive Disorder (Revision)," Am. J. Psychiatry, 257: 4, Apr. 2000, pp. 1-43.
Arthur, Charles R., "Parkinson's Disease Brain Mitochondria Have Impaired Respirasome Assembly, Age-Related Increases in Distribution of Oxidative Damage to mtDNA and No Differences in Heteroplasmic mtDNA Mutation Abundance," Molecular Degeneration, http://www.molecular neurodegeneration.com/content/4/1/37, Sep. 23, 2009.
Assia et al., "Temporal Parameters of Low Energy Laser Irradiation for Optimal Delay of Post-Traumatic Degeneration of Rat Optic Nerve", Brain Research, vol. 476, 1989, pp. 205-212.
Association of outcome with early stroke treatment: pooled analysis of Atlantis, ECASS, and NINDS rt-PAT stroke trials, The Lancet, vol. 363, Mar. 6, 2004, pp. 768-774.
Atamna, Hani et al., "Mechanisms of mitochondrial dysfunction and energy deficiency in Alzheimer's disease," Mitochondrion 7 (2007) pp. 297-310.
Ataullakhanov et al. "What Determines the Intracellular ATP Concentration," Bioscience Reports, vol. 22, No. 5 and 6, Oct. and Dec. 2002.
Avni, Dorit et al., "Protection of Skeletal Muscles from Ischemic Injury: Low-Level Laser Therapy Increases Antioxidant Activity", Photomedicine and Laser Surgery vol. 23, No. 3, 2005, p. 273-277.
Barnett, Alex H. et al., "Robust inference of baseline optical properties of the human head with three-dimensional segmentation from magnetic resonance imaging," Applied Optics, vol. 42, No. 16, Jun. 1, 2004, pp. 3095-3108.
Bashkatov, A.N. et al., "Estimate of the melanin content in human hairs by the inverse Monte-Carlo method using a system for digital image analysis," Quantum Electronics 36(12) 1111-1118 (2006).

(56) References Cited

OTHER PUBLICATIONS

Baxter, Richard, "Laser Safety Training Manual," University of Chicago Chemistry Department, date unknown.
Beal, M. Flint, "Mitochondrial Dysfunction and Oxidative Damage in Alzheimer's and Parkinson's Diseases and Coenzyme Q10 as a Potential Treatment," Journal of Bioenergetics and Biomembranes, vol. 26, No. 4, Aug. 2004, pp. 381-386.
Beauvoit, B. et al. "Contribution of the Mitochondrial Compartment to the Optical Properties of the Rat Liver: A Theoretical and Practical Approach," Biophysical Journal, vol. 67, Dec. 1994, pp. 2501-2510.
Ben-Shachar, Dorit et al., "Neuroanatomical Pattern of Mitochondrial Complex I Pathology Varies between Schizophrenia, Bipolar Disorder and Major Depression," PLoS One, Nov. 2008, vol. 3, Issue 11.
Bevers, Matthew B. et al., "Mechanistic role of calpains in postischemic neurodegeneration," Journal of Cerebral Blood Flow & Metabolism (2008) 28, 655-673.
Bisland, Stuart K. et al., "To begin at the beginning: The science of bio-stimulation in cells and tissues," Proc. of SPIE, vol. 6140, 2006.
Boelens, R. et al., "EPR Studies of the Photodissociation Reactions of Cytochrome c Oxidase-Nitric Oxide Complexes," Biochimica et Biophysica Acta, 679 (1982) pp. 84-94.
Boelens, Rolf et al., "An EPR Study of the Photodissociation Reactions of Oxidised Cytochrome c Oxidase-Ntiric Oxide Complexes," Biochimica et Biophysica Acta, 924 (1983) pp. 176-183.
Bonnet, Sébastien et al., "A Mitochondria-K+ Channel Axis is Suppressed in Cancer and its Normalization Promotes Apoptosis and Inhibits Cancer Growth," Cancer Cell 11, 37-51, Jan. 2007.
Borutaite, Vilmante et al., "Reversal of nitric oxide-, peroxynitrite- and S-nitrosothiol-induced inhibition of mitochondrial repiration or complex I activity by light and thiols," Biochimica et Biophysica Acta, 1459, (2000) pp. 405-412.
Brain Injury Source, vol. 3, Issue 4 (1999).
Brennan, Angela M. et al., "NADPH oxidase is the primary source of superoxide induced by NMDA receptor activation," Nature Neuroscience, vol. 12, No. 7, Jul. 2009, pp. 857-864.
Broughton, Brad R.S. et al. "Apoptic Mechanisms After Cerebral Ischemia," Stroke, stroke.ahajournals.org, May 2009.
Brown, G.C., "Mechanisms of inflammatory neurodegeneration: iNOS and NADPH oxidase," Biochemical Society Transactions (2007) vol. 35, part 5, pp. 1119-1121.
Brown, Robert D. et al., "International Stroke Conference Poster Presentations," Stroke, vol. 37, No. 2, Feb. 2006.
Bruch, Reinhard. "Low Level Laser Therapy (LLLT)," Nevada Health Forum, Dec. 4, 2003.
Buck, L.T. et al., "Adaptive responses of vertebrate neurons to anoxia—Matching supply to demand," Respiratory Physiology & Neurobiology 154 (2006) 226-240.
Buckman, Jennifer F. et al., "Spontaneous Changes in Mitochondrial Membrane Potential in Cultured Neurons," The Journal of Neuroscience, Jul. 15, 2001, 21(14): 5054-5065.
Bullock, M. Ross et al., "Outcome measures for clinical trials in neurotrauma," Neurosurg. Focus 13 (1): Jul. 2002, pp. 1-11.
Calabrese, Vittorio et al., "Nitric oxide in the central nervous system: neuroprotection versus neurotoxicity," Nature Reviews: Neuroscience, vol. 8, Oct. 2007, pp. 766-775.
Calabresi, Paolo et al., "Sodium Influx Plays a Major Role in the Membrane Depolarization Induced by Oxygen and Glucose Deprivation in Rat Striatal Spiny Neurons," Stroke, stroke.ahajournals.org, Jan. 1999, pp. 171-179.
Carroll, James D., "A 3D dose model for low level laser/led therapy biostimulation and bioinhibition," Proc. of SPIE, vol. 6846, 2008.
Carroll, James S et al., "Red Blood Cell Stimulation of Platelet Nitric Oxide Production Indicated by Quantitative Monitoring of the Communication between Cells in the Bloodstream," Analytical Chemistry, vol. 79, No. 14, pp. 5133-5138, Jul. 15, 2007.

Castello, Pablo et al., "Oxygen-regulated isoforms of cytochrome c oxidase have differential effects on its nitric oxide production and on hypoxic signaling," PNAS Early Edition, www.pnas.org/cgi/doi/10.1073/pnas.0709461105, 2008.
Catanzaro et al. "Managing Tissue Heating in Laser Therapy to Enable Double-Blind Clinical Study," Proc. SPIE, vol. 6140, 614000 (2006).
Cellular Model Studies of Brain-Mediated Monochromatic Phototherapy on Alzheimer's Disease, Chinese Journal of Lasers, 0258-7-25 (2009) Supplement 1-0190-04.
Celsi, Fulvio et al., "Mitochondria, calcium and cell death: A deadly triad in neurodegeneration," Biochim. Biophys. Acta., May 2009; 1787(5): 335-344.
Chan, C. Savio et al., "Rejuvenation protects neurons in mouse models of Parkinson's disease," Nature, vol. 447, Jun. 28, 2007.
Chen, Aaron Chih-Hao et al., "Low Level Laser Therapy activates NF-kB via Generation of Reactive Oxygen Species in Mouse Embryonic Fibroblasts," Proc. of SPIE, vol. 7165, 2009.
Chen, James et al., "New Technology for Deep Light Distribution in Tissue for Phototherapy," The Cancer Journal, vol. 8, No. 2, Mar./Apr. 2002, pp. 154-163.
Chiros Equipment Supplies, "Erchonia The healing light," http://www.chiros.com/au.erchonia.php, Accessed Feb. 7, 2002.
Chow, Roberta T. et al., "830nm laser irradiation induces varicosity formation, reduces mitochondrial membrane potential and blocks fast axonal flow in small and medium diameter rat dorsal root ganglion neurons: implications for the analgesic effect of 830nm laser," Journal of the Peripheral Nervous System, 12:28-39 (2007).
Custo, Anna et al., "Comparison of Diffusion and Transport in human head," date unknown.
Custo, Anna et al., "Effective scattering coefficient of the cerebral spinal fluid in adult head models for diffuse optical imaging," Applied Optics, vol. 45, No. 19, Jul. 1, 2006, pp. 4747-4756.
Dawson, Elizabeth et al., "Adverse Events Associated With Nonablative Cutaneous Laser, Radiofrequency, and Light-Based Devices," Seminars in Cutaneous Medicine and Surgery, 2007, pp. 15-21.
de Groot, A.C. et al., "Bijwerkingen van Lasertherapie," Nederlands Tijdschrift voor Dermatologie & Venereologie, vol. 16, Sep. 2006 (In Dutch).
Dejean, Laurent M. et al., "Oligomeric Bax is a Component of the Putative Cytochrome c Release Channel MAC, Mitochondrial Apoptosis-induced Channel," Molecular Biology of the Cell, vol. 16, 2424-2432, May 2005.
Delori, François et al., "Maximum permissible exposures for ocular safety (ANSI 2000), with emphasis on ophthalmic devices," J. Opt. Soc. Am. A., vol. 24, No. 5, May 2007, pp. 1250-1265.
Demaurex, Nicolas et al., "Reactive oxygen species are NOXious for neurons," Nature Neuroscience, vol. 12, No. 7, Jul. 2009, pp. 819-820.
Desmet, et al.: "Clinical and Experimental Applications of NIR-LED Photobiomodulation"—Photomedicine and Laser Surgery—2006;24(2): 121-128.
DeTaboada, L., et al.: "Transcranial Application of Low-Energy Laser irradiation Improves Neurological Deficits in Rats Following Acute Stroke" The American Stroke Association International Stroke Conference 2006. Stroke 2006; 37(2):731.
DeTaboada, L., et al.: "Transcranial Application of Low-Energy Laser Irradiation Improves Neurological Deficits in Rats Following Acute Stroke", Lasers in Surgery and Medicine 38:70-73 (2006).
Dhar, Shilpa S. et al., "Chromosome Conformation Capture of all 13 Genomic Loci in the Transcriptional Regulation of the Multisubunit Bigenomic Cytochrome C Oxidase in Neurons," The Journal of Biological Chemistry. 2009.
Diamond, Solomon Gilbert, "Cognitive Effects on the Neurophysiology and Biomechanics of Stroke Recovery," Harvard University, Jan. 2004.
Dohare, Preeti et al., "Neuroprotective efficacy and therapeutic window of curcuma oil: in rat embolic stroke model," BMC Complementary and Alternative Medicine 2008, 8:55.
Duncan, Pamela et al., "Randomized Clinical Trial of Therapeutic Exercise in Subacute Stroke," Stroke, Sep. 2003.
Eggen Furre, Ingregerd et al., "Involvement of both caspase-dependent and -independent pathways in apoptotic induction by

(56) References Cited

OTHER PUBLICATIONS hexaminolevulinate-mediated photodynamic therapy in human lymphoma cells," Apoptosis (2006) 11:2031-2042.
Fedorov, et al.: Non-invasive alternating current stimulation induces recovery from stroke, Restorative Neurology and Neuroscience 28 (2010) 825-833.
Franceschini, Maria Angela et al., "Near-Infrared Absorption and Scattering Spectra of Tissues in Vivo," date unknown.
Frigo, Lucio et al., "The effect of low-level laser irradiation (Ga—Al—AsP-660nm) on in vitro and in vivo melanoma," http://www.biomedcentral.com/1471-2407/9/404, Nov. 20, 2009.
Furlan, Anthony J., "Acute Stroke Trials: Strengthening the Underpowered," Stroke and Neurological Intensive Care, vol. 33(6), Jun. 2002, pp. 1450-1451.
Galuzzi, Lorenzo et al., "Targeting post-mitochondrial effectors of apoptosis for neuroprotection," Biochim. Biophys. Acta (2008), doi:10.1016/j.bbabio.2008.09.006.
Gao, Zuejuan et al., "Molecular mechanisms of cell proliferation induced by low power laser irradiation," Journal of Biomedical Science, 16:4, 2009.
Gasparyan, Levon et al., "Activation of Angiogenesis Under Influence of Red Low Level Laser Radiation," Laser Florence, 2004, pp. 1-8.
Ginsberg, Myron D., "Neuroprotection for ischemic stroke: Past, present and future," Neuropharmacology, 2008, pp. 1-27.
Giuliani, Alessandro et al., "Low infra red laser light irradiation on cultured neural cells: effects on mitochondria and cell viability after oxidative stress," BMC Complementary and Alternative Medicine 2009, 9:8.
Go-Jo, Inc., (2002). "Watch for 'Subtle Energies' Featuring Dr. Larry Lytle," Flyer, South Dakota.
Goldstein, Larry B. et al., "Patient Safety in Trials of Therapy for Acute Ischemic Stroke," The Journal of the American Medical Association, vol. 287, No. 8, Feb. 27, 2002.
Goldstein, Larry B. et al., "Veterans Administration Acute Stroke (VASt) Study: Lack of Race/Ethnic-Based Differences in Utilization of Stroke-Related Procedures or Services," Stroke, Apr. 2003, pp. 999-1004.
Gourley, Paul L. et al., "Optical Phenotyping of Human Mitochondria in a Biocavity Laser," IEEE Journal of Selected Topics in Quantum Electronics, vol. 11, No. 4, Jul./Aug. 2005.
Hacke, Werner et al., "Thrombolysis with Alteplase 3 to 4.5 Hours after Acute Ischemic Stroke," The New England Journal of Medicine, vol. 359, No. 13, Sep. 25, 2008, pp. 1317-1329.
Haitsma, Iain K. et al., "Monitoring cerebral oxygenation in traumatic brain injury," Progress in Brain Research, vol. 161, Chapter 14, pp. 207-216, 2007.
Hamblin et al. "Mechanisms of Low Level Light Therapy," Proc. of SPIE, vol. 6140 614001-1 (2006).
Hancock, Celeste M. et al., "Modulation of Pain in Osteoarthritis: The Role of Nitric Oxide," Clin. J. Pain, vol. 24, No. 4, May 2008, pp. 353-365.
Hankey, Graeme J. et al., "Treatment and secondary prevention of stroke: evidence, costs, and effects on individuals and populations," The Lancet, vol. 354, Oct. 23, 1999, pp. 1457-1463.
Harris, David M et al., "Laser Biostimulation: Review and Hypothesis," Laser Topics, 1988, pp. 9-14.
Häusser, Michael et al., "Controlling neural circuits with light," Nature: News & Views, vol. 446, Apr. 5, 2007, pp. 617-619.
Hawkins, Denise et al., "How Long After Laser Irradiation Should Cellular Responses be Measured to Determine the Laser Effects?" Journal of Laser Applications, vol. 19, No. 2, May 2007, pp. 74-83.
Hawkins-Evans, Denise et al., "Effect of Wavelength and Fluence on Morphology, Cellular and Genetic Integrity of Diabetic Wounded Human Skin Fibroblasts," Proc. of SPIE vol. 6140, p. 614006-1 to 614006-13.
Hawkins-Evans, Denise et al., "Efficacy of a single high does versus multiple low doses of LLLT on wonded skin fibroblasts," Proc. of SPIE vol. 6632, p. 66321U-1 to 66321U-12.

Henchcliffe, Claire et al., "Mitochondrial biology and oxidative stress in Parkinson disease pathogenesis," Nature Clinical Practice Neurology, vol. 4, No. 11, Nov. 2008.
Hetz, Claudio et al., "Bax Channel Inhibitors Prevent Mitochondrion-mediated Apoptosis and Protect Neurosn in a Model of Global Brain Ischemia," The Journal of Biological Chemistry, vol. 280, No. 52, pp. 42960-42970, Dec. 30, 2005.
Hilf, Russell, "Mitochondria are targets of photodynamic therapy," J. Bioenerg. Biomembr. (2007) 39:85-89.
Hollenbeck, Peter J., "The Pattern and Mechanism of Mitochondrial Transport in Axons," Frontiers in Bioscience 1, Jul. 1, 1996.
Hölscher, Theo et al., "Transcranial Sound Field Characterization in the Scope of Sonothrombolysis," University of California San Diego, Medical Center, date unknown.
Hori, Yasuaki et al., "Automatic characterization and segmentation of human skin using three-dimensional optical coherence tomography," Optics Express, vol. 14, No. 5, Mar. 6, 2006, pp. 1862-1877.
Horvat, Susann et al., "Effect of hypoxia on the transcription pattern of subunits isoforms and the kinetics of cytochrome c oxidase in cortical astrocytes and cerebellar neurons," Journal of Neurochemistry, 2006, 99, 937-951.
Hou, Xinlin et al., "Research on the relationship between brain anoxia at different regional oxygen saturations and brain damage using near-infrared spectroscopy," Physiological Measurement 28, 2007, pp. 1251-1265.
Hu, Wan-Ping et al., "Helium-Neon Laser Irradiation Stimulates Cell Proliferation through Photostimulatory Effects in Mitochondria," Journal of Investigative Dermatology (2007), vol. 127, pp. 2048-2057.
Hüttemann, Maik et al., "Regulation of oxidative phosphorylation, the mitochondrial membrane potential, and their role in human disease," J. Bioenerg. Biomembr (2008) 40:445-456, pp. 445-456.
Ilev, i., et al., "Smart optical fiber probes for precise tissue treatment," Proc. SPIE, 4616:220-228 (2002).
Ilic, S., et al.: "Effects of Power Densities, Continuous and Pulse Frequencies, and Number of Sessions of Low-Level Laser Therapy on Intact Rat Brain" Photomedicine and Laser Surgery 2006; 24(4): 458-466.
INVOS® Cerebral Oximeters, 2000 Mallinckrodt.
Ionto Comed® Product Brochure, date unknown, (In Greek).
Jacques, Steven L. "Skin Optics," Oregon Medical Laser Center News, Jan. 1998, http://omlc.ogi/edu/news/jan98/skinoptics.html.
Jacques, Steven L. et al., "Tutorial on diffuse light transport," Journal of Biomedical Optics, 13(4), 041302 (Jul./Aug. 2008).
Jauss, M. et al., "Surgical and medical management of patients with massive cerebellar infarctions: results of the German-Austrian Cerebellar Infarction Study," J. Neurol. (1999) 246: 257-264.
Jekabsone, Aiste et al., "Nitric oxide from neuronal nitric oxide synthase sensitises neurons to hypoxia-induced death via competitive inhibition of cytochrome oxidase," Journal of Neurochemistry, 2007.
Jou, Shaw-Hwa et al., "Mitochondrial Dysfunction and Psychiatric Disorders," Chang Gung Med. J., vol. 32, No. 4, Jul.-Aug. 2009, pp. 370-379.
Kahn, Fred et al., "Low Intensity Laser Therapy: The clinical approach," Proc. of SPIE, vol. 6140, 2008.
Kaplan, Justin et al., "Mechanisms of Ischemic Cerebral Injury," Resuscitation, 15 (1987) pp. 149-169.
Kaplan, Michael, "The Theralaser," date unknown.
Karrer et al., Long Pulsed Dye Laser for Photodynamic Therapy: Investigations In Vitro and In Vitro; Lasers in surg & Med.: vol. 25; 1999; pp. 51-59.
Karu et al. "Cell Attachment to Extracellular Matrices is Modulated by Pulsed Radiation at 820 nm and Chemicals that Modify the Activity of Enzymes in the Plasma Membrane," Lasers in Surgery and Medicine, 29: 274-281 (2001).
Karu, T.I., "Cellular mechanisms of low-power laser therapy," Proc. of SPIE, vol. 5149, 2003, pp. 60-66.
Karu, Tiina I, "Mitochondrial Signaling in Mammalian Cells Activated by Red and Near-IR Radiation," Photochemistry and Photobiology, 2008, 84: 1091-1099.

(56) References Cited

OTHER PUBLICATIONS

Karu, Tiina I. et al., "A Novel Mitochondrial Signaling Pathway Activated by Visible-to-near Infrared Radiation," Photochemistry and Photobiology, 2004, 80: 366-372.

Karu, Tiina I. et al., "Cellular Effects of Low Power Laser Therapy Can be Mediated by Nitric Oxide," Lasers in Surgery and Medicine, 36:307-314 (2005).

Karu, Tiina I. et al., "Changes in absorbance of monolayer of living cells induced by laser irradiation at 633, 670, and 820 nm," Proc. of SPIE, vol. 4431, 2002, pp. 306-312.

Karu, Tiina I. et al., "Irradiation with a diode at 820 nm induces changes in circular dichroism spectra (250-780 nm) of living cells," Proc. of SPIE, vol. 4433, 2001, pp. 97-102.

Karu, Tiina, "Primary and secondary mechanisms of action of visible to near-IR radiation on cells," Journal of Photochemistry and Photobiology, 49 (1999) pp. 1-17.

Karu, Tiina, "Primary mechanisms of action of low-intensity laser light on cells," SPIE, vol. 3829, 1999, pp. 42-53.

Karu, Tiina. "Can a mechanism based on changes in redox properties of cytochrome c oxidase be crucial in explaining of low-power laser effects?" SPIE, vol. 3732, 1999. pp. 202-213.

Kaushal, Vikas et al., "Mechanisms of Microglia-Mediated Neurotoxicity in a New Model of the Stroke Penumbra," The Journal of Neuroscience, 28(9): 221-2230, Feb. 27, 2008.

Kemp, Graham J., "Mitochondrial dysfunction in chronic ischemia and peripheral vascular disease," Department of Musculoskeletal Science, Royal Liverpool University Hospital, University of Liverpool, Jul. 12, 2004.

Khodjakov, Alexey et al., "Laser micro-irradiation of mitochondria: is there an amplified mitochondrial death signal in neural cells?" Mitochondrion 3 (2004) pp. 217-227.

Kiguchi, Masashi et al., "Comparison of light intensity on the brain surface due to laser exposure during optical topography and solar irradiation," Journal of Biomedical Optics 12(6), Nov./Dec. 2007.

Kim, Kyunghan et al., "Ultrafast Laser Radiation and Conduction Heat Transfer in Biological Tissues," Proceedings of IMECE2005, 2005 ASME International Mechanical Engineering Congress and Exposition, Nov. 5-11, 2005.

Kofke, W. Andrew et al., "Near Infrared Laser Therapy," University of Pennsylvania, 2009.

Kosiak, Michael M.D.,: "Etiology and Pathology of Ischemic Ulcers", Archives of Physical Medicine and Rehabilitation, vol. 40, No. 1, 37th Annual Session, Minneapolis, Aug. 30-Sep. 4, 1959, pp. 62-69.

Krieger, Derk W. et al., "Cooling for Acute Ischemic Brain Damage (COOL AID): An Open Pilot Study of Induced Hypothermia in Acute Ischemic Stroke," Stroke, Aug. 2001, pp. 1847-1854.

Lam, T.S., et al.: "Laser stimulation of collagen synthesis in human skin fibroblast cultures," Lasers Life Sci, 1:61-77 (1986).

Lampl, Yair et al.: "Infrared Laser Therapy for Ischemic Stroke: A New Treatment Strategy", 2007 American Heart Association, Inc., pp. 1843-1849.

Lampl, Yair, "Laser treatment for stroke," Expert Rev. Neurotherapeutics 7(8), 2007.

Lane, Nick "Power Games" Nature/vol. 443/Oct. 26, 2006, Nature Publishing Group, pp. 901-903.

Lapchak, P. A., et al.: "Transcranial Infrared Laser Therapy Improves Clinical Rating Scores After Embolic Strokes in Rabbits", Stroke 2004; 35: 1985-1988.

Lapchak, P. A., et al.: "Transcranial Near-Infrared Light Therapy Improves Motor Function Following Embolic Strokes in Rabbits: An Extended Therapeutic Window Study Using Continuous and Pulse Frequency Delivery Modes"—Neuroscience 148 (2007) 907-914.

Lapchak, P. A., et al.: "Transcranial near infrared laser treatment (NILT) increases cortical eadenosine-5'-triphosphate (ATP) content following embolic strokes in rabbits", ScienceDirect, Brain Research 1306 (2010) pp. 100-105.

Lapchak, Paul A. "Transcranial Laser Energy Improves Motor Function Following Embolic Strokes in Rabbits: An Extended Therapeutic Window Study Using Continuous and Pulse Frequency Delivery Modes," Exp. Neurol. 2007.

Lapchak, Paul A. et al., "Advances in ischemic stroke treatment: neuroprotective and combination therapies," Expert Opin. Emerging Drugs, Mar. 2007, vol. 12, No. 1, pp. 97-112.

Lapchak, Paul A. et al., "Safety Profile of Transcranial Near-Infrared Laser Therapy Administered in Combination with Thrombolytic Therapy to Embolized Rabbits," Stroke, Nov. 2008.

Lasermedics, Inc., "The Effects of the Microlight 830 on Repetitive Stress Injuries," Aug. 4, 1993.

Leker, R. R., et al.: "Cerebral ischemia and trauma—different etiologies yet similar mechanisms: neuroprotective opportunities", Brain Research Reviews 39 (2002) pp. 55-73.

Levitt, Pat, "Sealing Cortical Cell Fate," Science, vol. 303, Jan. 2, 2004, pp. 48-49.

Li, Ming-jun, "Managing nonlinearity in optical fiber for high-power lasers," The International Society for Optical Engineering, SPIE Newsroom, 2006.

Li, Xiaoling et al., "Influence of Duration of Focal Cerebral Ischemia and Neuronal Nitric Oxide Synthase on Translocation of Apoptosis-Inducing Factor to the Nucleus," Neuroscience, Jan. 5, 2007; 144(1): 56-65.

Liang, et al.,: "Photobimodulation Partially Rescues Visual Cortical Neurons from Cyanide-Induced Apoptosis"—Neuroscience 2006;139: 639-649.

Liang, H.L. et al., "Near-Infrared Light Via Light-Emitting Diode Treatment is Therapeutic Against Rotenone- and 1-Methyl-4-Phenylpyridinium Ion-Induced Neurotoxicity," Neuroscience 153 (2008) 936-974.

Liesz, Arthur et al., "Regulatory T cells are key cerebroprotective immunomodulators in acute experimental stroke," Nature Medicine, Jan. 25, 2009.

Lievens, P.O, "The Effect of I.R. Laser Irradiation on the Vasomotricity of the Lymphatic System," Lasers in Medical Science, vol. 5:189, 1991.

Lisman et al. "Two Light-Induced Processes in the Photoreceptor Cells of Limulus Ventral Eyes," The Journal of General Physiology, vol. 58, pp. 544-561, 1971.

Liu, Dong et al., "Activation of Mitochondrial ATP-Dependent Potassium Channels Protects Neurons Against Ischemia-Induced Death by a Mechanism Involving Suppression of Bax Translocation and Cytochrome c Release," Journal of Cerebral Blood Flow & Metabolism, 22:431-443, 2002.

Liu, Timon Cheng-Yi et al., "Cellular rehabilitation of photobiomodulation," Proc. of SPIE, vol. 6534, 2007.

Lo, Eng H, "T time in the brain," Nature Medicine, vol. 15, No. 8, Aug. 2009, pp. 844-846.

Lo, Eng H. et al., "Mechanisms, Challenges and Opportunities in Stroke," Nature Reviews: Neuroscience, vol. 4, May 2003, pp. 399-415.

Lohr, Nicole L. et al., "Enhancement of nitric oxide release from nitrosyl hemoglobin and nitrosyl myoglobin by red/near infrared radiation: Potential role in cardioprotection," Journal of Molecular and Cellular Cardiology 47 (2009) 256-263.

Lopes-Martins, Rodrigo Alvaro Brandão et al, "Steroids block the anti-inflammatory effects of low level laser therapy," Proc. of SPIE, vol. 6140, 2006.

Low-Level Laser Therapy: Compu-Lase, Spectra-Medics Pty Ltd—Low-Level Laser Therapy Specialists, http://www.spectra-medics.com/compulase.html, 1998.

Lubart, Rachel et al., "Broadband Visible Light Induced NO Formation," 2009, http://proceedings.aip.org/proceedings/cpcr.jsp.

Lubart, Rachel et al., "Low-Energy Laser Irradiation Promotes Cellular Redox Activity," Photomedicine and Laser Surgery, vol. 23, No. 1, 2005, pp. 3-9.

Luo, Gang-Yue et al, "Membranotropic photobiomodulation on red blood cell deformability," Proc. of SPIE, vol. 6534, 2007.

Lychagov, V. V., et al.: "Experimental study of cadavers head transmittance", Saratov Fall Meeting 2004: Optical Technologies in Biophysics and Medicine VI, Proc. of SPIE vol. 5771, pp. 328-331.

MacDonald, Loch R. et al., "Pathophysiology of Cerebral Ischemia," Neurol Med Chir (Tokyo) 38, Jan. 1998, pp. 1-11.

(56) References Cited

OTHER PUBLICATIONS

Macklis, Jeffrey D., "Transplanted Neocrotical Neurons Migrate Selectively into Regions of Neuronal Degeneration Produced by Chromophore-targeted Laser Photolysis," The Journal of Neuroscience, Sep. 1993, 13(9); 3848-3863.
Maegawa, Yasuyo et al., "Effects of Near-Infrared Low-Level Laser Irradiation on Microcirculation," Lasers in Surgery and Medicine, 27:427-437 (2000).
Manczak, Maria et al., "Mitochondria are a direct site of Aβ accumulation in Alzheimer's disease neurons: implications for free radical generation and oxidative damage in disease progression," Human Molecular Genetics, 2006, vol. 15, No. 9, pp. 1437-1449.
Marshall, Laura S., "Hope after failure in clinical trials," BusinessScan, BioPhotonics, Apr. 2009.
Martin, Joan B., "Light Activated Tissue Regeneration and Therapy," Notes, Aug. 2004.
Martone, Maryann E. et al., "Modification of Postsynaptic Densities after Transient Cerebral Ischemia: A Quantitative and Three-Dimensional Ultrastructural Study," The Journal of Neuroscience, Mar. 15, 1999, 19(6): 1988-1997.
Mason, Maria G. et al., "Nitric oxide inhibition of respiration involves both competitive (heme) and noncompetitive (copper) binding to cytochrome c oxidase," PNAS, vol. 103, pp. 708-713, Jan. 9, 2006.
Masuhr, F. et al., "Cerebral venous and sinus thrombosis," J. Neurol (2004) 251:11-23.
Matas et al. "Eliminating the Issue of Skin Color in Assessment of the Blanch Response," Advances in Skin & Wound Care, vol. 14 (4, Part 1 of 2), pp. 180-188, Jul./Aug. 2001.
McClelland, Robyn L. et al., "Neurologic Correlates of Infarction-Like Lesion Location on Magnetic Resonance Imaging in the Cardiovascular Health Study," Journal of Stroke and Cerebrovascular Disease, vol. 9, No. 5, Sep.-Oct. 2000; pp. 218-228.
McKinlay, A.F. et al., "Biological Bases of Maximum Permissible Exposure Levels of Laser Standards," J. Soc. Radiol. Prol. 4 (1), 1984.
Meguro, Toshinari et al., "Caspase Inhibitors Attenuate Oxyhemoglobin-Induced Apoptosis in Endothelial Cells," Stroke, 2001; 32; 561-566.
Mester, Endre et al., "The Biomedical Effects of Laser Application," Lasers in Surgery and Medicine, 5:31-39 (1985).
Mirsky, N. et al., "Promotion of Angiogenesis by Low Energy Laser Irradiation," Antioxidants & Redox Signaling, vol. 4, No. 5, 2002, pp. 785-791.
Mitsios, N. et al., "Pathophysiolgy of Acute Ischaemic Stroke: An Analysis of Common Signalling Mechanisms and Identification of New Molecular Targets," Pathobiology 2006; 73:159-175.
Mochizuki-Oda, Noriko et al., "Effects of Near-Infrared Laser on Neural Cell Activity," American Institute of Physics, 2004, pp. 192-195.
Mohanty, Samarendra Kumar et al., "Generation of ROS in cells on exposure to CW and pulsed near-infrared laser tweezers," Photochemical & Photobiological Sciences, 2006, pp. 134-139.
Molinaro, M., "Light/Tissue Interaction IST 8A," Lecture #5, Jan. 23, 2006.
Moncada, Salvador et al., "Nitric oxide, cell bioenergetics and neurodegeneration," Journal of Neurochemistry, 2006, 97, pp. 1676-1689.
Moriyama, Yumi et al., "In Vivo Study of the Inflammatory Modulating Effects of Low-level Laser Therapy on iNOS Expression Using Bioluminescence Imaging," Photochemistry and Photobiology, 2005, 81: 1351-1355.
Moser, Christopher C. et al., "Darwin at the molecular scale: selection and variance in electron tunneling proteins including cytochrome c oxidase," Philosophical Transactions of the Royal Society B, 2006, 361: 1295-1305.
Mthunzi, Patience et al., "Influence of Beam Shape on in-vitro Cellular Transformations in Human Skin Fibroblasts," Proc. of SPIE, vol. 5876, 2005.
Mudra, R. et al., "Analysis of near-infrared spectroscopy and indocyanine green dye dilution with Monte Carlo simulation of light propagation in the adult brain," Journal of Biomedical Optics, 11(4), Jul./Aug. 2006.
Murata, Yoshihiro et al., "Extension of the Thrombolytic Time Window With Minocycline in Experimental Stroke," Stroke, 2008; 39; 3372-3377.
Myers, D.R. et al., "Proposed Reference Spectral Irradiance Standards to Improve Concentrating Photovoltaic System Design and Performance Evaluation," National Renewable Energy Laboratory, May 2002.
Nadareishvili, Zurab et al., "Neural Regeneration after Stroke," The New England Journal of Medicine, 348; 23, Jun. 5, 2003, pp. 2355-2356.
Naviaux, Robert K., "Mitochondria-Light Interactions—Mechanisms of Cell Sparing and Regeneration," The Mitochondrial and Metabolic Disease Center, 2007.
Neumar, Robert W., "Molecular Mechanisms of Ischemic Neuronal Injury," Annals of Emergency Medicine, 35:5, Nov. 2000, pp. 483-506.
Ng, Kwan-Hoong, "Non-Ionizing Radiations—Sources, Biological Effects, Emissions and Exposures," Proceedings of the International Conference on Non-Ionizing Radiation at UNITEN, Electromagnetic Fields and Our Health, Oct. 20-22, 2003.
Nilsson, Thomas, "Photoinduced electron transfer from tris(2,2'-bipyridyl)ruthenium to cytochrome c oxidase," Proc. Natl. Acad. Sci. USA 89 (1992) pp. 6497-6501.
Okada, Eiji et al, "Near-infrared light propagation in an adult head model. II. Effect of superficial tissue thickness on the sensitivity of the near-infrared spectroscopy signal," Applied Optics, Jun. 1, 2003, vol. 42, No. 16, pp. 2915-2922.
Oron, U., et al.: "Low-Energy Laser Irradiation Applied Transcranially 24 Hours Following Induction of Stroke in the Rat Significantly Improves Long-Term Neurological Deficits", The American Stroke Association International Stroke Conference 2005. Stroke. 2005; 399.
Oron, Uri et al.: Low-Level Laser Therapy Applied Transcranially to Rats After Induction of Stroke Significantly Reduces Long-Term Neurological Deficits, Stroke, 2006; 37:2620-2624.
Osipov, A.N. et al., "Biological Activity of Hemoprotein Nitrosyl Complexes," Biochemistry, 2007, vol. 72, No. 13, pp. 1491-1504.
Palacios-Callender, Miriam et al., "Cytochrome c-oxidase regulates endogenous nitric oxide availability in respiring cells: a possible explanation for hypoxic vasodilation," PNAS, Nov. 20, 2007, vol. 104, No. 47, pp. 18508-18513.
Parathath, Susana R. et al., "Nitric Oxide Synthase Isoforms Undertake Unique Roles During Excitotoxicity," Stroke 2007; 38; 1938-1945.
Parihar, Mordhwaj S., "Mitoenergetic failure in Alzheimer disease," Am J Physiol Cell Physiol, 292:8-23, 2007.
Passarella, S., et al.: "Increase in the ADP/ATP Exchange in Rat Liver Mitochondria Irradiated In Vitro by Helium-Neon Laser", Biochemical and BioPhysical Research Communications, vol. 156, No. 2, Oct. 31, 1988, pp. 978-986.
Perez, J. C. et al.: "Transcranial laser therapy for acute ischemic stroke: long-term outcomes of a large single center experience", International Journal of Stroke, pp. 1-23, 2009.
Peterson, Jill et al., "Material Properties of the Human Cranial Vault and Zygoma," The Anatomical Record Part A, 274A:785-797 (2003).
Pislea, Mihaela et al., "Low Level Long Wavelength Laser Irradiation Effects on Cells Cycle Progression and Apoptosis of Energy Restricted Jurkat T-Cells," Romanian J. Biophys., vol. 19, No. 1, pp. 1-18, 2009.
Pogue, BW et al., "Transient absorption changes in vivo during photodynamic therapy with pulsed-laser light," British Journal of Cancer (1999) 80(3/4), pp. 344-351.
Popp, Fritz-Albert, "On the Coherence of Ultraweak Photon Emission from Living Tissues," Disequilibrium and Self-Organisation, pp. 207-230, 1986.
Powers, William J. et al., "Cerebral mitochondrial metabolism in early Parkinson's disease," Journal of Cerebral Blood Flow & Metabolism (2008) 28, 1754-1760.

(56) References Cited

OTHER PUBLICATIONS

Ratner, Mark L., "The Alzheimer's Divide," In Vivo, Sep. 2008.
Regulatory Insight Inc., "Tuco Erchonia PL2000," Premarket Notification, 2001.
Respond 2400 Laser Therapy System, http://www.nmia.com/~pegasus/las2400.html, Accessed Nov. 3, 1998.
Respond Systems, Inc., "Understanding Low Level Laser Therapy," 1991.
Reznikov, L.L. et al., "The Biomechanism of Low-Energy Laser Irradiation is Similar to General Adaptive Reaction," Proc. SPIE, vol. 2086, 380 (1994).
Rochkind, S. et al., "New trend in neuroscience: Low-power laser effect on peripheral and central nervous system (basic science, preclinical and clinical studies)," Neurological Research, vol. 14, Mar. 1992, pp. 2-11.
Rohn, Troy T. et al., "Caspases as Therapeutic Targets in Alzheimer's Disease: Is it Time to 'Cut' to the Chase?" Int J Clin Exp Pathol (2009) 2, pp. 108-118.
Rojas, Santiago et al., "Modest MRI Signal Intensity Changes Precede Delayed Cortical Necrosis After Transient Focal Ischemia in the Rat," Stroke 2006; 37; 1525-1532.
Rose, Andreas et al., "Mode Field Pertubations and Numerical Aperture Broadening Due to Angular Misalignment in Multimode Fiber Coupling," Proc. of SPIE, vol. 7173, 2009.
Rossi, David J. et al., "Astrocyte metabolism and signaling during brain ischemia," Nature Neuroscience, vol. 10, No. 11, Nov. 2007, pp. 1377-1386.
Samosiuk et al., "Magnetic and laser therapy of acute ischemic stroke," Vopr Kurortol Fizioter Lech Fiz Kult, English Abstract accessed on Nov. 9, 2004 from Medscape from WebMD, Mar.-Apr. 2003; (2):19-20.
Sarasa, Manuel et al., "Natural Non-Transgenic Animal Models for Research in Alzheimer's Disease," Current Alzheimer's Research, 2009, 6, pp. 171-178.
Savio Chan, C. et al., "Rejuvenation' protects neurons in mouse models of Parkinson's disease," Nature, vol. 447, Jun. 28, 2007.
Schaffer, Chris B. et al., "Two-Photon Imaging of Cortical Surface Microvessels Reveals a Robust Redistribution in Blood Flow after Vascular Occlusion," PLOS Biology, Feb. 2006, vol. 4, Issue 2, pp. 0258-0270.
Scheele, Jürgen S. et al., "Kinetics of NO Ligation with Nitric-oxide Synthase by Flash Photolysis and Stopped-flow Spectrophotometry," The Journal of Biological Chemistry, vol. 274, No. 19, May 1999, pp. 13105-13110.
Schinzel, Anna C. et al., "Cyclophilin D is a component of mitochondrial permeability transition and mediates neuronal cell death after focal cerebral ischemia," PNAS, Aug. 23, 2005, vol. 102, No. 34, pp. 12005-12010.
Schurr, Avital, "Lactate: the ultimate cerebral oxidative energy substrate?" Journal of Cerebral Flood Flow & Metabolism (2006) 26, 142-152.
Seremet, Teofila et al., "Photobiomodulation of Quercetin Antiproliferative Effects Seen in Human Acute Leukemia Jurkat Cells," Romanian J. Biophys., vol. 17, No. 1, pp. 33-43, 2007.
Sharma, Jagdish C. et al., "N-terminal proBrain Natriuretic Peptide Levels Predict Short-term Poststroke Survival," Journal of Stroke and Cerebrovascular Disease, vol. 15, No. 3 (May-Jun.), 2006: pp. 121-127.
Sharpe, Martyn A., "Interaction of Peroxynitrite with Mitochondrial Cytochrome Oxidase," The Journal of Biological Chemistry, vol. 273, No. 47, Nov. 20, 1998, pp. 30961-30972.
Shichita, Takashi et al., "Pivotal role of cerebral interleukin-17-producing γσT cells in the delayed phase of ischemic brain injury," Nature Medicine, vol. 15, No. 8, Aug. 2009, pp. 946-951.
Shimada, Sachihiro et al., "Intracellular disruption of mitochondria in a living HeLa cell with 76-MHz femtosecond laser oscillator," Optics Express, vol. 13, No. 24, Nov. 28, 2005, pp. 9869-9880.
Shiva, Struti, "Shining a light on tissue NO stores: Near infrared release of NO from nitrite and nitrosylated hemes," Journal of Molecular and Cellular Cardiology, 46, 2009, pp. 1-3.
Sieron, A. et al., "Our Own Experience in Clinical Use of Low Power Laser Therapy," Przegl Lek, 1995; 52(1):13-5.
Sim-Med Ltd, Laser Therapy Manufacturers, www.therapylaser.com, date unknown.
Sims, Neil R., "Mitochondrial contributions to tissue damage in stroke," Neurochemistry International, 40 (2002), pp. 511-526.
Singhal, Aneesh et al., "Advances in Emerging Nondrug Therapies for Acute Stroke 2007," Stroke, Advances in Stroke 2007, Feb. 2008, pp. 289-291.
Siposan, Dan G. et al., "Effect of Low-Level Laser Radiation on Some Rheological Factors in Human Blood: An in Vitro Study," Journal of Clinical Laser Medicine & Surgery, vol. 18, No. 4, 2000, pp. 185-195.
Smith, Rich, "Seeing The Light: How light therapy is surprising skeptics and gaining converts," Physical Therapy Products, Apr./May 2004.
Snyder, S.K., et al., "Quantitation of calcitonin gene-related peptide mRNA and neuronal cell death in facial motor nuclei following axotomy and 633 nm low power laser treatment," Surg. Med., 31:216-222 (2002).
Soane, Lucian et al., "Mechanisms of Impaired Mitochondrial Energy Metabolism in Acute and Chronic Neurodegenerative Disorders," J. Neurosci. Res., Nov. 15, 2007; 85(15): 3407-3415.
Sofiano Bros Ltd., Medical Laser, date unknown.
Sommer, A, et al., "Biostimulatory Windows in Low-Intensity Laser Activation: Lasers, Scanners, and NASA's Light-Emitting Diode Array System," Journal of Clinical Laser Medicine & Surgery, vol. 19, No. 1, 2001, pp. 29-33.
Stoll, Christian et al., "Quantum Dots on Gold: Electrodes for Photoswitchable Cytochrome c Electrochemistry," Small Journal, 2006, vol. 2, No. 6, pp. 741-743.
Stopp, Sebastian et al., "A new concept for navigated laser surgery," Laser Med. Sci. (2008) 23:261-266.
Streeter, J., et al., "Mechanisms of action of light therapy for stroke and acute myocardial infarction," Mitochondrion 4:569-576 (2004).
Sudlow, C.L.M. et al., "Comparable Studies of the Indicidence of Stroke and its Pathological Types," Stroke, 1997; 28; 491-499.
Sukstanskii, A.L. et al., "An analytical model of temperature regulation in human head," Journal of Thermal Biology, 29 (2004), pp. 583-587.
Sun, Miao-Kun et al., "Postroke neuronal rescue and synaptogenesis mediated in vivo by protein kinase C in adult brains," PNAS, Sep. 9, 2008, vol. 105, No. 36, pp. 13620-13625.
Super Lizer™, Spot Type Polarized Light Therapy Equipment Model HA-550, Tokyo Iken Co., Ltd. (date unknown).
Szundi, Istvan et al., "Flash-Photolysis of Fully Reduced and Mixed-Valence CO-Bound Rhodobacter sphaeroides Cytochrome c Oxidase: Heme Spectral Shifts," Biochemistry, 2007, 46, 12567-12578.
Tafur, Joseph et al., "Low-Intensity Light Therapy: Exploring the Role of Redox Mechanisms," Photomedicine and Laser Surgery, vol. 26, No. 4, 2008.
Tajima, H. et al., "A light-emitting diode fabricated from horse-heart cytochrome c," Solid State Communications, 126 (2003) 579-581.
The Laser Exchange, "LEDS," http://laser.uk.com/tech/index.html, Accessed Jan. 24, 2000 (p. 1 missing).
Theralase Inc., "Low Level Light Therapy (LLLT)," 1999.
Theralase Inc., "Therapeutic Lasers," date unknown.
Theralase Inc., "Therapeutic Medical Laser Summary," date unknown.
Therapeutic Laser Corporation, "Healing Light Healing the World," website unknown, Accessed Jul. 1, 1999.
Thor Models LX, DDII & DD, Accessed Jul. 1, 1999.
Trimmer, Patricia A. et al., "Mitochondrial abnormalities in cybrid cell models of sporadic Alzheimer's disease worsen with passage in culture," Neurobiology of Disease, vol. 15, 2004, pp. 29-39.
Trimmer, Patricia A. et al., "Parkinson's disease transgenic mitochondrial cybrids generate Lewy inclusion bodies," Journal of Neurochemistry, (2004) 88, pp. 800-812.
Trimmer, Patricia A. et al., "Reduced axonal transport in Parkinson's disease cybrid neurites is restored by light therapy," Molecular Neurodegeneration 2009, 4:26.

(56) References Cited

OTHER PUBLICATIONS

Trimmer, Patricia A., "Abnormal Mitochondrial Morphology in Sporadic Parkinson's and Alzheimer's Disease Cybrid Cell Lines," Experimental Neurology, 162, 37-50 (2000).
Troy, Tamara L. et al., "Optical Properties of Human Skin in the NIR Wavelength Range of 1000-2200nm," Instrumental Metrics, Inc. (2001).
Tuchin, V., Optical Properties of Tissues With Strong (Multiple) Scattering, Tissue Optics, Light Scattering Methods and Instruments for Medical Diagnosis, SPIE Press, Bellingham, WA 2000 (2000), pp. 3-11.
Tunér, Jan et al., "It's All in the Parameters: A Critical Analysis of Some Well-Known Negative Studies on Low-Level Laser Therapy," Journal of Clinical Laser Medicine & Surgery, vol. 16, No. 5, 1998, pp. 245-248.
Vakoc, Benjamin J. et al., "Real-time microscopic visualization of tissue response to laser thermal therapy," Journal of Biomedical Optics, Mar./Apr. 2007, vol. 12(2).
van der Worp, H.B. et al., "Complications of Acute Ischaemic Stroke," Cerebrovascular Disease, 1998; 8:124-132.
Verkruysse, Wim et al., "Infrared Measurement of Human Skin Temperature to Predict the Individual Maximum Safe Radiant Exposure (IMSRE)," Lasers in Surgery and Medicine, 39:757-766, 2007.
Villringer, Arno et al., "Non-invasive optical spectroscopy and imaging of human brain function," TINS vol. 20, No. 10, 1997.
Vladimirov, Yu. A. et al., "Molecular and Cellular Mechanisms Triggered by Low-level Laser Irradiation," Biophysics, vol. 49, No. 2, 2004, pp. 325-336.
Vladimirov, Yu. A. et al., "Photobiological Principles of Therapeutic Applications of Laser Radiation," Biochemistry (Moscow), vol. 69, No. 1, 2004, pp. 81-90.
Walz, Birgit et al., "Prognosis of patients after hemicraniectomy in malignant middle cerebral artery infarction," J. Neurol. (2002) 249: 1183-1190.
Wang, Xinglong et al., "The Role of Abnormal Mitochondrial Dynamics in the Pathogenesis of Alzheimer's Disease," J Neurochem, May 2009 109 (Suppl 1): 153-159.
Waynant, R., et al., "Review of Laser Therapy: Current Status and Consensus for Research Needed for Further Progress," NAALT Conference 2003.
Wei, Ling et al., "Collateral Growth and Angiogenesis Around Cortical Stroke," Stroke, Sep. 2001, pp. 2179-2184.
Wells, Jonathan et al., "Biophysical Mechanisms of Transient Optical Stimulation of Peripheral Nerve," Biophysical Journal, vol. 93, Oct. 2007, pp. 2567-2580.
Williams, R. Rhys et al., "Incidence and Occurrence of Total (First-Ever and Recurrent) Stroke," Stroke, Dec. 1999, pp. 2523-2528.
Willis, Gregory L., "Intraocular microinjections repair experimental Parkinsons' disease," Brain Research 1217 (2008) 119-131.
Wong-Riley, et al.: "Photobiomodulation Directly Benefits Primary Neurons Functionally Inactivated by Toxins", The Journal of Biological Chemistry—2005;280(6): 4761-4771.
Xing, Bianzhi et al., "Ischemic Postconditioning Inhibits Apoptosis After Focal Cerebral Ischemic/Reperfusion Injury in the Rat." Stroke, Aug. 2008, pp. 2362-2369.
Xu, Lijun et al., "Overexpression of mitochondrial Hsp70/Hsp75 in rat brain protects mitochondria, reduces oxidative stress, and protects from focal ischemia," Journal of Cerebral Blood Flow & Metabolism (2009) 29, 365-374.
Yang, Fu-Shou, "Medical Applications of Low Power Lasers in China," Laser Systems for Photobiology and Photomedicine, 1991, pp. 115-127.

Yaroslaysky, A. N. et al., "Optical properties of selected native and coagulated human brain tissues in vitro in the visible and near infrared spectral range," Physics in Medicine and Biology, 47 (2002), pp. 2059-2073.
Yi, Muqing et al., "Control of mitochondrial motility and distribution by the calcium: a homeostatic circuit," The Journal of Cell Biology, vol. 167, Nov. 22, 2004, pp. 661-672.
Yin, Xiao-Ming et al., "Bid-mediated Mitochondrial Pathway is Critical to Ischemic Neuronal Apoptosis and Focal Cerebral Ischemia," The Journal of Biological Chemistry, vol. 277, No. 44, Nov. 1, 2002, pp. 42074-42081.
Yip, Samuel et al., "Laser therapy in acute stroke treatment," New Therapies, International Journal of Stroke, vol. 3, May 2008, pp. 88-91.
Young, A.E.R. et al., "Behaviour of near-infrared light in the adult human head: implications for clinical near-infrared spectroscopy," British Journal of Anaesthesia, 84 (1): 38-42 (2000).
Yujung, Kang et al., "Development of the fully automated program system; Can calculate transporting light intensity to the specific position in the brain tissue," http://pbil.kaist.ac.kr/lectures/bis500/report/proposal/team3_proposal_final.doc, accessed Apr. 30, 2007.
Zeischegg, Peter M., "Low Level Laser Therapy (LLLT)," http://www.drz.org/laser.htm, Accessed Oct. 1, 1999.
Zenzie et al. "Evaluation of Cooling Methods for Laser Dermatology," Lasers in Surgery and Medicine, 26:130-144 (2000).
Zhang, Rong et al., "Near infrared light protects cardiomyocytes from hypoxia and reoxygenation injury by a nitric oxide dependent mechanism," Journal of Molecular and Cellular Cardiology, 46 (2009) pp. 4-14.
Zheng, Zhen et al., "Cellular and Molecular Events Underlying Ischemia-Induced Neuronal Apoptosis," Drug News Perspect., 16(8), Oct. 2003, pp. 497-503.
Zivin, Justin A., et al.: "Effectiveness and Safety of Transcranial Laser Therapy for Acute Ischemic Stroke", Journal of the American Stroke Association, published on line Feb. 20, 2009, pp. 1-7.
Stokes et al. "Categorical Data Analysis Using the SAS System 2nd Edition," 2000, NC: SAS Institute, Inc.
Belevich et al.: "Exploring the proton pump mechanism of cytochrome c oxidase in real time", Proc. Nat'l Acad. Sci., Feb. 20, 2007, 104(8)2685-2690.
Belevich et al.: "Proton-coupled electron transfer drives the proton pump of cytochrome c oxidase", Nature, Apr. 2006, 440:829-832.
Burton et al.: "Relation Between Blood Pressure and Flow in the Human Forearm", J. Appl. Physiology, Nov. 1951, 4(5):329-339.
Janssen et al.: "Modeling of temperature and perfusion during scalp cooling", Phys. Med. Biol., Aug. 18, 2005, 50(18)4065-4073.
Lapchak: "Neuroprotective effects of the spin trap agent disodium-[(tert-butylimino)methyl]benzene-1,3-disulfonate N-oxide (generic NXY-059) in a rabbit small clot embolic stroke model: combination studies with the thrombolytic tissue plasminogen activator", Stroke, May 2002, 33(5):1411-1415
Lepselter et al.: "Biological and clinical aspects in laser hair removal", J. Dermatological Treatment, Apr. 1, 2004, 15(2):72-83.
Niitsuma et al.: "Experimental study of decubitus ulcer formation in the rabbit ear lobe", J. of Rehab. Res. and Dev., Jan. 1, 2003, 40(1):67-72.
Oron et al.: "Low-Level Laser Therapy Applied Transcranially to Mice following Traumatic Brain Injury Significantly Reduces Long-Term Neurological Deficits", Journal of Neurotrauma, Nov. 4, 2007 24(4):651-656.
Sommer et al.: "Stressed cells survive better with light", J. Proteome. Res., Oct. 1, 2002, 1(5):475.
Wells et al.: "Biophysical mechanisms responsible for pulsed low-level laser excitation of neural tissue", Proc. SPIE, vol. 6084, 2006, pp. 60840X.

\* cited by examiner

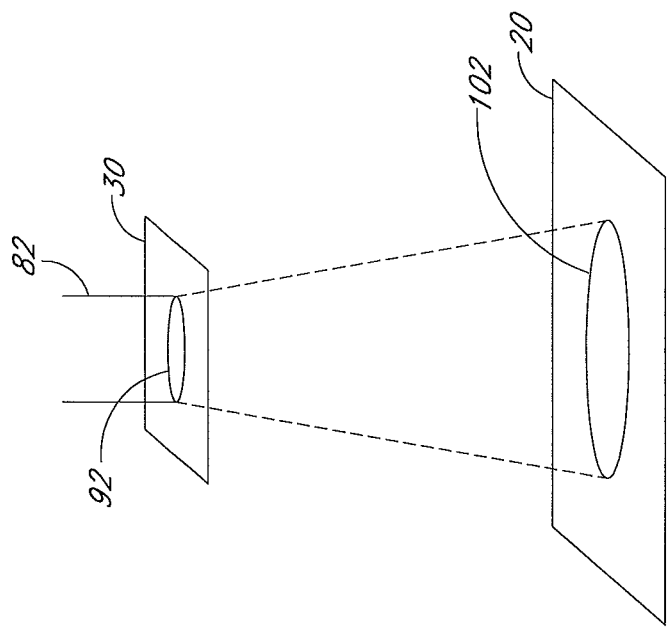
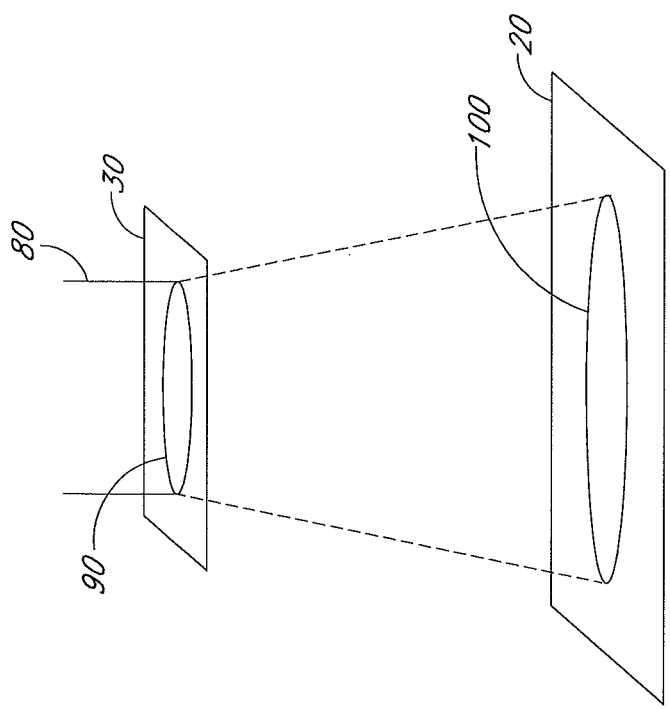
FIG. 8B
FIG. 8A

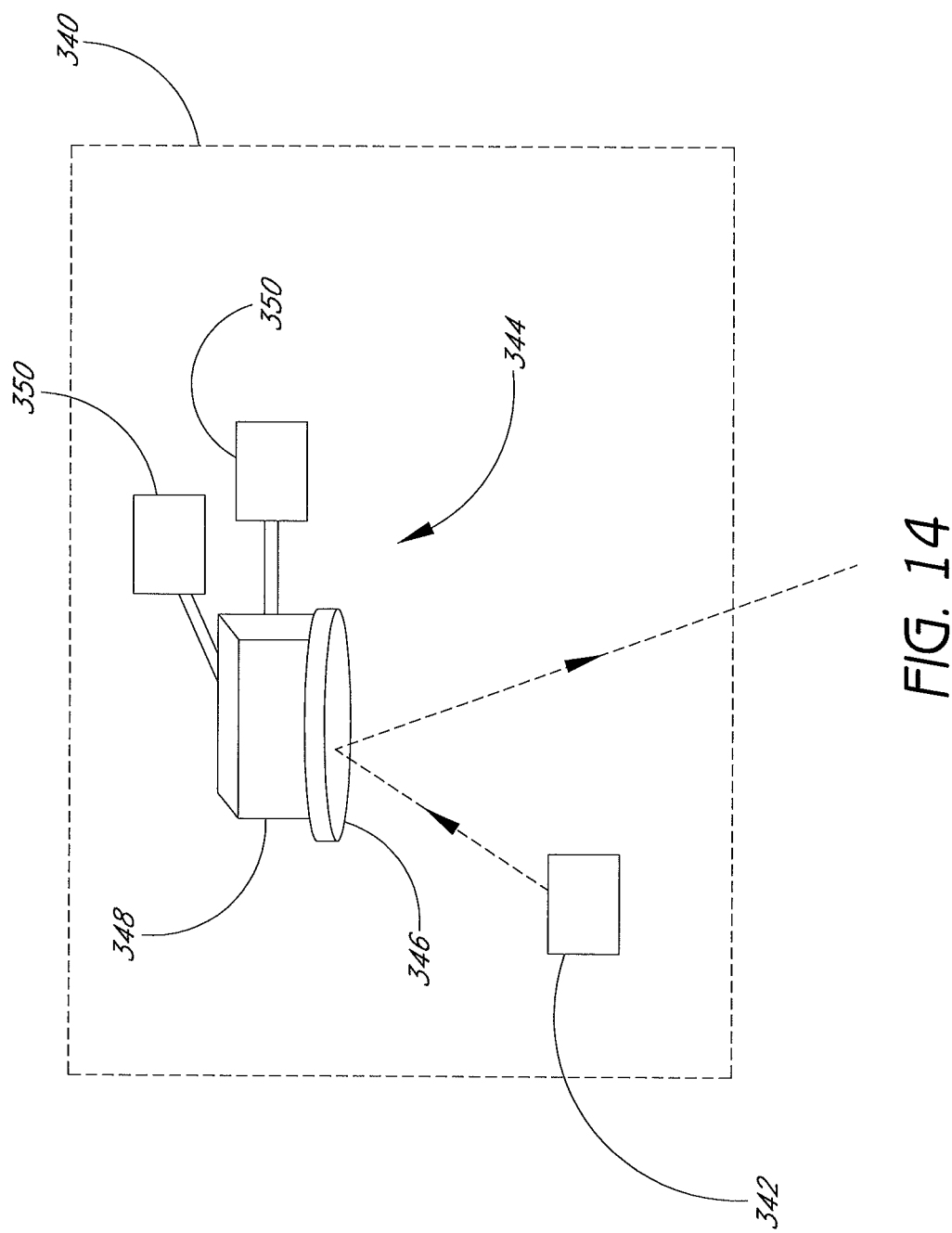

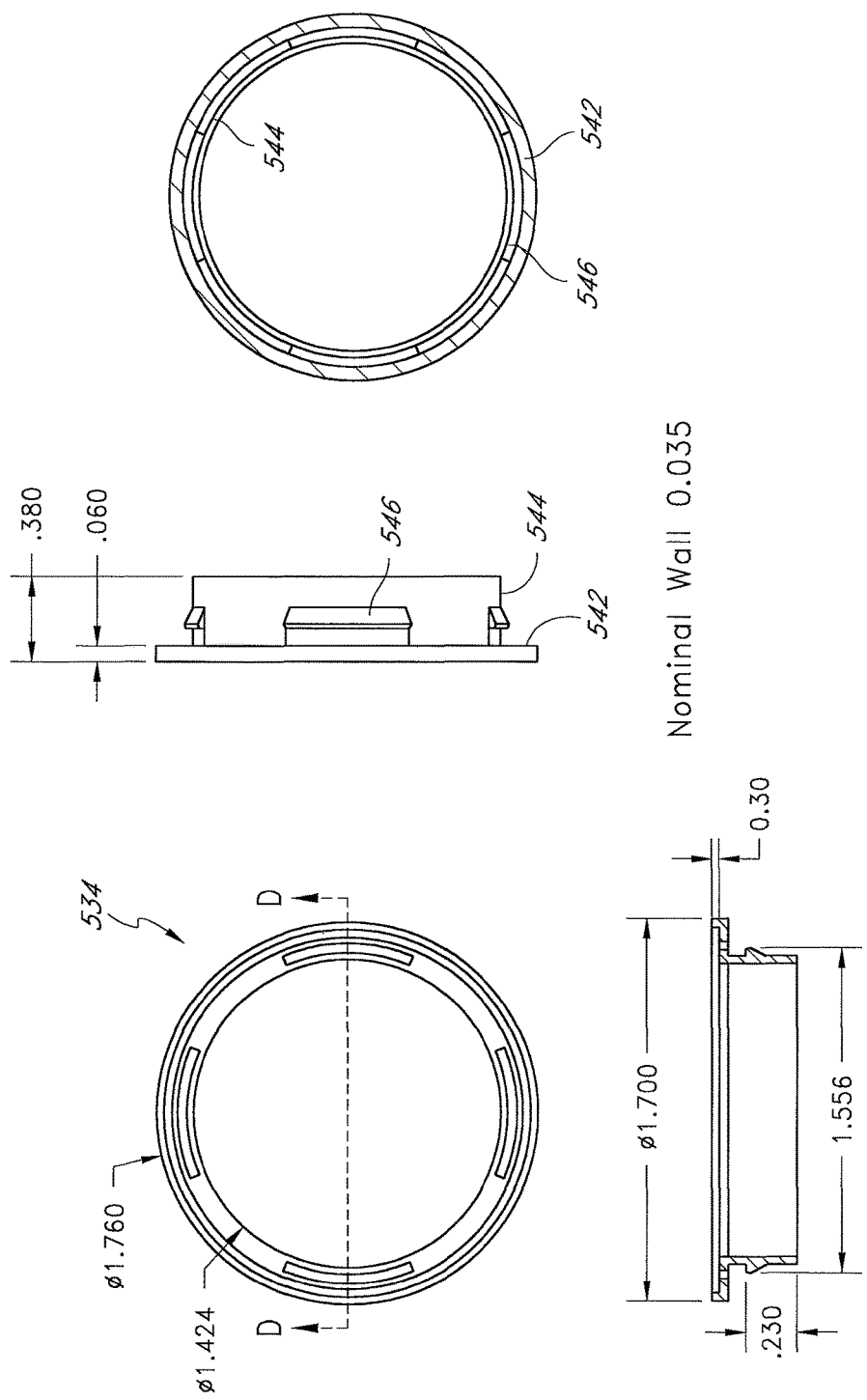

LIGHT-EMITTING DEVICE AND METHOD FOR PROVIDING PHOTOTHERAPY TO THE BRAIN

CLAIM OF PRIORITY

This application is a continuation from U.S. patent application Ser. No. 11/385,988, filed Mar. 21, 2006, which is incorporated in its entirety by reference herein, and which claims the benefit of U.S. Provisional Application No. 60/763,261, filed Jan. 30, 2006, which is incorporated in its entirety by reference herein.

BACKGROUND OF THE INVENTION

Field of the Invention

The present invention relates in general to phototherapy, and more particularly, to novel apparatuses and methods for phototherapy of brain tissue affected by stroke.

Description of the Related Art

Stroke, also called cerebrovascular accident (CVA), is a sudden disruption of blood flow to a discrete area of the brain that is brought on by a clot lodging in an artery supplying that area of that brain, or by a cerebral hemorrhage due to a ruptured aneurysm or a burst artery. The consequence of stroke is a loss of function in the affected brain region and concomitant loss of bodily function in areas of the body controlled by the affected brain region. Depending upon the extent and location of the primary insult in the brain, loss of function varies greatly from mild or severe, and may be temporary or permanent. Lifestyle factors such as smoking, diet, level of physical activity and high cholesterol increase the risk of stroke, and thus stroke is a major cause of human suffering in developed nations. Stroke is the third leading cause of death in most developed nations, including the United States.

Until recently, stroke treatment was restricted to providing basic life support at the time of the stroke, followed by rehabilitation. Recently, new drug therapies have taken the approach of breaking up blood clots or protecting surviving at-risk neurons from further damage.

Thrombolytic therapy includes aspirin or intravenous heparin to prevent further clot formation and to maintain blood flow after an ischemic stroke. Thrombolytic drugs include tissue plasminogen activator (TPA) and genetically engineered versions thereof, and streptokinase. However, streptokinase does not appear to improve the patient's outlook unless administered early (within three hours of stroke). TPA when administered early appears to substantially improve prognosis, but slightly increases the risk of death from hemorrhage. In addition, over half of stroke patients arrive at the hospital more than three hours after a stroke, and even if they arrive quickly, a CT scan must first confirm that the stroke is not hemorrhagic, which delays administration of the drug. Also, patients taking aspirin or other blood thinners and patients with clotting abnormalities should not be given TPA.

Neuroprotective drugs target surviving but endangered neurons in a zone of risk surrounding the area of primary infarct. Such drugs are aimed at slowing down or preventing the death of such neurons, to reduce the extent of brain damage. Certain neuroprotective drugs are anti-excitotoxic, i.e., work to block the excitotoxic effects of excitatory amino acids such as glutamate that cause cell membrane damage under certain conditions. Other drugs such as citicoline work by repairing damaged cell membranes. Lazaroids such as Tirilazed (Freedox) counteract oxidative stress produced by oxygen-free radicals produced during stroke. Other drugs for stroke treatment include agents that block the enzyme known as PARP, and calcium-channel blockers such as nimodipine (Nimotop) that relax the blood vessels to prevent vascular spasms that further limit blood supply. However, the effect of nimodipine is reduced if administered beyond six hours after a stroke and it is not useful for ischemic stroke. In addition, drug therapy includes the risk of adverse side effects and immune responses.

Surgical treatment for stroke includes carotid endarterectomy, which appears to be especially effective for reducing the risk of stroke recurrence for patients exhibiting arterial narrowing of more than 70%. However, endarterectomy is highly invasive, and risk of stroke recurrence increases temporarily after surgery. Experimental stroke therapies include an angiography-type or angioplasty-type procedure using a thin catheter to remove or reduce the blockage from a clot. However, such procedures have extremely limited availability and increase the risk of embolic stroke. Other surgical interventions, such as those to repair an aneurysm before rupture remain controversial because of disagreement over the relative risks of surgery versus leaving the aneurysm untreated.

Against this background, a high level of interest remains in finding new and improved therapeutic apparatuses and methods for the treatment of stroke. In particular, a need remains for relatively inexpensive and non-invasive approaches to treating stroke that also avoid the limitations of drug therapy.

SUMMARY OF THE INVENTION

In certain embodiments, an apparatus is provided for irradiating at least a portion of a patient's brain with electromagnetic radiation to treat stroke, Parkinson's Disease, Alzheimer's Disease, or depression. The apparatus comprises a source of the electromagnetic radiation, the electromagnetic radiation having at least one wavelength in a range between about 780 nanometers and about 840 nanometers. The apparatus further comprises an output optical element comprising sapphire and comprising a surface configured to be in thermal communication with the patient's body. The apparatus further comprises a thermoelectric cooler thermally coupled to the output optical element and configured to remove heat from the output optical element and to actively cool an irradiated portion of the patient's body. The apparatus further comprising a heat sink thermally coupled to the thermoelectric cooler, wherein the heat sink is positioned so that the electromagnetic radiation from the source propagates through the heat sink and through the output optical element.

In certain embodiments, an apparatus is provided for irradiating at least a portion of a patient's brain with electromagnetic radiation to treat stroke, Parkinson's Disease, Alzheimer's Disease, or depression. The apparatus comprises a source of the electromagnetic radiation. The apparatus further comprises an output optical element comprising a rigid and substantially thermally conductive material and a surface configured to be in thermal communication with the patient's body. The apparatus further comprises a cooler thermally coupled to the output optical element to remove heat from the output optical element. The apparatus further comprises a heat sink thermally coupled to the cooler, wherein the heat sink is positioned so that the electromagnetic radiation from the source propagates through the heat sink and through the output optical element.

In certain embodiments, an apparatus is provided for irradiating at least a portion of a patient's brain with electromagnetic radiation to treat stroke, Parkinson's Disease, Alzheimer's Disease, or depression. The apparatus comprises a source of the electromagnetic radiation. The apparatus further comprises an output optical element comprising a rigid and substantially thermally conductive material and configured to be in thermal communication with the patient's body. The apparatus further comprises at least one switch electrically coupled to the source, the at least one switch configured to be actuated by pressing the output optical element against a surface. The source is responsive to the at least one switch by emitting light only when the at least one switch is actuated.

For purposes of summarizing the present invention, certain aspects, advantages, and novel features of the present invention have been described herein above. It is to be understood, however, that not necessarily all such advantages may be achieved in accordance with any particular embodiment of the present invention. Thus, the present invention may be embodied or carried out in a manner that achieves or optimizes one advantage or group of advantages as taught herein without necessarily achieving other advantages as may be taught or suggested herein.

BRIEF DESCRIPTION OF THE DRAWINGS

FIGS. 8A and 8B schematically illustrate two light beams having different cross-sections impinging a patient's scalp and propagating through the patient's head to irradiate a portion of the patient's brain tissue.

FIG. 14 schematically illustrates a light source comprising a laser diode and a galvometer with a mirror and a plurality of motors.

FIG. 23 schematically illustrates an example first support ring with example dimensions in inches.

DETAILED DESCRIPTION OF THE PREFERRED EMBODIMENT

Low level light therapy ("LLLT") or phototherapy involves therapeutic administration of light energy to a patient at lower power outputs than those used for cutting, cauterizing, or ablating biological tissue, resulting in desirable biostimulatory effects while leaving tissue undamaged. In non-invasive phototherapy, it is desirable to apply an efficacious amount of light energy to the internal tissue to be treated using light sources positioned outside the body. (See, e.g., U.S. Pat. No. 6,537,304 to Oron and U.S. patent application Ser. No. 10/353,130, both of which are incorporated in their entireties by reference herein.)

Laser therapy has been shown to be effective in a variety of settings, including treating lymphoedema and muscular trauma, and carpal tunnel syndrome. Recent studies have shown that laser-generated infrared radiation is able to penetrate various tissues, including the brain, and modify function. In addition, laser-generated infrared radiation can induce angiogenesis, modify growth factor (transforming growth factor-β) signaling pathways, and enhance protein synthesis.

However, absorption of the light energy by intervening tissue can limit the amount of light energy delivered to the target tissue site, while heating the intervening tissue. In addition, scattering of the light energy by intervening tissue can limit the power density or energy density delivered to the target tissue site. Brute force attempts to circumvent these effects by increasing the power and/or power density applied to the outside surface of the body can result in damage (e.g., burning) of the intervening tissue.

Non-invasive phototherapy methods are circumscribed by setting selected treatment parameters within specified limits so as to preferably avoid damaging the intervening tissue. A review of the existing scientific literature in this field would cast doubt on whether a set of undamaging, yet efficacious, parameters could be found. However, certain embodiments, as described herein, provide devices and methods which can achieve this goal.

Such embodiments may include selecting a wavelength of light at which the absorption by intervening tissue is below a damaging level. Such embodiments may also include setting the power output of the light source at very low, yet efficacious, power densities (e.g., between approximately 100 μW/cm$^2$ to approximately 10 W/cm$^2$) at the target tissue site, and time periods of application of the light energy at a few seconds to minutes to achieve an efficacious energy density at the target tissue site being treated. Other parameters can also be varied in the use of phototherapy. These other parameters contribute to the light energy that is actually delivered to the treated tissue and may play key roles in the efficacy of phototherapy. In certain embodiments, the irradiated portion of the brain can comprise the entire brain.

Element to Inhibit Temperature Increases at the Scalp

Figure 1:
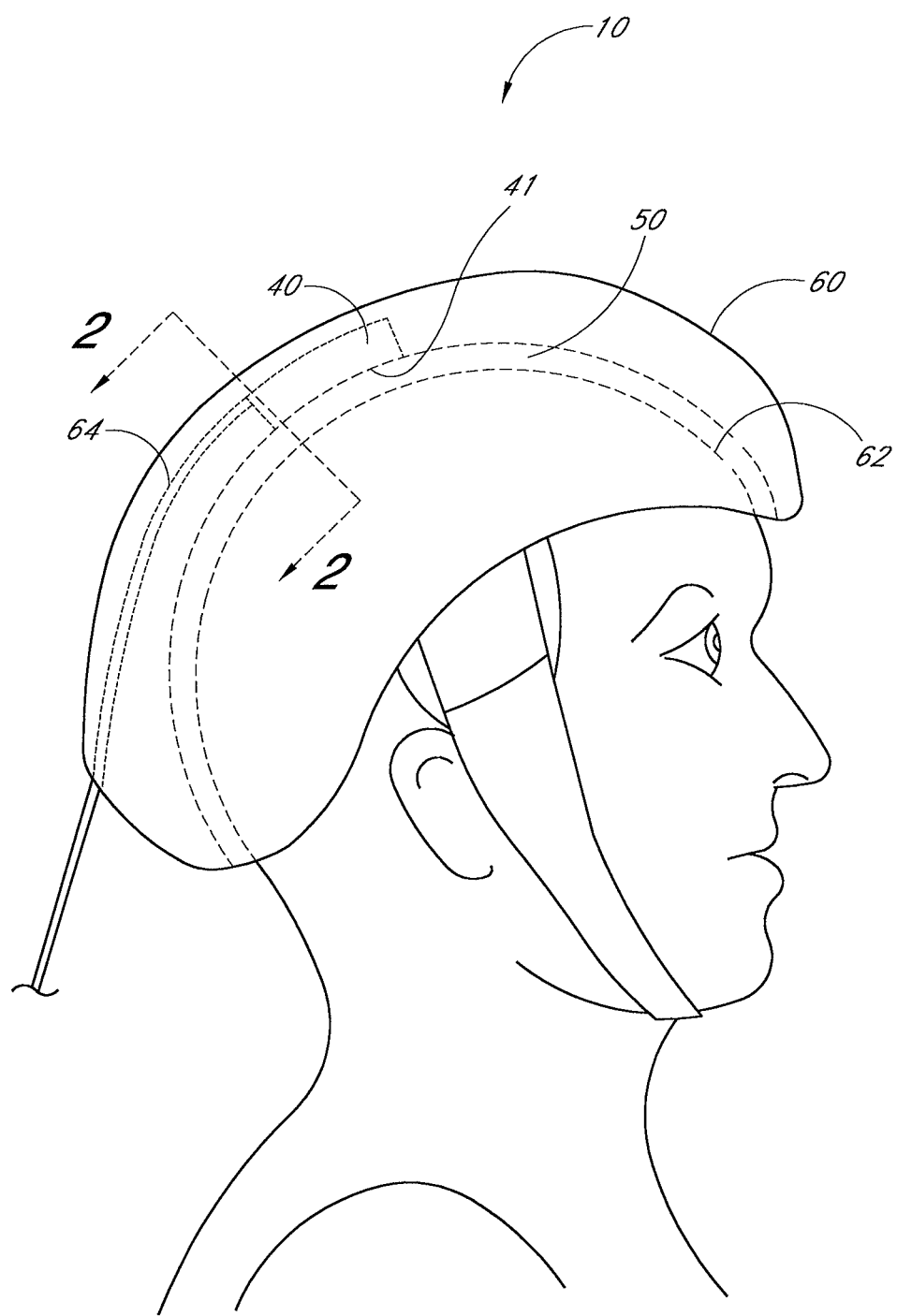
FIG. 1 schematically illustrates a therapy apparatus comprising a cap which fits securely over the patient's head.
Figure 2:
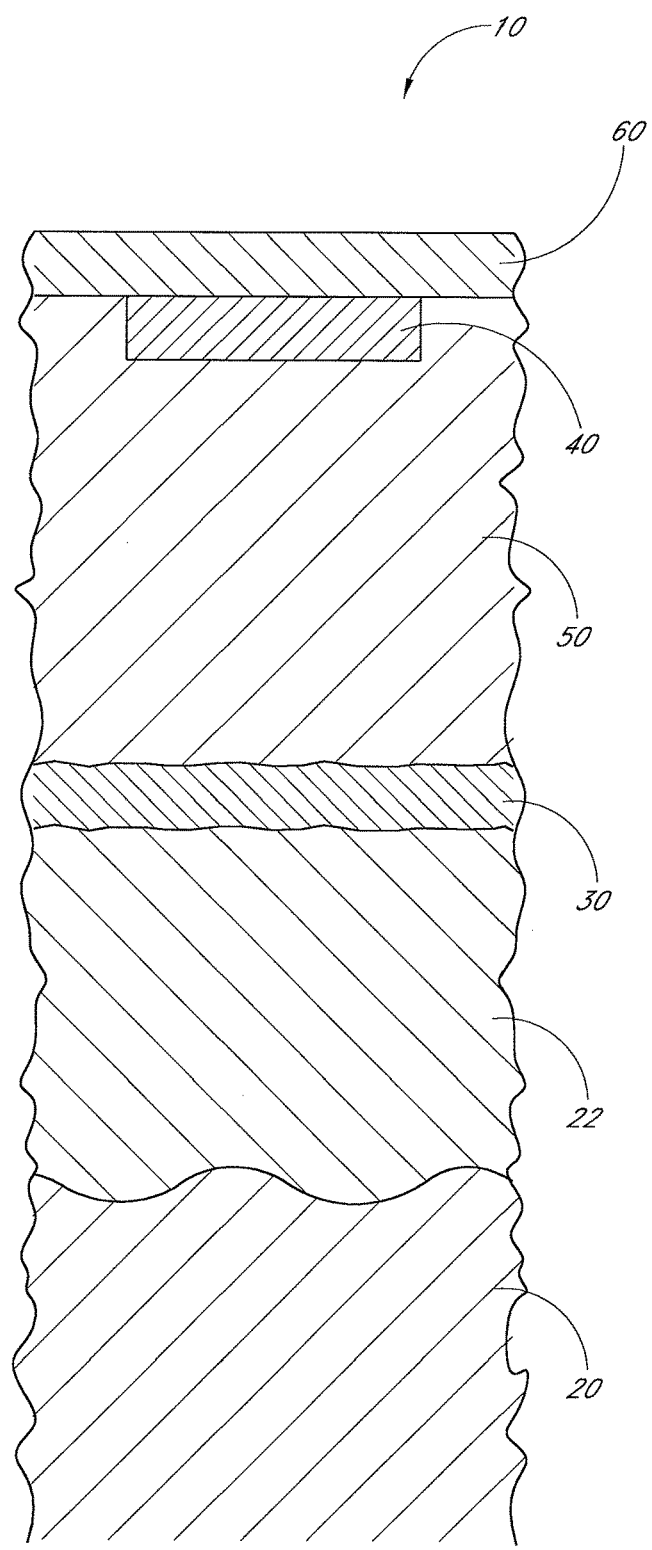
FIG. 2 schematically illustrates a fragmentary cross-sectional view taken along the lines 2-2 of FIG. 1, showing one embodiment of a portion of a therapy apparatus comprising an element and its relationship to the scalp and brain.

FIGS. 1 and 2 schematically illustrate an embodiment of a therapy apparatus 10 for treating a patient's brain 20. The therapy apparatus 10 comprises a light source 40 having an output emission area 41 positioned to irradiate a portion of the brain 20 with an efficacious power density and wavelength of light. The therapy apparatus 10 further comprises an element 50 interposed between the light source 40 and the patient's scalp 30. The element 50 is adapted to inhibit temperature increases at the scalp 30 caused by the light.

As used herein, the term "element" is used in its broadest sense, including, but not limited to, as a reference to a constituent or distinct part of a composite device. In certain embodiments, the element 50 is adapted to contact at least a portion of the patient's scalp 30, as schematically illustrated in FIGS. 1-4. In certain such embodiments, the element 50 is in thermal communication with and covers at least a portion of the scalp 30. In other embodiments, the element 50 is spaced away from the scalp 30 and does not contact the scalp 30.

In certain embodiments, the light passes through the element 50 prior to reaching the scalp 30 such that the element 50 is in the optical path of light propagating from the light source 40, through the scalp 30, through the bones, tissues, and fluids of the head (schematically illustrated in FIG. 1 by the region 22), to the brain 20. In certain embodiments, the light passes through a transmissive medium of the element 50, while in other embodiments, the light passes through an aperture of the element 50. As described more fully below, the element 50 may be utilized with various embodiments of the therapy apparatus 10.

In certain embodiments, the light source 40 is disposed on the interior surface of a cap 60 which fits securely over the patient's head. The cap 60 provides structural integrity for the therapy apparatus 10 and holds the light source 40 and element 50 in place. Example materials for the cap 60 include, but are not limited to, metal, plastic, or other materials with appropriate structural integrity. The cap 60 may include an inner lining 62 comprising a stretchable fabric or mesh material, such as Lycra or nylon. In certain embodiments, the light source 40 is adapted to be removably attached to the cap 60 in a plurality of positions so that the output emission area 41 of the light source 40 can be advantageously placed in a selected position for treatment of a stroke or CVA in any portion of the brain 20. In other embodiments, the light source 40 can be an integral portion of the cap 60.

The light source 40 illustrated by FIGS. 1 and 2 comprises at least one power conduit 64 coupled to a power source (not shown). In some embodiments, the power conduit 64 comprises an electrical conduit which is adapted to transmit electrical signals and power to an emitter (e.g., laser diode or light-emitting diode). In certain embodiments, the power conduit 64 comprises an optical conduit (e.g., optical waveguide) which transmits optical signals and power to the output emission area 41 of the light source 40. In certain such embodiments, the light source 40 comprises optical elements (e.g., lenses, diffusers, and/or waveguides) which transmit at least a portion of the optical power received via the optical conduit. In still other embodiments, the therapy apparatus 10 contains a power source (e.g., a battery) and the power conduit 64 is substantially internal to the therapy apparatus 10.

In certain embodiments, the patient's scalp 30 comprises hair and skin which cover the patient's skull. In other embodiments, at least a portion of the hair is removed prior to the phototherapy treatment, so that the therapy apparatus 10 substantially contacts the skin of the scalp 30.

In certain embodiments, the element 50 is adapted to contact the patient's scalp 30, thereby providing an interface between the therapy apparatus 10 and the patient's scalp 30. In certain such embodiments, the element 50 is coupled to the light source 40 and in other such embodiments, the element is also adapted to conform to the scalp 30, as schematically illustrated in FIG. 1. In this way, the element 50 positions the output emission area 41 of the light source 40 relative to the scalp 30. In certain such embodiments, the element 50 is mechanically adjustable so as to adjust the position of the light source 40 relative to the scalp 30. By fitting to the scalp 30 and holding the light source 40 in place, the element 50 inhibits temperature increases at the scalp 30 that would otherwise result from misplacement of the light source 40 relative to the scalp 30. In addition, in certain embodiments, the element 50 is mechanically adjustable so as to fit the therapy apparatus 10 to the patient's scalp 30.

In certain embodiments, the element 50 provides a reusable interface between the therapy apparatus 10 and the patient's scalp 30. In such embodiments, the element 50 can be cleaned or sterilized between uses of the therapy apparatus, particularly between uses by different patients. In other embodiments, the element 50 provides a disposable and replaceable interface between the therapy apparatus 10 and the patient's scalp 30. By using pre-sterilized and pre-packaged replaceable interfaces, certain embodiments can advantageously provide sterilized interfaces without undergoing cleaning or sterilization processing immediately before use.

In certain embodiments, the element 50 comprises a container (e.g., a cavity or bag) containing a material (e.g., gel or liquid). The container can be flexible and adapted to conform to the contours of the scalp 30. Other example materials contained in the container of the element 50 include, but are not limited to, thermal exchange materials such as glycerol and water. The element 50 of certain embodiments substantially covers the entire scalp 30 of the patient, as schematically illustrated in FIG. 2. In other embodiments, the element 50 only covers a localized portion of the scalp 30 in proximity to the irradiated portion of the scalp 30.

In certain embodiments, at least a portion of the element 50 is within an optical path of the light from the light source 40 to the scalp 30. In such embodiments, the element 50 is substantially optically transmissive at a wavelength of the light emitted by the output emission area 41 of the light source 40 and is adapted to reduce back reflections of the light. By reducing back reflections, the element 50 increases the amount of light transmitted to the brain 20 and reduces the need to use a higher power light source 40 which may otherwise create temperature increases at the scalp 30. In certain such embodiments, the element 50 comprises one or more optical coatings, films, layers, membranes, etc. in the optical path of the transmitted light which are adapted to reduce back reflections.

In certain such embodiments, the element 50 reduces back reflections by fitting to the scalp 30 so as to substantially reduce air gaps between the scalp 30 and the element 50 in the optical path of the light. The refractive-index mismatches between such an air gap and the element 50 and/or the scalp 30 would otherwise result in at least a portion of the light propagating from the light source 40 to the brain 20 to be reflected back towards the light source 40.

In addition, certain embodiments of the element 50 comprise a material having, at a wavelength of light emitted by the light source 40, a refractive index which substantially matches the refractive index of the scalp 30 (e.g., about 1.3), thereby reducing any index-mismatch-generated back reflections between the element 50 and the scalp 30. Examples of materials with refractive indices compatible with embodiments described herein include, but are not limited to, glycerol, water, and silica gels. Example index-matching gels include, but are not limited to, those available from Nye Lubricants, Inc. of Fairhaven, Mass.

In certain embodiments, the element 50 is adapted to cool the scalp 30 by removing heat from the scalp 30 so as to inhibit temperature increases at the scalp 30. In certain such embodiments, the element 50 comprises a reservoir (e.g., a chamber or a conduit) adapted to contain a coolant. The coolant flows through the reservoir near the scalp 30. The scalp 30 heats the coolant, which flows away from the scalp 30, thereby removing heat from the scalp 30 by active cooling. The coolant in certain embodiments circulates between the element 50 and a heat transfer device, such as a chiller, whereby the coolant is heated by the scalp 30 and is cooled by the heat transfer device. Example materials for the coolant include, but are not limited to, water or air.

Figure 3:
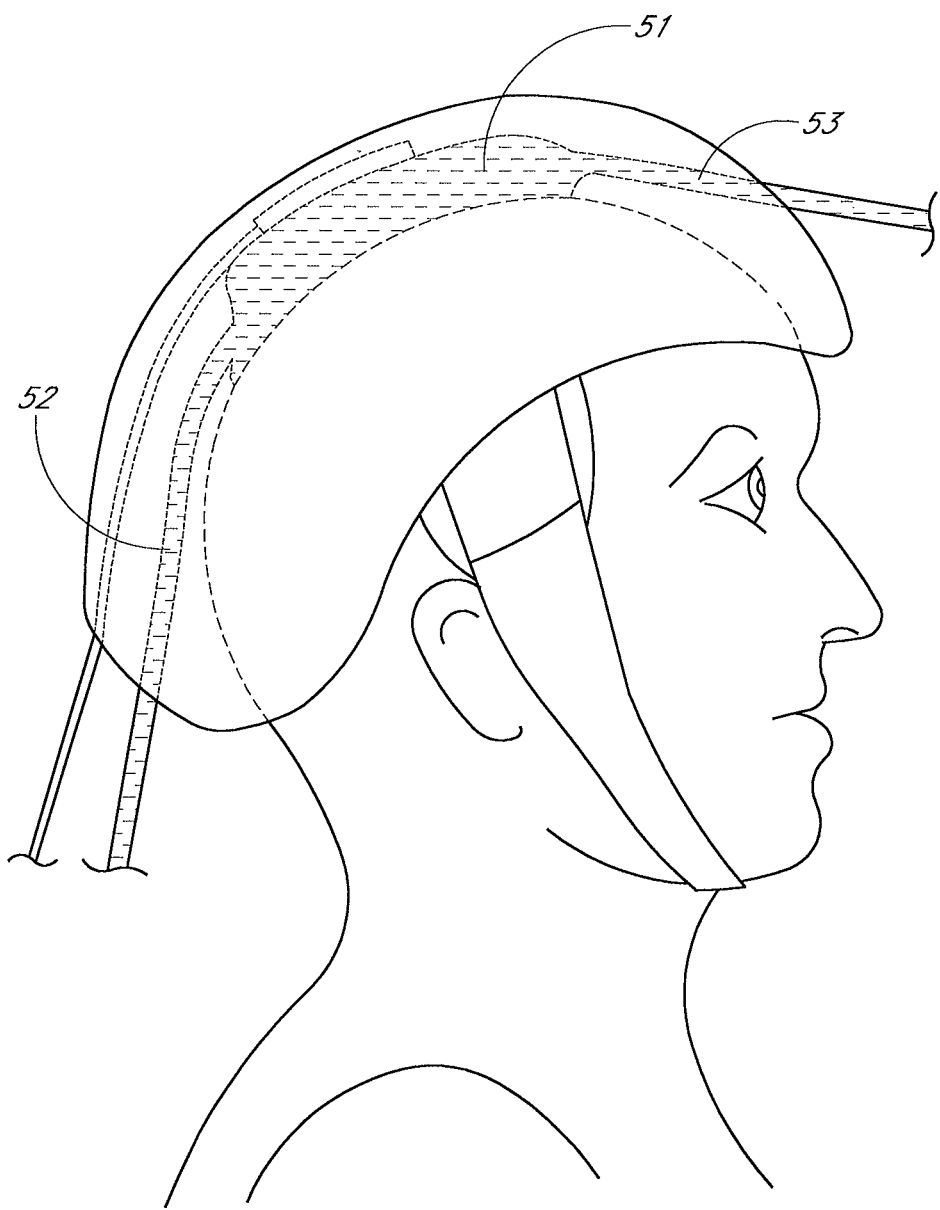
FIG. 3 schematically illustrates an embodiment with an element comprising a container coupled to an inlet conduit and an outlet conduit for the transport of a flowing material through the element.

In certain embodiments, the element 50 comprises a container 51 (e.g., a flexible bag) coupled to an inlet conduit 52 and an outlet conduit 53, as schematically illustrated in FIG. 3. A flowing material (e.g., water, air, or glycerol) can flow into the container 51 from the inlet conduit 52, absorb heat from the scalp 30, and flow out of the container 51 through the outlet conduit 53. Certain such embodiments can provide a mechanical fit of the container 51 to the scalp 30 and sufficient thermal coupling to prevent excessive heating of the scalp 30 by the light. In certain embodiments, the container 51 can be disposable and replacement containers 51 can be used for subsequent patients.

In still other embodiments, the element 50 comprises a container (e.g., a flexible bag) containing a material which does not flow out of the container but is thermally coupled to the scalp 30 so as to remove heat from the scalp 30 by passive cooling. Example materials include, but are not limited to, water, glycerol, and gel. In certain such embodiments, the non-flowing material can be pre-cooled (e.g., by placement in a refrigerator) prior to the phototherapy treatment to facilitate cooling of the scalp 30.

In certain embodiments, the element 50 is adapted to apply pressure to at least a portion of the scalp 30. By applying sufficient pressure, the element 50 can blanch the portion of the scalp 30 by forcing at least some blood out the optical path of the light energy. The blood removal resulting from the pressure applied by the element 50 to the scalp 30 decreases the corresponding absorption of the light energy by blood in the scalp 30. As a result, temperature increases due to absorption of the light energy by blood at the scalp 30 are reduced. As a further result, the fraction of the light energy transmitted to the subdermal target tissue of the brain 20 is increased. In certain embodiments, a pressure greater than two pounds per square inch is used to blanch the irradiated portion of the scalp 30, while in certain other embodiments, a pressure of at least one pound per square inch is used to blanch the irradiated portion of the scalp 30. Other ranges of pressures for blanching the irradiated portion of the scalp 30 are also compatible with certain embodiments described herein. The maximum pressure used to blanch the irradiated portion of the scalp 30 is limited in certain embodiments by patient comfort levels and tissue damage levels.

Figure 4A:
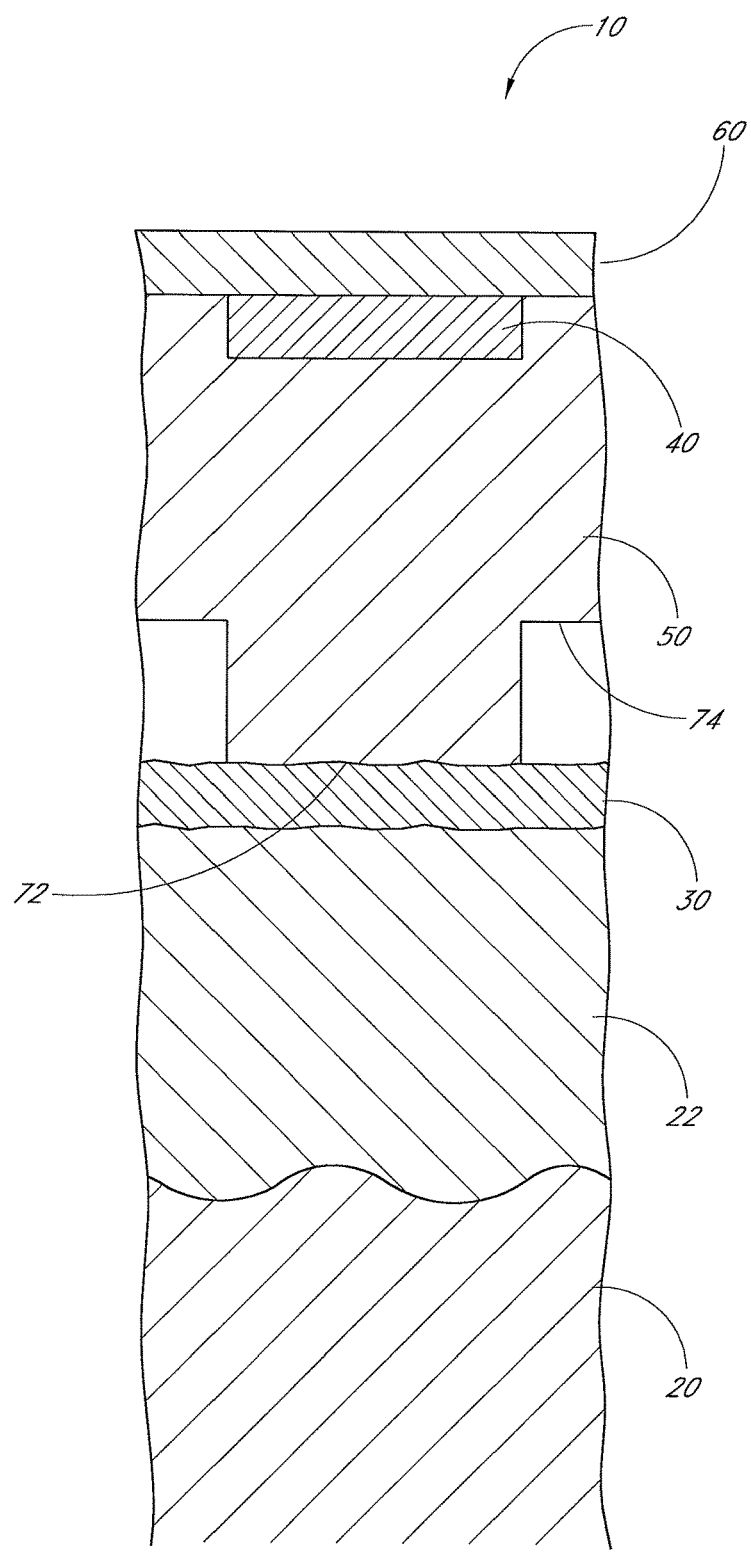
FIG. 4A schematically illustrates a fragmentary cross-sectional view taken along the lines 2-2 of FIG. 1, showing another embodiment of a portion of a therapy apparatus comprising an element with a portion contacting the scalp and a portion spaced away from the scalp.
Figure 4B:
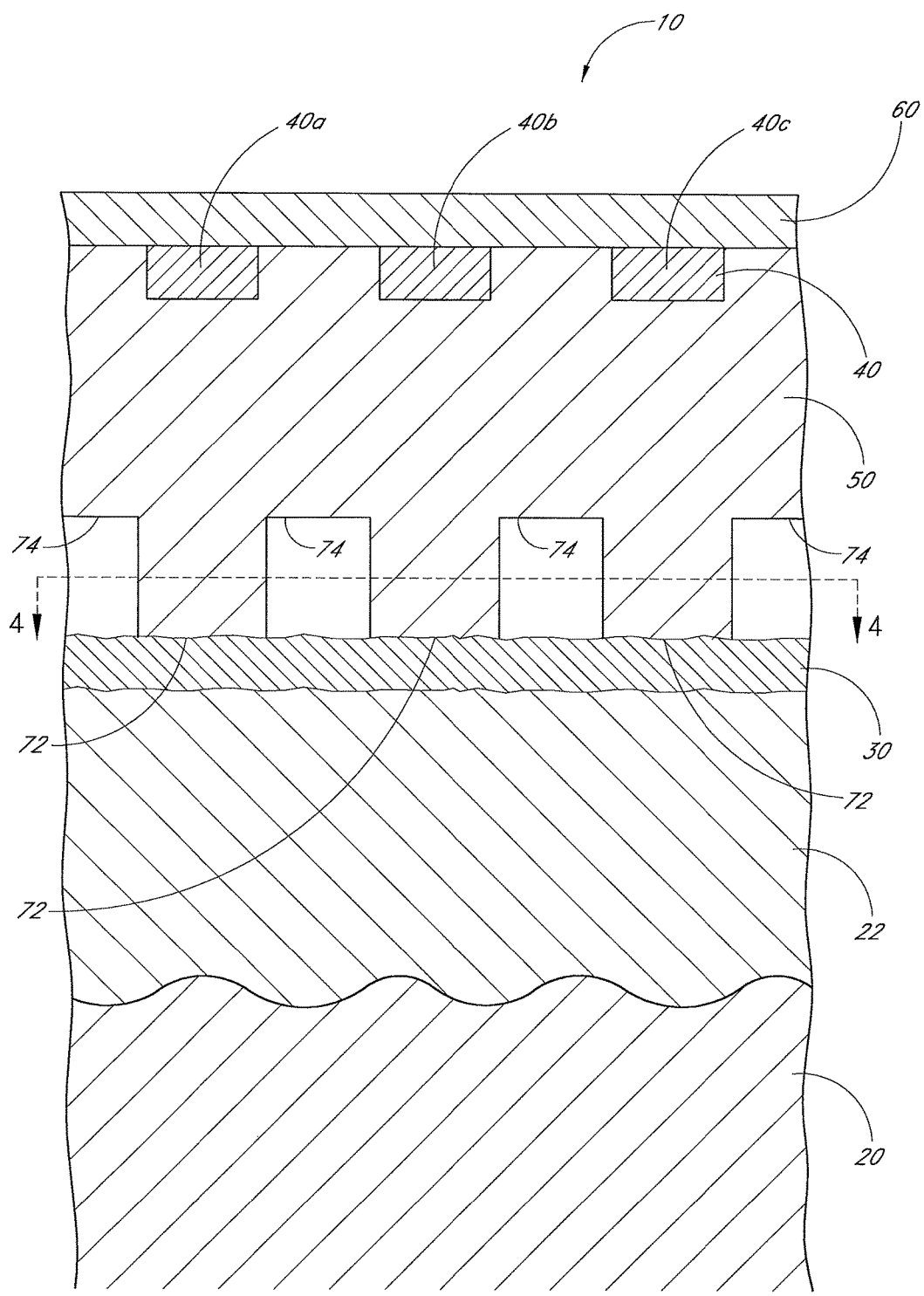
FIG. 4B schematically illustrates a fragmentary cross-sectional view taken along the lines 2-2 of FIG. 1, showing an embodiment of a portion of a therapy apparatus comprising a plurality of light sources and an element with portions contacting the scalp and portions spaced away from the scalp.

FIGS. 4A and 4B schematically illustrate embodiments of the element 50 adapted to facilitate the blanching of the scalp 30. In the cross-sectional view of a portion of the therapy apparatus 10 schematically illustrated in FIG. 4A, certain element portions 72 contact the patient's scalp 30 and other element portions 74 are spaced away from the scalp 30. The element portions 72 contacting the scalp 30 provide an optical path for light to propagate from the light source 40 to the scalp 30. The element portions 72 contacting the scalp 30 also apply pressure to the scalp 30, thereby forcing blood out from beneath the element portion 72. FIG. 4B schematically illustrates a similar view of an embodiment in which the light source 40 comprises a plurality of light sources 40a, 40b, 40c.

Figure 5A:
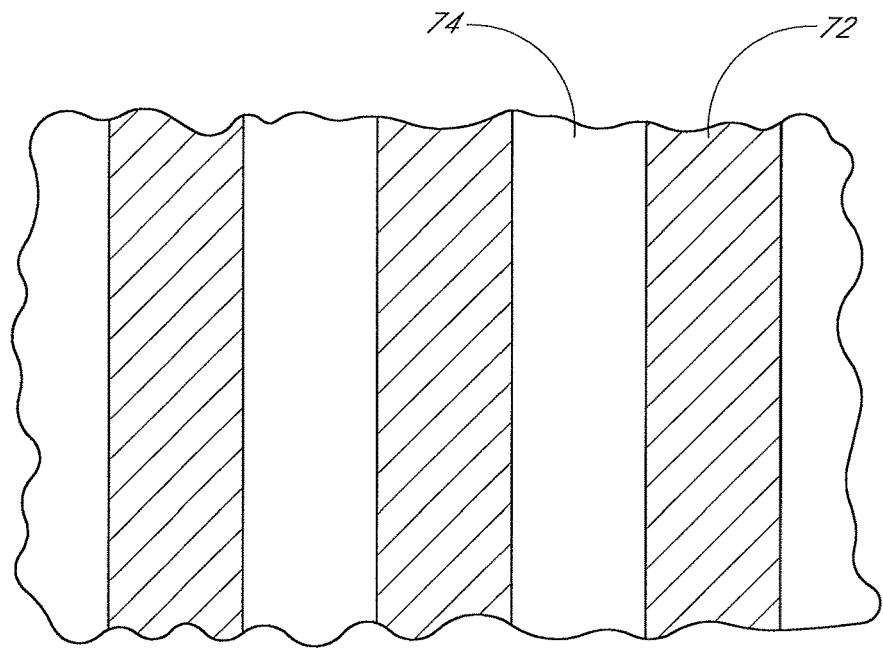
FIGS. 5A and 5B schematically illustrate cross-sectional views of two embodiments of the element in accordance with FIG. 4B taken along the line 4-4.
Figure 5B:
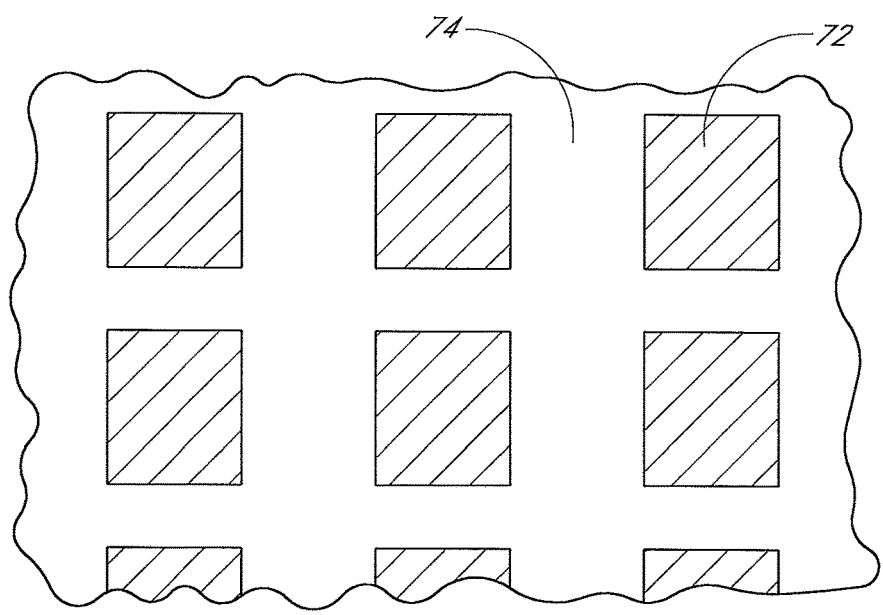

FIG. 5A schematically illustrates one embodiment of the cross-section along the line 4-4 of FIG. 4B. The element portions 72 contacting the scalp 30 comprise ridges extending along one direction, and the element portions 74 spaced away from the scalp 30 comprise troughs extending along the same direction. In certain embodiments, the ridges are substantially parallel to one another and the troughs are substantially parallel to one another. FIG. 5B schematically illustrates another embodiment of the cross-section along the line 4-4 of FIG. 4B. The element portions 72 contacting the scalp 30 comprise a plurality of projections in the form of a grid or array. More specifically, the portions 72 are rectangular and are separated by element portions 74 spaced away from the scalp 30, which form troughs extending in two substantially perpendicular directions. The portions 72 of the element 50 contacting the scalp 30 can be a substantial fraction of the total area of the element 50 or of the scalp 30.

Figure 6A:
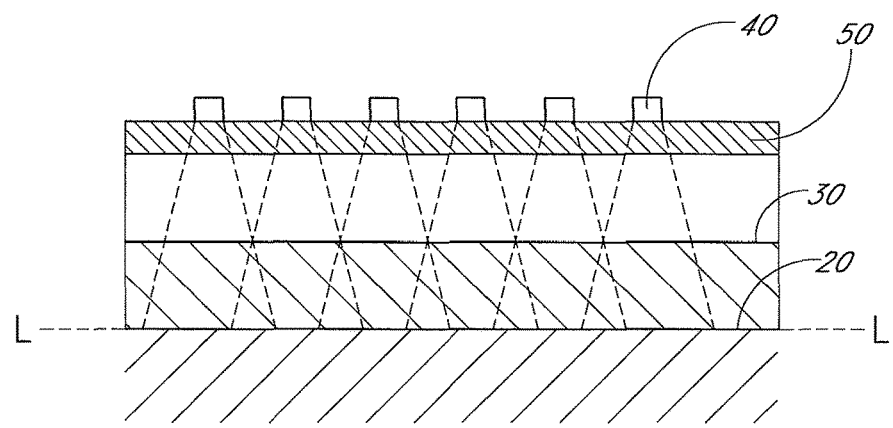
FIGS. 6A-6C schematically illustrate an embodiment in which the light sources are spaced away from the scalp.
Figure 6B:
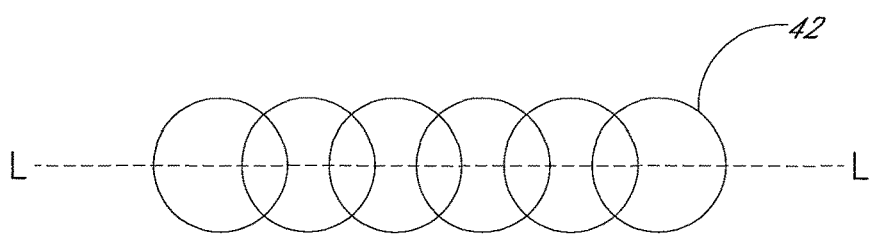
Figure 6C:
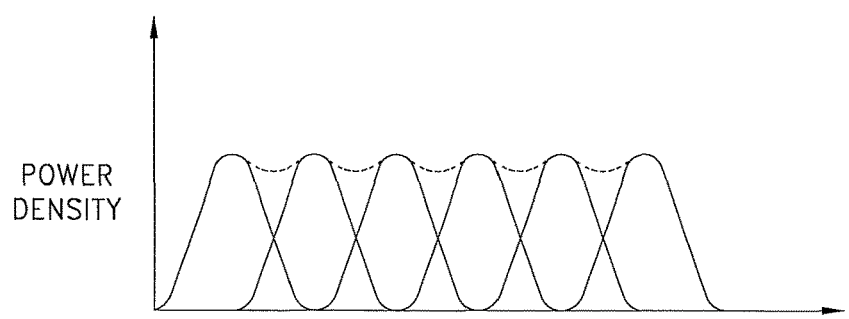

FIGS. 6A-6C schematically illustrate an embodiment in which the light sources 40 are spaced away from the scalp 30. In certain such embodiments, the light emitted by the light sources 40 propagates from the light sources 40 through the scalp 30 to the brain 20 and disperses in a direction generally parallel to the scalp 30, as shown in FIG. 6A. The light sources 40 are preferably spaced sufficiently far apart from one another such that the light emitted from each light source 40 overlaps with the light emitted from the neighboring light sources 40 at the brain 20. FIG. 6B schematically illustrates this overlap as the overlap of circular spots 42 at a reference depth at or below the surface of the brain 20. FIG. 6C schematically illustrates this overlap as a graph of the power density at the reference depth of the brain 20 along the line L-L of FIGS. 6A and 6B. Summing the power densities from the neighboring light sources 40 (shown as a dashed line in FIG. 6C) serves to provide a more uniform light distribution at the tissue to be treated. In such embodiments, the summed power density is preferably less than a damage threshold of the brain 20 and above an efficacy threshold.

Figure 7A:
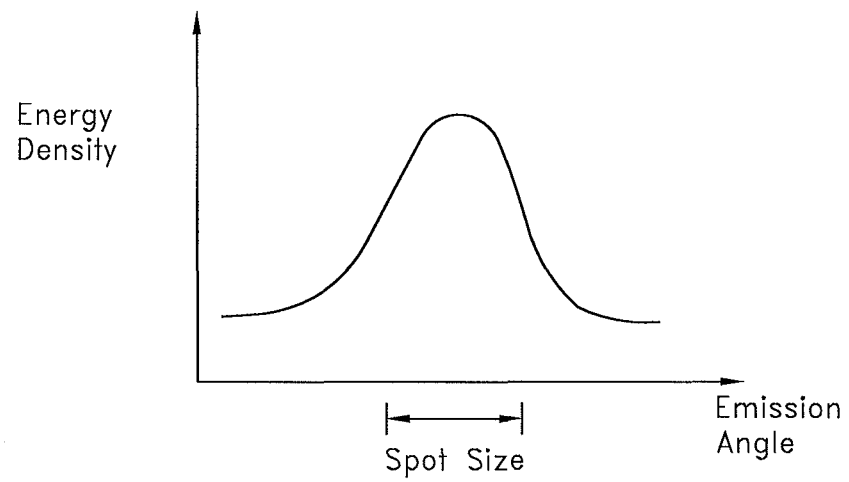
FIGS. 7A and 7B schematically illustrate the diffusive effect on the light by the element.
Figure 7B:
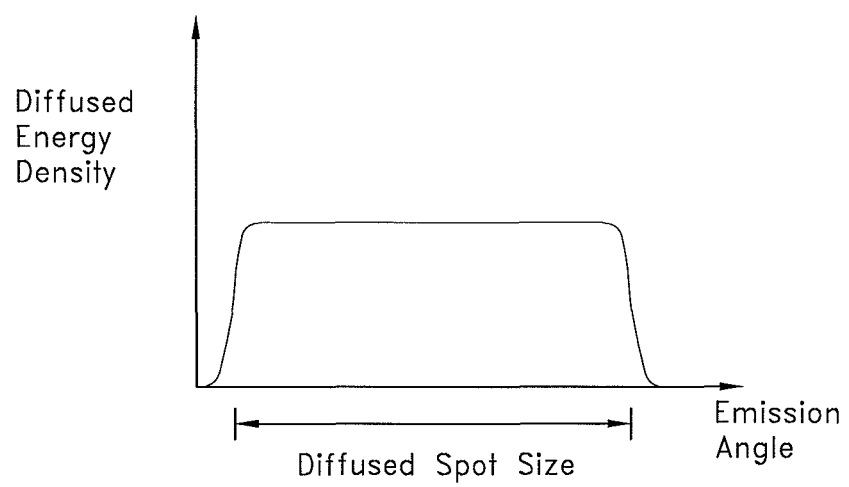

In certain embodiments, the element 50 is adapted to diffuse the light prior to reaching the scalp 30. FIGS. 7A and 7B schematically illustrate the diffusive effect on the light by the element 50. An example energy density profile of the light emitted by a light source 40, as illustrated by FIG. 7A, is peaked at a particular emission angle. After being diffused by the element 50, as illustrated by FIG. 7B, the energy density profile of the light does not have a substantial peak at any particular emission angle, but is substantially evenly distributed among a range of emission angles. By diffusing the light emitted by the light source 40, the element 50 distributes the light energy substantially evenly over the area to be illuminated, thereby inhibiting "hot spots" which would otherwise create temperature increases at the scalp 30. In addition, by diffusing the light prior to its reaching the scalp 30, the element 50 can effectively increase the spot size of the light impinging the scalp 30, thereby advantageously lowering the power density at the scalp 30, as described more fully below. In addition, in embodiments with multiple light sources 40, the element 50 can diffuse the light to alter the total light output distribution to reduce inhomogeneities.

In certain embodiments, the element 50 provides sufficient diffusion of the light such that the power density of the light is less than a maximum tolerable level of the scalp 30 and brain 20. In certain other embodiments, the element 50 provides sufficient diffusion of the light such that the power density of the light equals a therapeutic value at the target tissue. The element 50 can comprise example diffusers including, but are not limited to, holographic diffusers such as those available from Physical Optics Corp. of Torrance, Calif. and Display Optics P/N SN1333 from Reflexite Corp. of Avon, Conn.

Power Density

Phototherapy for the treatment of stroke is based in part on the discovery that power density (i.e., power per unit area or number of photons per unit area per unit time) and energy density (i.e., energy per unit area or number of photons per unit area) of the light energy applied to tissue appear to be significant factors in determining the relative efficacy of low level phototherapy. This discovery is particularly applicable with respect to treating and saving surviving but endangered neurons in a zone of danger surrounding the primary infarct after a stroke or cerebrovascular accident (CVA). Preferred methods described herein are based at least in part on the finding that, given a selected wavelength of light energy, it is the power density and/or the energy density of the light delivered to tissue (as opposed to the total power or total energy delivered to the tissue) that appears to be important factors in determining the relative efficacy of phototherapy.

Without being bound by theory or by a specific mechanism, it is believed that light energy delivered within a certain range of power densities and energy densities provides the desired biostimulative effect on the intracellular environment, such that proper function is returned to previously nonfunctioning or poorly functioning mitochondria in at-risk neurons. The biostimulative effect may include interactions with chromophores within the target tissue, which facilitate production of ATP thereby feeding energy to injured cells which have experienced decreased blood flow due to the stroke. Because strokes correspond to blockages or other interruptions of blood flow to portions of the brain, it is thought that any effects of increasing blood flow by phototherapy are of less importance in the efficacy of phototherapy for stroke victims. Further information regarding the role of power density and exposure time is described by Hans H. F. I. van Breugel and P. R. Dop Bär in "Power Density and Exposure Time of He—Ne Laser Irradiation Are More Important Than Total Energy Dose in Photo-Biomodulation of Human Fibroblasts In Vitro," Lasers in Surgery and Medicine, Volume 12, pp. 528-537 (1992), which is incorporated in its entirety by reference herein.

The significance of the power density used in phototherapy has ramifications with regard to the devices and methods used in phototherapy of brain tissue, as schematically illustrated by FIGS. 8A and 8B, which show the effects of scattering by intervening tissue. Further information regarding the scattering of light by tissue is provided by V. Tuchin in "Tissue Optics: Light Scattering Methods and Instruments for Medical Diagnosis," SPIE Press (2000), Bellingham, Wash., pp. 3-11, which is incorporated in its entirety by reference herein.

FIG. 8A schematically illustrates a light beam 80 impinging a portion 90 of a patient's scalp 30 and propagating through the patient's head to irradiate a portion 100 of the patient's brain tissue 20. In the example embodiment of FIG. 8A, the light beam 80 impinging the scalp 30 is collimated and has a circular cross-section with a radius of 2 cm and a cross-sectional area of approximately 12.5 cm$^2$. For comparison purposes, FIG. 8B schematically illustrates a light beam 82 having a significantly smaller cross-section impinging a smaller portion 92 of the scalp 30 to irradiate a portion 102 of the brain tissue 20. The light beam 82 impinging the scalp 30 in FIG. 8B is collimated and has a circular cross-section with a radius of 1 cm and a cross-sectional area of approximately 3.1 cm$^2$. The collimations, cross-sections, and radii of the light beams 80, 82 illustrated in FIGS. 8A and 8B are examples; other light beams with other parameters are also compatible with embodiments described herein. In particular, similar considerations apply to focused beams or diverging beams, as they are similarly scattered by the intervening tissue.

As shown in FIGS. 8A and 8B, the cross-sections of the light beams 80, 82 become larger while propagating through the head due to scattering from interactions with tissue of the head. Assuming that the angle of dispersion is 15 degrees and the irradiated brain tissue 20 is 2.5 cm below the scalp 30, the resulting area of the portion 100 of brain tissue 20 irradiated by the light beam 80 in FIG. 8A is approximately 22.4 cm$^2$. Similarly, the resulting area of the portion 102 of brain tissue 20 irradiated by the light beam 82 in FIG. 8B is approximately 8.8 cm$^2$.

Irradiating the portion 100 of the brain tissue 20 with a power density of 10 mW/cm$^2$ corresponds to a total power within the portion 100 of approximately 224 mW (10 mW/cm$^2$×22.4 cm$^2$). Assuming only approximately 5% of the light beam 80 is transmitted between the scalp 30 and the brain tissue 20, the incident light beam 80 at the scalp 30 will have a total power of approximately 4480 mW (224 mW/0.05) and a power density of approximately 358 mW/cm$^2$ (4480 mW/12.5 cm$^2$). Similarly, irradiating the portion 102 of the brain tissue 20 with a power density of 10 mW/cm$^2$ corresponds to a total power within the portion 102 of approximately 88 mW (10 mW/cm$^2$×8.8 cm$^2$), and with the same 5% transmittance, the incident light beam 82 at the scalp 30 will have a total power of approximately 1760 mW (88 mW/0.05) and a power density of approximately 568 mW/cm$^2$ (1760 mW/3.1 cm$^2$). These calculations are summarized in Table 1.

TABLE 1

|  | 2 cm Spot Size (FIG. 8A) | 1 cm Spot Size (FIG. 8B) |
|---|---|---|
| Scalp: | | |
| Area | 12.5 cm$^2$ | 3.1 cm$^2$ |
| Total power | 4480 mW | 1760 mW |
| Power density | 358 mW/cm$^2$ | 568 mW/cm$^2$ |
| Brain: | | |
| Area | 22.4 cm$^2$ | 8.8 cm$^2$ |
| Total power | 224 mW | 88 mW |
| Power density | 10 mW/cm$^2$ | 10 mW/cm$^2$ |

These example calculations illustrate that to obtain a desired power density at the brain 20, higher total power at the scalp 30 can be used in conjunction with a larger spot size at the scalp 30. Thus, by increasing the spot size at the scalp 30, a desired power density at the brain 20 can be achieved with lower power densities at the scalp 30 which can reduce the possibility of overheating the scalp 30. In certain embodiments, the light can be directed through an aperture to define the illumination of the scalp 30 to a selected smaller area.

Light Source

In certain embodiments, a single light source 40 is used as a light generator to generate light, while in other embodiments, a plurality of light sources 40 are used as a light generator to generate light. The light source 40 preferably generates light in the visible to near-infrared wavelength range. In certain embodiments, the light source 40 comprises one or more laser diodes, which each provide coherent light. In embodiments in which the light from the light source 40 is coherent, the emitted light may produce "speckling" due to coherent interference of the light. This speckling comprises intensity spikes which are created by constructive interference and can occur in proximity to the target tissue being treated. For example, while the average power density may be approximately 10 mW/cm$^2$, the power density of one such intensity spike in proximity to the brain tissue to be treated may be approximately 300 mW/cm$^2$. In certain embodiments, this increased power density due to speckling can improve the efficacy of treatments using coherent light over those using incoherent light for illumination of deeper tissues.

In other embodiments, the light source 40 provides incoherent light. Example light sources 40 of incoherent light include, but are not limited to, incandescent lamps or light-emitting diodes. A heat sink can be used with the light source 40 (for either coherent or incoherent sources) to remove heat from the light source 40 and to inhibit temperature increases at the scalp 30.

In certain embodiments, the light source 40 generates light which is substantially monochromatic (i.e., light having one wavelength, or light having a narrow band of wavelengths). So that the amount of light transmitted to the brain is maximized, the wavelength of the light is selected in certain embodiments to be at or near a transmission peak (or at or near an absorption minimum) for the intervening tissue. In certain such embodiments, the wavelength corresponds to a peak in the transmission spectrum of tissue at about 820 nanometers. In other embodiments, the wavelength of the light is preferably between about 630 nanometers and about 1064 nanometers, more preferably between about 780 nanometers and about 840 nanometers, and most preferably includes wavelengths of about 785, 790, 795, 800, 805, 810, 815, 820, 825, or 830 nanometers. An intermediate wavelength in a range between approximately 730 nanometers and approximately 750 nanometers (e.g., about 739 nanometers) appears to be suitable for penetrating the skull, although other wavelengths are also suitable and may be used.

In other embodiments, the light source 40 generates light having a plurality of wavelengths. For example, in certain embodiments, a band of wavelengths of (808±5) nanometers is used. In certain embodiments, the light source 40 is adapted to generate light having a first wavelength concurrently with light having a second wavelength. In certain other embodiments, the light source 40 is adapted to generate light having a first wavelength sequentially with light having a second wavelength.

In certain such embodiments, each wavelength is selected so as to work with one or more chromophores within the target tissue. Without being bound by theory or by a specific mechanism, it is believed that irradiation of chromophores increases the production of ATP in the target tissue, thereby producing beneficial effects, as described more fully below.

In certain embodiments, the light source 40 includes at least one continuously emitting GaAlAs laser diode having a wavelength of about 830 nanometers. In another embodiment, the light source 40 comprises a laser source having a wavelength of about 808 nanometers. In still other embodiments, the light source 40 includes at least one vertical cavity surface-emitting laser (VCSEL) diode. Other light sources 40 compatible with embodiments described herein include, but are not limited to, light-emitting diodes (LEDs) and filtered lamps.

The light source 40 is capable of emitting light energy at a power sufficient to achieve a predetermined power density at the subdermal target tissue (e.g., at a depth of approximately 2 centimeters from the dura). It is presently believed that phototherapy of tissue is most effective when irradiating the target tissue with power densities of light of at least about 0.01 mW/cm$^2$ and up to about 1 W/cm$^2$ at the level of the tissue. In various embodiments, the subsurface power density is at least about 0.01, 0.05, 0.1, 0.5, 1, 5, 10, 15, 20, 30, 40, 50, 60, 70, 80, or 90 mW/cm$^2$, respectively, depending on the desired clinical performance. In certain embodiments, the subsurface power density at the target tissue is about 0.01 mW/cm$^2$ to about 100 mW/cm$^2$, about 0.01 mW/cm$^2$ to about 50 mW/cm$^2$, about 2 mW/cm$^2$ to about 20 mW/cm$^2$, or about 5 mW/cm$^2$ to about 25 mW/cm$^2$. It is believed that these subsurface power densities are especially effective at producing the desired biostimulative effects on the tissue being treated.

Taking into account the attenuation of energy as it propagates from the skin surface, through body tissue, bone, and fluids, to the subdermal target tissue, surface power densities preferably between about 10 mW/cm$^2$ to about 10 W/cm$^2$, or more preferably between about 100 mW/cm$^2$ to about 500 mW/cm$^2$, will typically be used to attain the selected power densities at the subdermal target tissue. To achieve such surface power densities, the light source 40 is preferably capable of emitting light energy having a total power output of at least about 25 mW to about 100 W. In various embodiments, the total power output is limited to be no more than about 30, 50, 75, 100, 150, 200, 250, 300, 400, or 500 mW, respectively. In certain embodiments, the light source 40 comprises a plurality of sources used in combination to provide the total power output. The actual power output of the light source 40 is preferably controllably variable. In this way, the power of the light energy emitted can be adjusted in accordance with a selected power density at the subdermal tissue being treated.

Certain embodiments utilize a light source 40 that includes only a single laser diode that is capable of providing about 25 mW to about 100 W of total power output at the skin surface. In certain such embodiments, the laser diode can be optically coupled to the scalp 30 via an optical fiber or can be configured to provide a sufficiently large spot size to avoid power densities which would burn or otherwise damage the scalp 30. In other embodiments, the light source 40 utilizes a plurality of sources (e.g., laser diodes) arranged in a grid or array that together are capable of providing at least about 25 mW to about 100 W of total power output at the skin surface. The light source 40 of other embodiments may also comprise sources having power capacities outside of these limits.

Figure 9A:
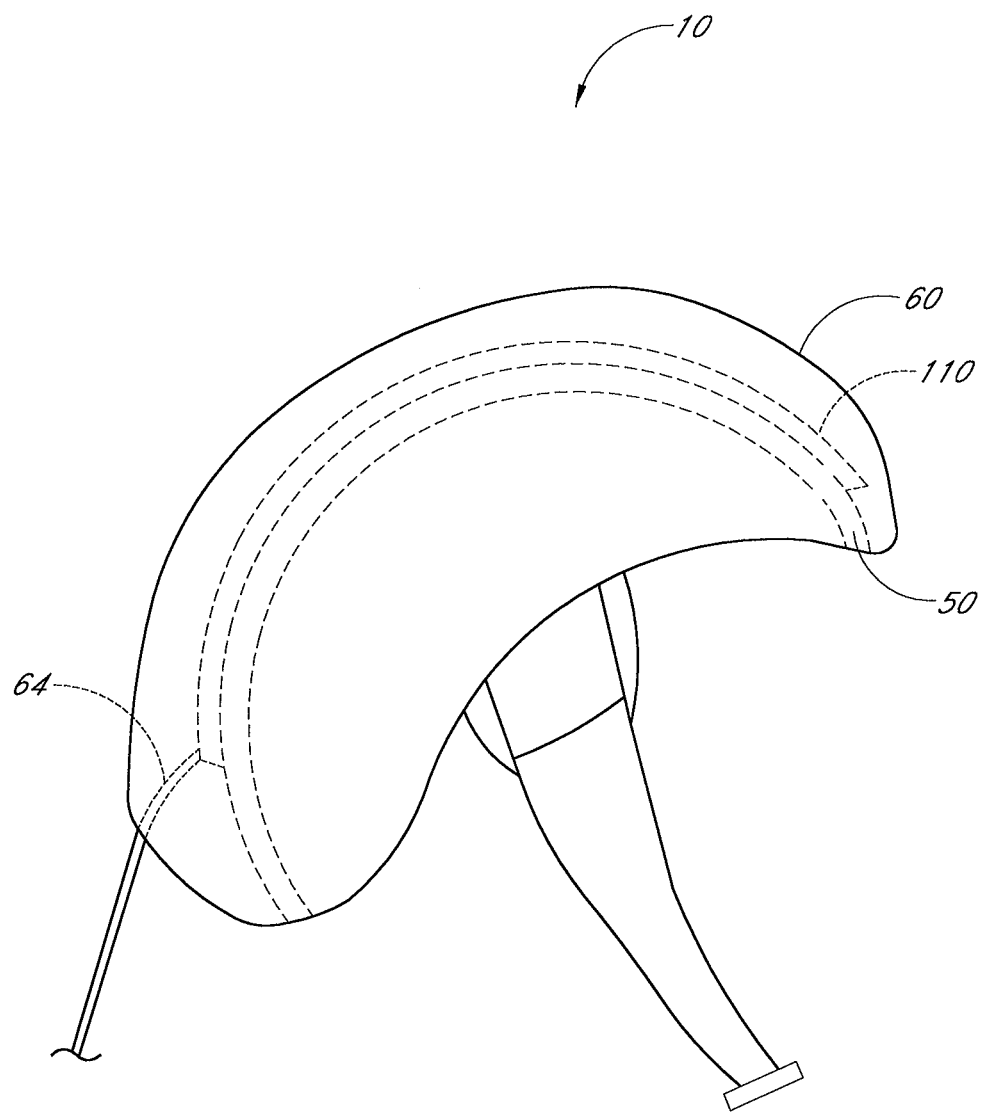
FIG. 9A schematically illustrates a therapy apparatus comprising a cap and a light source comprising a light blanket.
Figure 9B:
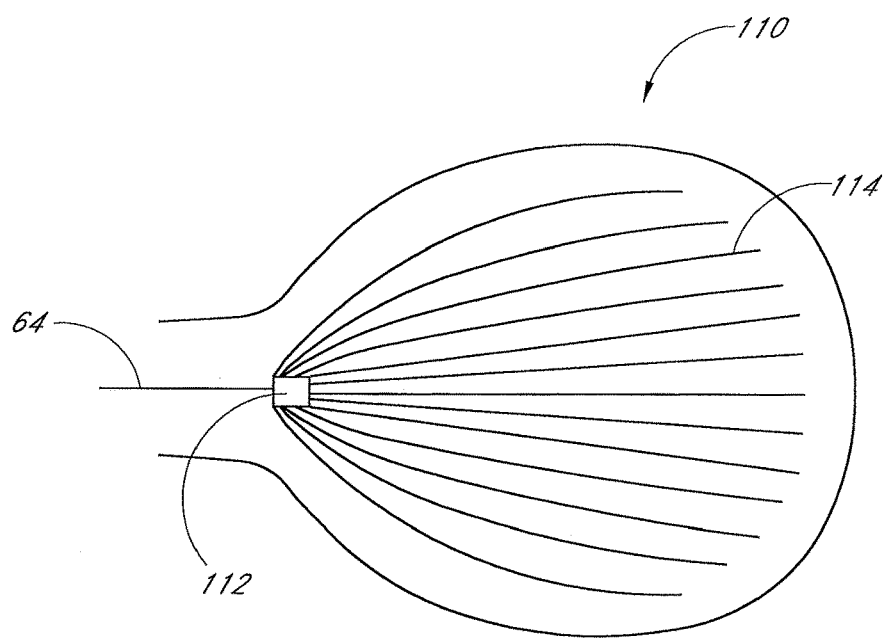
FIGS. 9B and 9C schematically illustrate two embodiments of the light blanket.
Figure 9C:
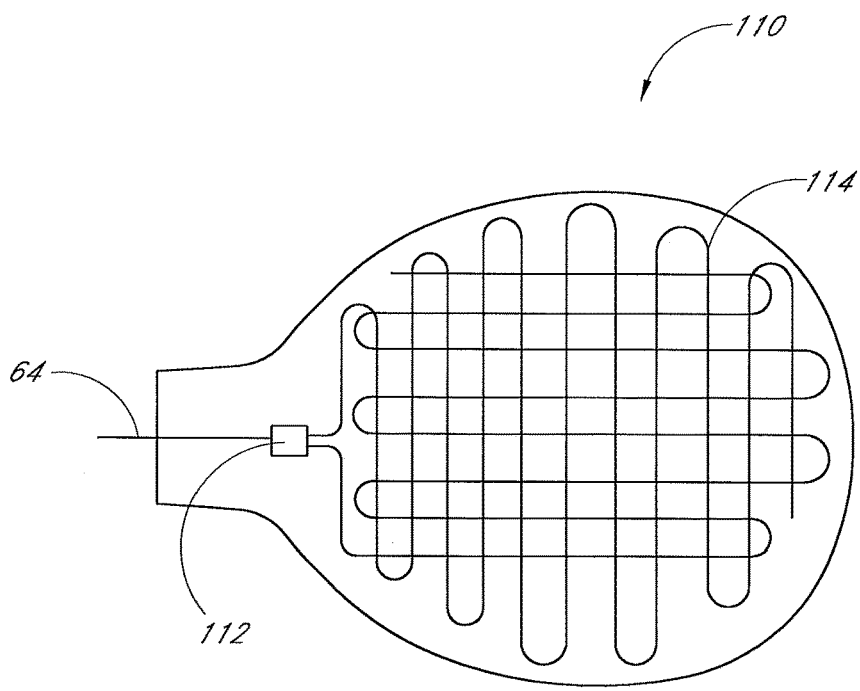

FIG. 9A schematically illustrates another embodiment of the therapy apparatus 10 which comprises the cap 60 and a light source comprising a light-emitting blanket 110. FIG. 9B schematically illustrates an embodiment of the blanket 110 comprising a flexible substrate 111 (e.g., flexible circuit board), a power conduit interface 112, and a sheet formed by optical fibers 114 positioned in a fan-like configuration. FIG. 9C schematically illustrates an embodiment of the blanket 110 comprising a flexible substrate 111, a power conduit interface 112, and a sheet formed by optical fibers 114 woven into a mesh. The blanket 110 is preferably positioned within the cap 60 so as to cover an area of the scalp 30 corresponding to a portion of the brain 20 to be treated.

In certain such embodiments, the power conduit interface 112 is adapted to be coupled to an optical fiber conduit 64 which provides optical power to the blanket 110. The optical power interface 112 of certain embodiments comprises a beam splitter or other optical device which distributes the incoming optical power among the various optical fibers 114. In other embodiments, the power conduit interface 112 is adapted to be coupled to an electrical conduit which provides electrical power to the blanket 110. In certain such embodiments, the power conduit interface 112 comprises one or more laser diodes, the output of which is distributed among the various optical fibers 114 of the blanket 110. In certain other embodiments, the blanket 110 comprises an electroluminescent sheet which responds to electrical signals from the power conduit interface 112 by emitting light. In such embodiments, the power conduit interface 112 comprises circuitry adapted to distribute the electrical signals to appropriate portions of the electroluminescent sheet.

The side of the blanket 110 nearer the scalp 30 is preferably provided with a light scattering surface, such as a roughened surface to increase the amount of light scattered out of the blanket 110 towards the scalp 30. The side of the blanket 110 further from the scalp 30 is preferably covered by a reflective coating so that light emitted away from the scalp 30 is reflected back towards the scalp 30. This configuration is similar to configurations used for the "back illumination" of liquid-crystal displays (LCDs). Other configurations of the blanket 110 are compatible with embodiments described herein.

In certain embodiments, the light source 40 generates light which cause eye damage if viewed by an individual. In such embodiments, the apparatus 50 can be configured to provide eye protection so as to avoid viewing of the light by individuals. For example, opaque materials can be appropriately placed to block the light from being viewed directly. In addition, interlocks can be provided so that the light source 40 is not activated unless the apparatus 50 is in place, or other appropriate safety measures are taken.

Light Delivery Apparatuses

The phototherapy methods for the treatment of stroke described herein may be practiced and described using, for example, a low level laser therapy apparatus such as that shown and described in U.S. Pat. No. 6,214,035, U.S. Pat. No. 6,267,780, U.S. Pat. No. 6,273,905 and U.S. Pat. No. 6,290,714, which are all incorporated in their entirety by reference herein, as are the references incorporated by reference therein.

Figure 10:
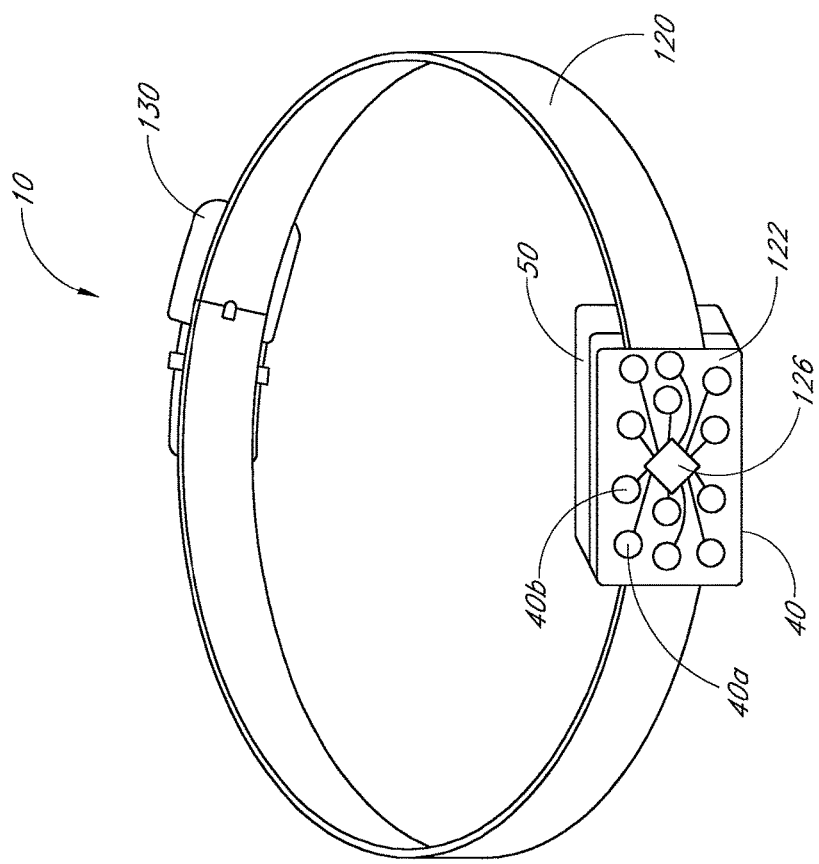
FIG. 10 schematically illustrates a therapy apparatus comprising a flexible strap and a housing.

Another suitable phototherapy apparatus in accordance with embodiments described here is illustrated in FIG. 10. The illustrated therapy apparatus 10 includes a light source 40, an element 50, and a flexible strap 120 adapted for securing the therapy apparatus 10 over an area of the patient's head. The light source 40 can be disposed on the strap 120 itself, or in a housing 122 coupled to the strap 120. The light source 40 preferably comprises a plurality of diodes 40a, 40b, etc. capable of emitting light energy having a wavelength in the visible to near-infrared wavelength range. The element 50 is adapted to be positioned between the light source 40 and the patient's scalp 30.

The therapy apparatus 10 further includes a power supply (not shown) operatively coupled to the light source 40, and a programmable controller 126 operatively coupled to the light source 40 and to the power supply. The programmable controller 126 is configured to control the light source 40 so as to deliver a predetermined power density to the brain tissue 20. In certain embodiments, as schematically illustrated in FIG. 10, the light source 40 comprises the programmable controller 126. In other embodiments the programmable controller 126 is a separate component of the therapy apparatus 10.

In certain embodiments, the strap 120 comprises a loop of elastomeric material sized appropriately to fit snugly onto the patient's scalp 30. In other embodiments, the strap 120 comprises an elastomeric material to which is secured any suitable securing means 130, such as mating Velcro strips, buckles, snaps, hooks, buttons, ties, or the like. The precise configuration of the strap 120 is subject only to the limitation that the strap 120 is capable of maintaining the light source 40 in a selected position so that light energy emitted by the light source 40 is directed towards the targeted brain tissue 20.

In the example embodiment illustrated in FIG. 10, the housing 122 comprises a layer of flexible plastic or fabric that is secured to the strap 120. In other embodiments, the housing 122 comprises a plate or an enlarged portion of the strap 120. Various strap configurations and spatial distributions of the light sources 40 are compatible with embodiments described herein so that the therapy apparatus 10 can treat selected portions of brain tissue.

Figure 11:
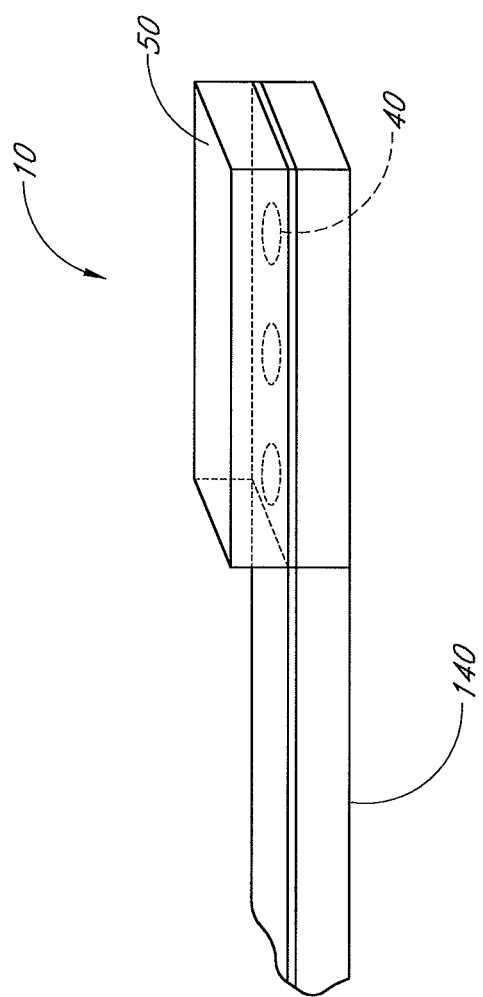
FIG. 11 schematically illustrates a therapy apparatus comprising a handheld probe.

In still other embodiments, the therapy apparatus 10 for delivering the light energy includes a handheld probe 140, as schematically illustrated in FIG. 11. The probe 140 includes a light source 40 and an element 50 as described herein.

Figure 12:
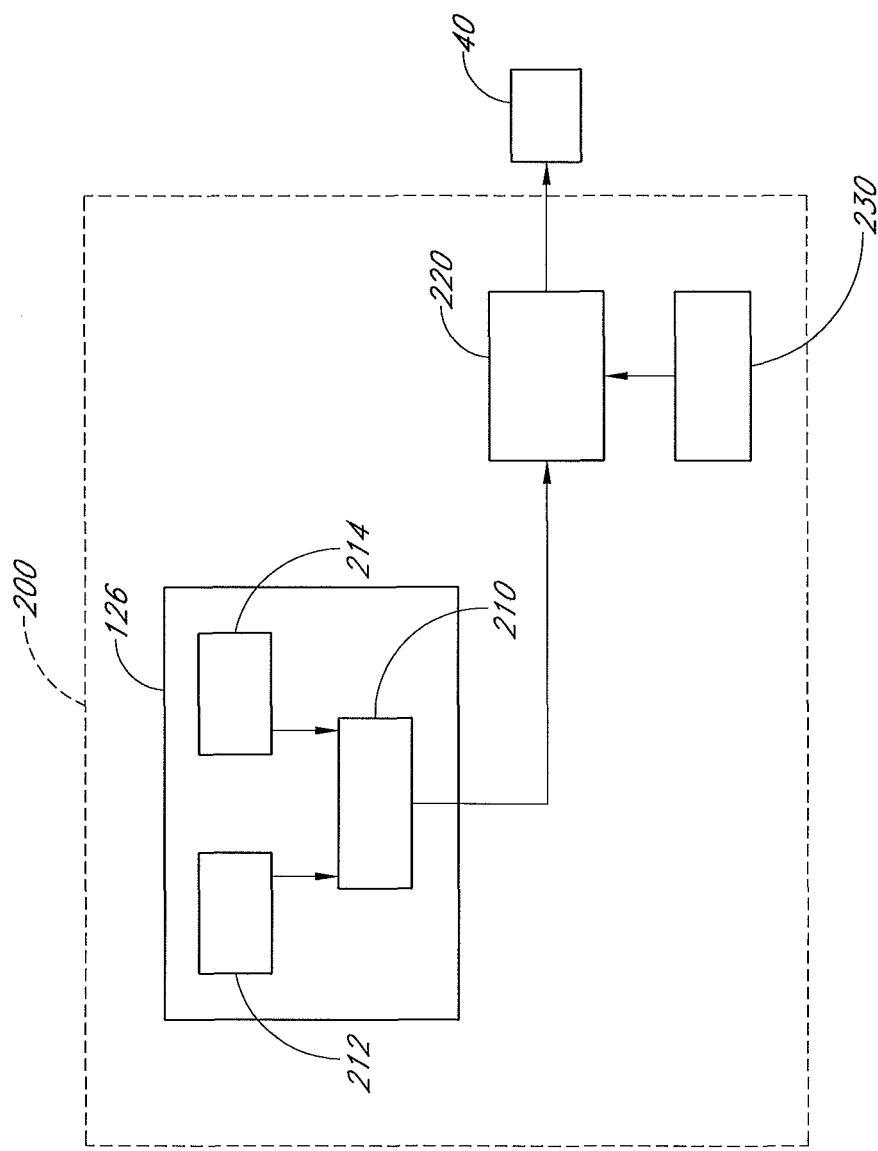
FIG. 12 is a block diagram of a control circuit comprising a programmable controller.

FIG. 12 is a block diagram of a control circuit 200 comprising a programmable controller 126 according to embodiments described herein. The control circuit 200 is configured to adjust the power of the light energy emitted by the light source 40 to generate a predetermined surface power density at the scalp 30 corresponding to a predetermined energy delivery profile, such as a predetermined subsurface power density, to the target area of the brain 20.

In certain embodiments, the programmable controller 126 comprises a logic circuit 210, a clock 212 coupled to the logic circuit 210, and an interface 214 coupled to the logic circuit 210. The clock 212 of certain embodiments provides a timing signal to the logic circuit 210 so that the logic circuit 210 can monitor and control timing intervals of the applied light. Examples of timing intervals include, but are not limited to, total treatment times, pulsewidth times for pulses of applied light, and time intervals between pulses of applied light. In certain embodiments, the light sources 40 can be selectively turned on and off to reduce the thermal load on the scalp 30 and to deliver a selected power density to particular areas of the brain 20.

The interface 214 of certain embodiments provides signals to the logic circuit 210 which the logic circuit 210 uses to control the applied light. The interface 214 can comprise a user interface or an interface to a sensor monitoring at least one parameter of the treatment. In certain such embodiments, the programmable controller 126 is responsive to signals from the sensor to preferably adjust the treatment parameters to optimize the measured response. The programmable controller 126 can thus provide closed-loop monitoring and adjustment of various treatment parameters to optimize the phototherapy. The signals provided by the interface 214 from a user are indicative of parameters that may include, but are not limited to, patient characteristics (e.g., skin type, fat percentage), selected applied power densities, target time intervals, and power density/timing profiles for the applied light.

In certain embodiments, the logic circuit 210 is coupled to a light source driver 220. The light source driver 220 is coupled to a power supply 230, which in certain embodiments comprises a battery and in other embodiments comprises an alternating current source. The light source driver 220 is also coupled to the light source 40. The logic circuit 210 is responsive to the signal from the clock 212 and to user input from the user interface 214 to transmit a control signal to the light source driver 220. In response to the control signal from the logic circuit 210, the light source driver 220 adjust and controls the power applied to the light sources 40. Other control circuits besides the control circuit 200 of FIG. 12 are compatible with embodiments described herein.

In certain embodiments, the logic circuit 110 is responsive to signals from a sensor monitoring at least one parameter of the treatment to control the applied light. For example, certain embodiments comprise a temperature sensor thermally coupled to the scalp 30 to provide information regarding the temperature of the scalp 30 to the logic circuit 210. In such embodiments, the logic circuit 210 is responsive to the information from the temperature sensor to transmit a control signal to the light source driver 220 so as to adjust the parameters of the applied light to maintain the scalp temperature below a predetermined level. Other embodiments include example biomedical sensors including, but not limited to, a blood flow sensor, a blood gas (e.g., oxygenation) sensor, an ATP production sensor, or a cellular activity sensor. Such biomedical sensors can provide real-time feedback information to the logic circuit 210. In certain such embodiments, the logic circuit 110 is responsive to signals from the sensors to preferably adjust the parameters of the applied light to optimize the measured response. The logic circuit 110 can thus provide closed-loop monitoring and adjustment of various parameters of the applied light to optimize the phototherapy.

Figure 13:
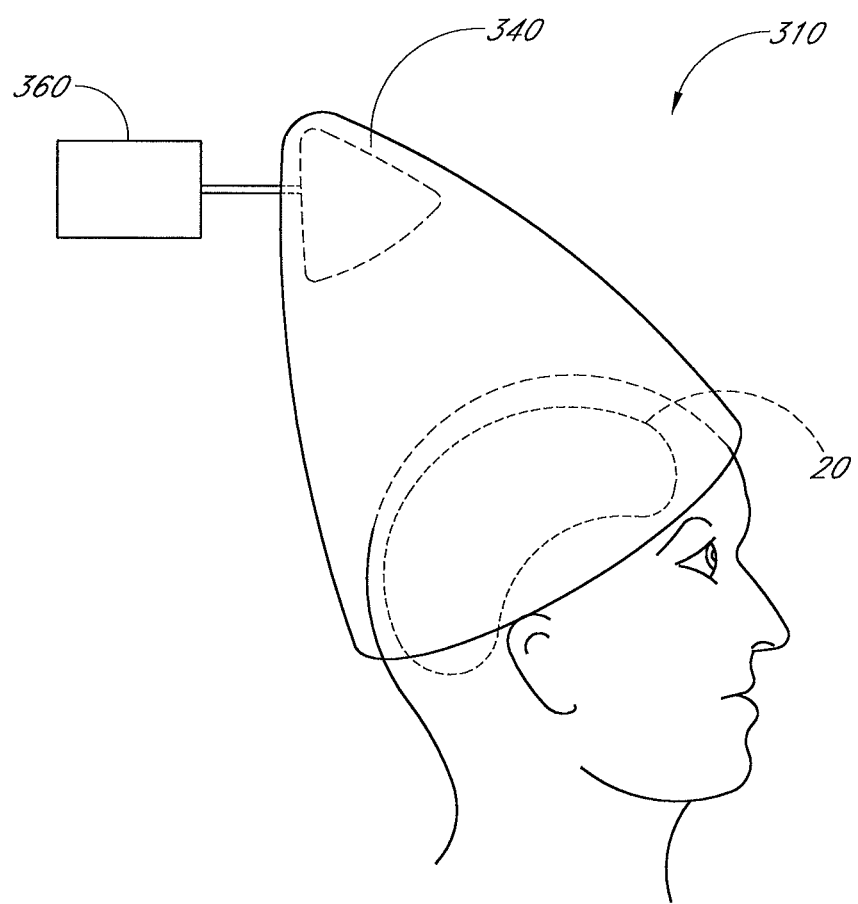
FIG. 13 schematically illustrates a therapy apparatus comprising a light source and a controller.

In certain embodiments, as schematically illustrated in FIG. 13, the therapy apparatus 310 comprises a light source 340 adapted to irradiate a portion of the patient's brain 20 with an efficacious power density and wavelength of light. The therapy apparatus 310 further comprises a controller 360 for energizing said light source 340, so as to selectively produce a plurality of different irradiation patterns on the patient's scalp 30. Each of the irradiation patterns is comprised of a least one illuminated area that is small compared to the patient's scalp 30, and at least one non-illuminated area.

In certain embodiments, the light source 340 includes an apparatus for adjusting the emitted light to irradiate different portions of the scalp 30. In certain such embodiments, the apparatus physically moves the light source 40 relative to the scalp 30. In other embodiments, the apparatus does not move the light source 40, but redirects the emitted light to different portions of the scalp 30. In an example embodiment, as schematically illustrated in FIG. 14, the light source 340 comprises a laser diode 342 and a galvometer 344, both of which are electrically coupled to the controller 360. The galvometer 344 comprises a mirror 346 mounted onto an assembly 348 which is adjustable by a plurality of motors 350. Light emitted by the laser diode 342 is directed toward the mirror 346 and is reflected to selected portions of the patient's scalp 30 by selectively moving the mirror 346 and selectively activating the laser diode 342. In certain embodiments, the therapy apparatus 310 comprises an element 50 adapted to inhibit temperature increases at the scalp 30 as described herein.

Figure 15A:
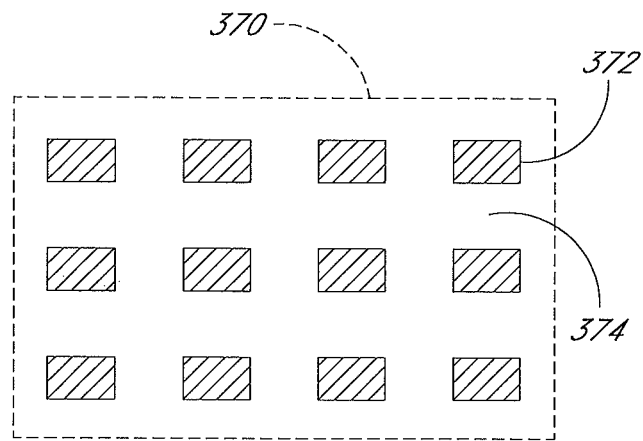
FIGS. 15A and 15B schematically illustrate two irradiation patterns that are spatially shifted relative to each other.

FIG. 15A schematically illustrates an irradiation pattern 370 in accordance with embodiments described herein. The irradiation pattern 370 comprises at least one illuminated area 372 and at least one non-illuminated area 374. In certain embodiments, the irradiation pattern 370 is generated by scanning the mirror 346 so that the light impinges the patient's scalp 30 in the illuminated area 372 but not in the non-illuminated area 374. Certain embodiments modify the illuminated area 372 and the non-illuminated area 374 as a function of time.

Figure 15B:
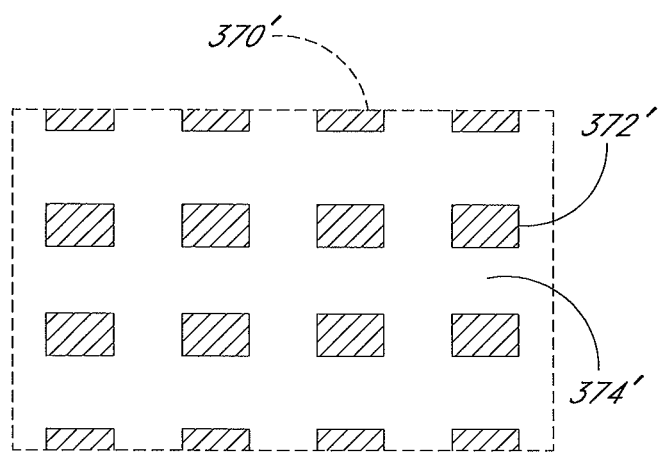

This selective irradiation can be used to reduce the thermal load on particular locations of the scalp 30 by moving the light from one illuminated area 372 to another. For example, by irradiating the scalp 30 with the irradiation pattern 370 schematically illustrated in FIG. 15A, the illuminated areas 372 of the scalp 30 are heated by interaction with the light, and the non-illuminated areas 374 are not heated. By subsequently irradiating the scalp 30 with the complementary irradiation pattern 370' schematically illustrated in FIG. 15B, the previously non-illuminated areas 374 are now illuminated areas 372', and the previously illuminated areas 372 are now non-illuminated areas 374'. A comparison of the illuminated areas 372 of the irradiation pattern 370 of FIG. 15A with the illuminated area 372' of the irradiation pattern 370' of FIG. 15B shows that the illuminated areas 372, 372' do not significantly overlap one another. In this way, the thermal load at the scalp 30 due to the absorption of the light can be distributed across the scalp 30, thereby avoiding unduly heating one or more portions of the scalp 30.

Figure 16:
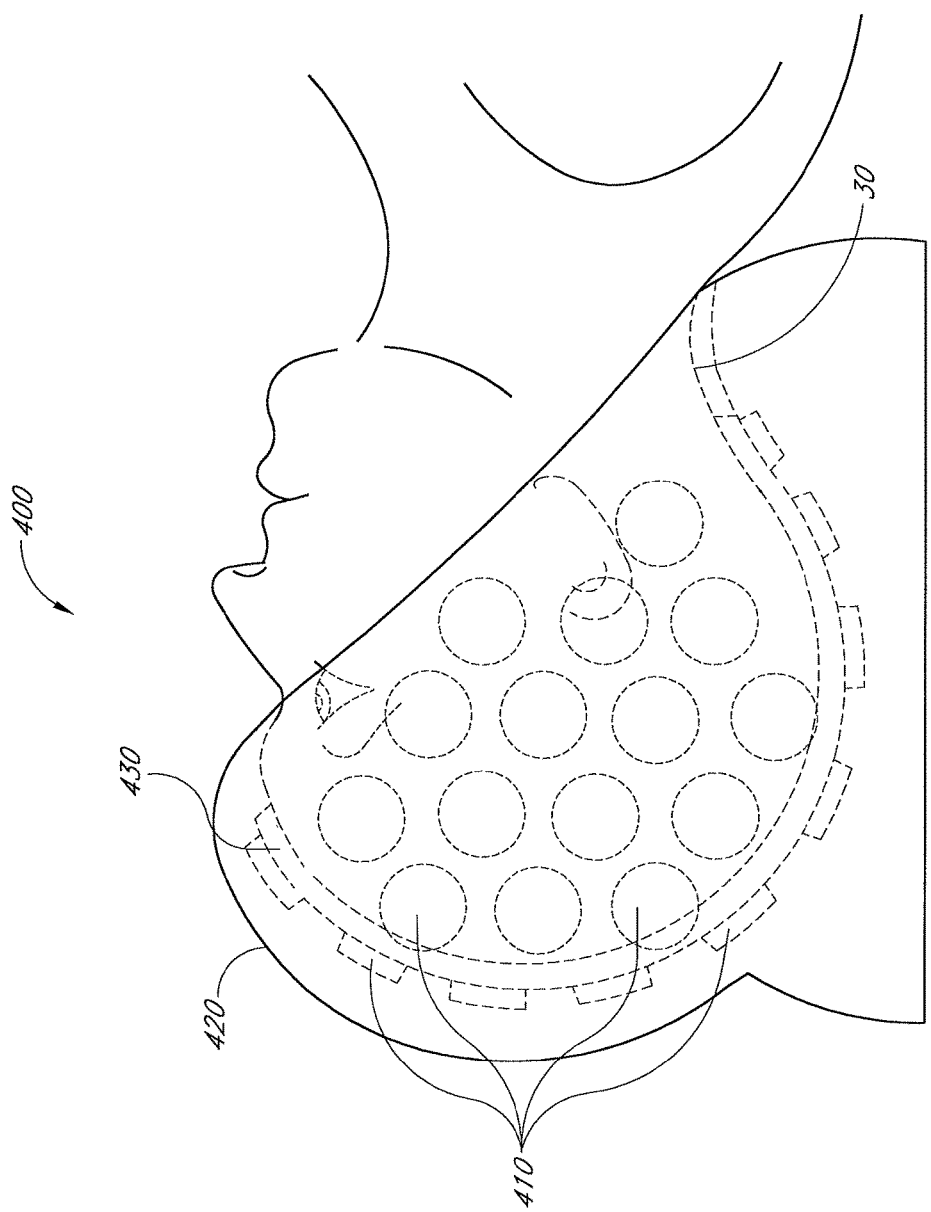
FIG. 16 schematically illustrates an example therapy apparatus in accordance with embodiments described herein.

FIG. 16 schematically illustrates another therapy apparatus 400 in accordance with embodiments described herein. The therapy apparatus 400 comprises a plurality of light sources 410 in a housing 420. Each light source 410 has an output emission area positioned to irradiate a corresponding portion of the brain 20 with an efficacious power density and wavelength of light. In certain embodiments, these portions overlap such that the portion of the brain 20 irradiated by two or more light sources 410 overlap one another at least in part. As described herein, the light sources 410 can be activated by a controller (not shown) in concert or separately to produce a predetermined irradiation pattern.

The therapy apparatus 400 of FIG. 16 further comprises a cap 430 interposed between the light sources 410 and the patient's scalp 30, such that light passes through the cap 430 prior to reaching the scalp 30. In certain embodiments, the cap 430 is substantially optically transmissive at the wavelength and reduces back reflections of the light. The cap 430 of certain embodiments fits to the scalp 30 so as to substantially reduce air gaps between the scalp 30 and the cap 430. In certain embodiments, the cap 430 comprises a material having a refractive index which substantially matches a refractive index of the scalp 30. In certain embodiments, the cap 430 comprises a material having a refractive index which substantially matches a refractive index of the skin and/or hair of the scalp 30.

In the embodiment schematically illustrated by FIG. 16, the cap 430 is wearable over the patient's scalp 30. In certain such embodiments, the patient wears the cap 430 and is in a reclining position so as to place his head in proximity to the light sources 410. The cap 430 is adapted to inhibit temperature increases at the scalp 30 caused by the light from the light sources 410, as described herein (e.g., by cooling the scalp 30, by blanching a portion of the scalp 30, by diffusing the light prior to reaching the scalp 30).

Example Wearable Apparatus

Figure 19:
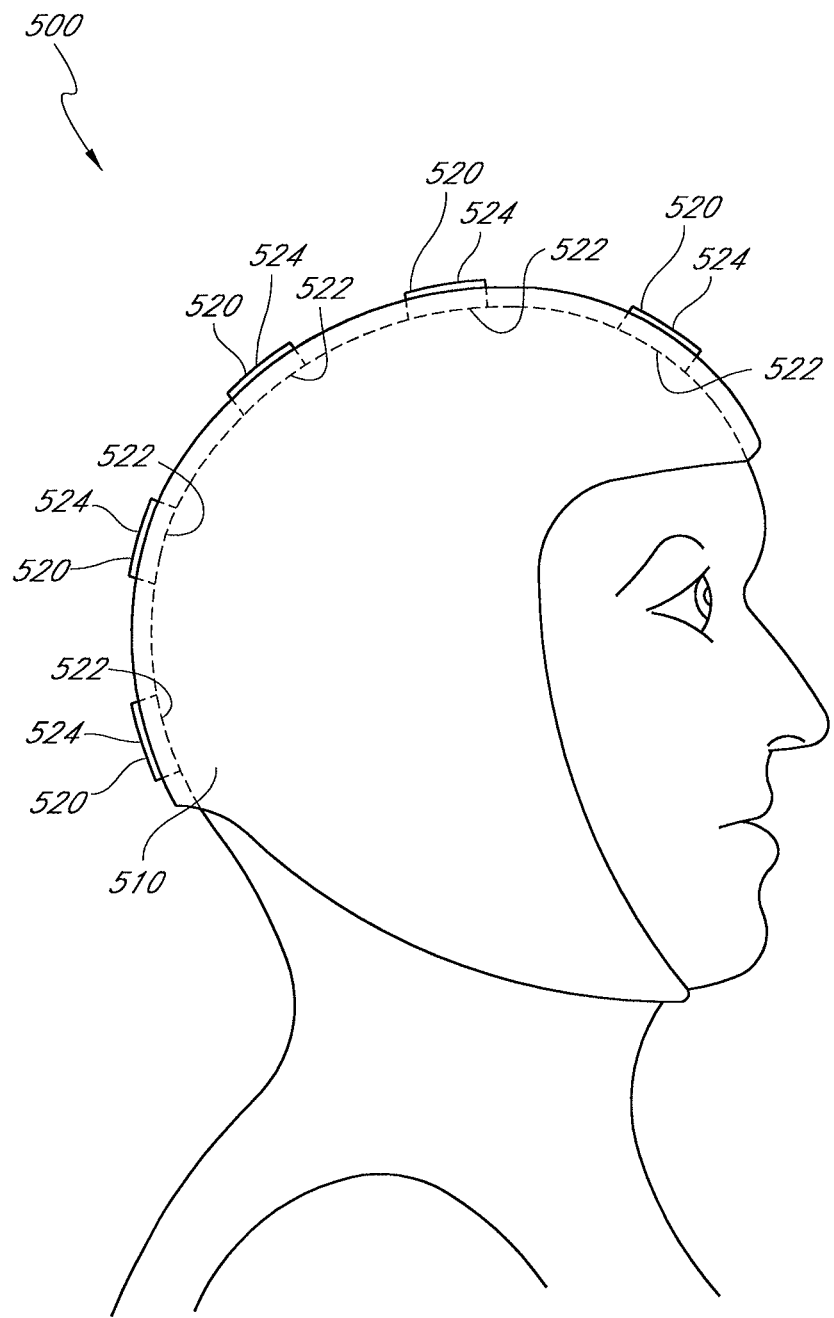
FIG. 19 schematically illustrates an example apparatus which is wearable by a patient for treating the patient's brain.

FIG. 19 schematically illustrates an example apparatus 500 which is wearable by a patient for treating the patient's brain. The apparatus 500 comprises a body 510 and a plurality of elements 520. The body 510 covers at least a portion of the patient's scalp when the apparatus 500 is worn by the patient. Each element 520 has a first portion 522 which conforms to a corresponding portion of the patient's scalp when the apparatus 500 is worn by the patient. Each element 520 has a second portion 524 which conforms to a light source (not shown in FIG. 19) removably contacting the element. Each element 520 is substantially transmissive (e.g., substantially transparent or substantially translucent) to light from the light source to irradiate at least a portion of the patient's brain. In certain embodiments, the light from the light source after being transmitted through each element 520 has a power density which penetrates the patient's cranium to deliver an efficacious amount of light to at least a portion of the patient's brain.

Figure 20:
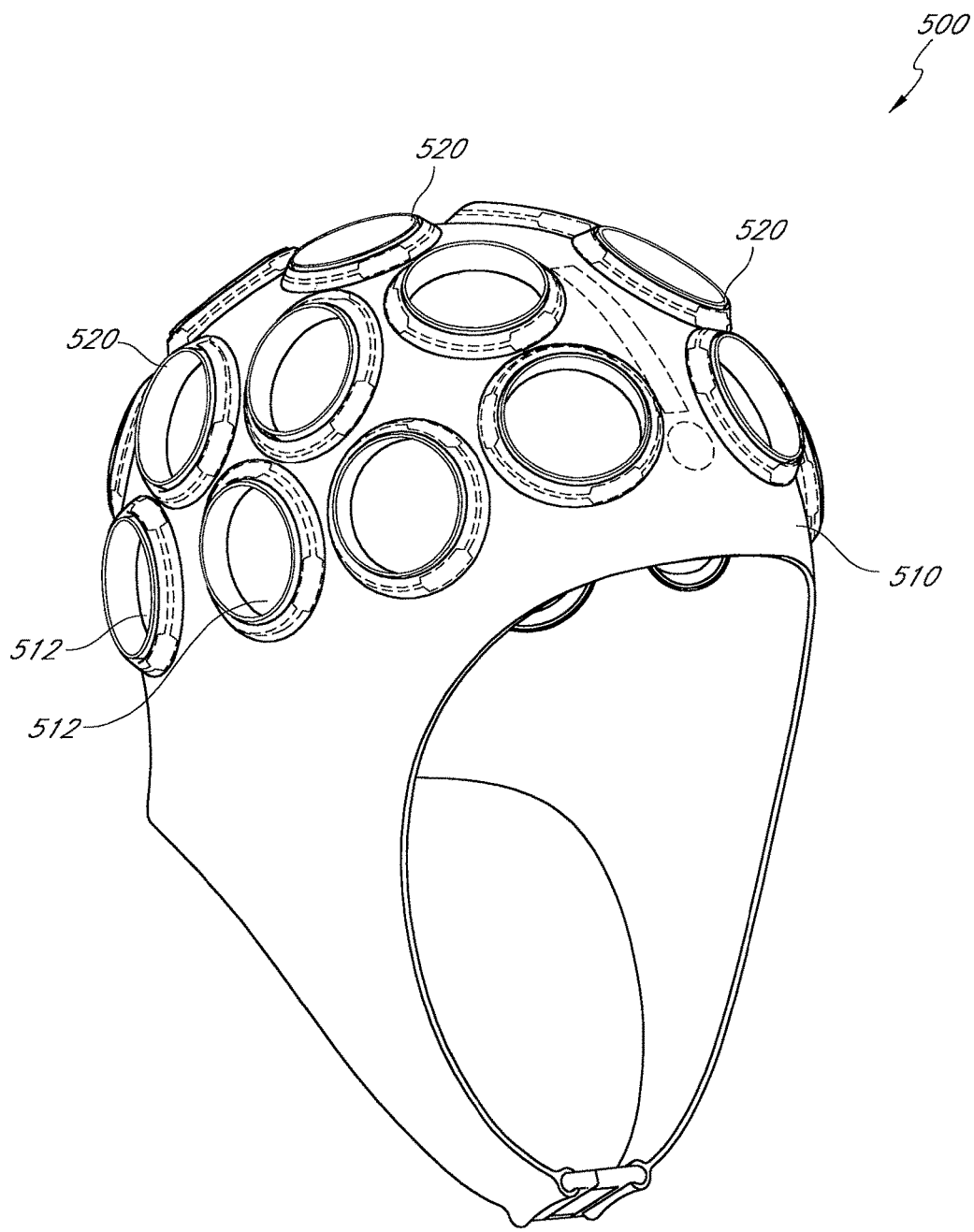
FIG. 20 schematically illustrates an example apparatus having a plurality of elements in accordance with certain embodiments described herein.

FIG. 20 schematically illustrates an example apparatus 500 having a plurality of elements 520 in accordance with certain embodiments described herein. The body 510 shown in FIG. 20 has a plurality of apertures 512 or openings which serve as indicators of treatment site locations. Each element 520 is positioned at a corresponding one of the plurality of apertures 512 and serves as an optical window. In certain embodiments, the plurality of elements 520 comprises at least about 10 elements 520, while in certain other embodiments, the plurality of elements 520 comprises 20 elements 520. In certain other embodiments, the plurality of elements 520 comprises between 15 and 25 elements 520.

In certain embodiments, the body 510 comprises a hood, as schematically illustrated by FIG. 20, while in other embodiments, the body 510 comprises a cap or has another configuration which is wearable on the patient's head and serves as a support for orienting the elements 520 on the patient's head. In certain embodiments, the body 510 comprises a stretchable material which generally conforms to the patient's scalp. In certain embodiments, the body 510 comprises nylon-backed polychloroprene. In certain embodiments, the body 510 is available in different sizes (e.g., small, medium, large) to accommodate different sizes of heads. In certain embodiments, the apparatus 500 is disposable after a single use to advantageously avoid spreading infection or disease between subsequent patients.

Figure 21:
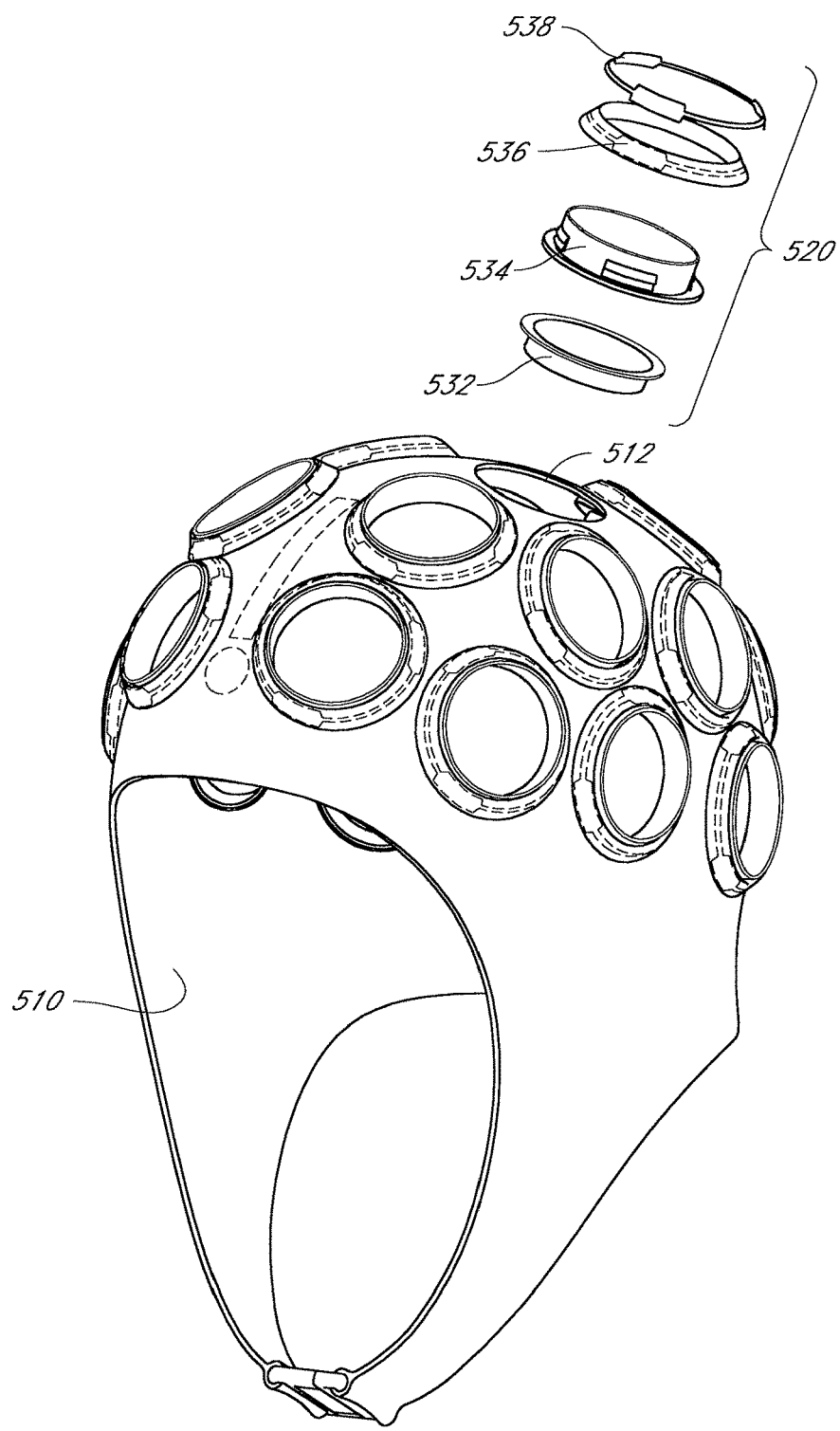
FIG. 21 schematically illustrates an example element in an exploded view.

FIG. 21 schematically illustrates an example element 520 in an exploded view. The example element 520 comprises an optical component 532, a first support ring 534, a second support ring 536, and a label 538. Other configurations of the element 520 are also compatible with certain embodiments described herein.

Figure 22A:
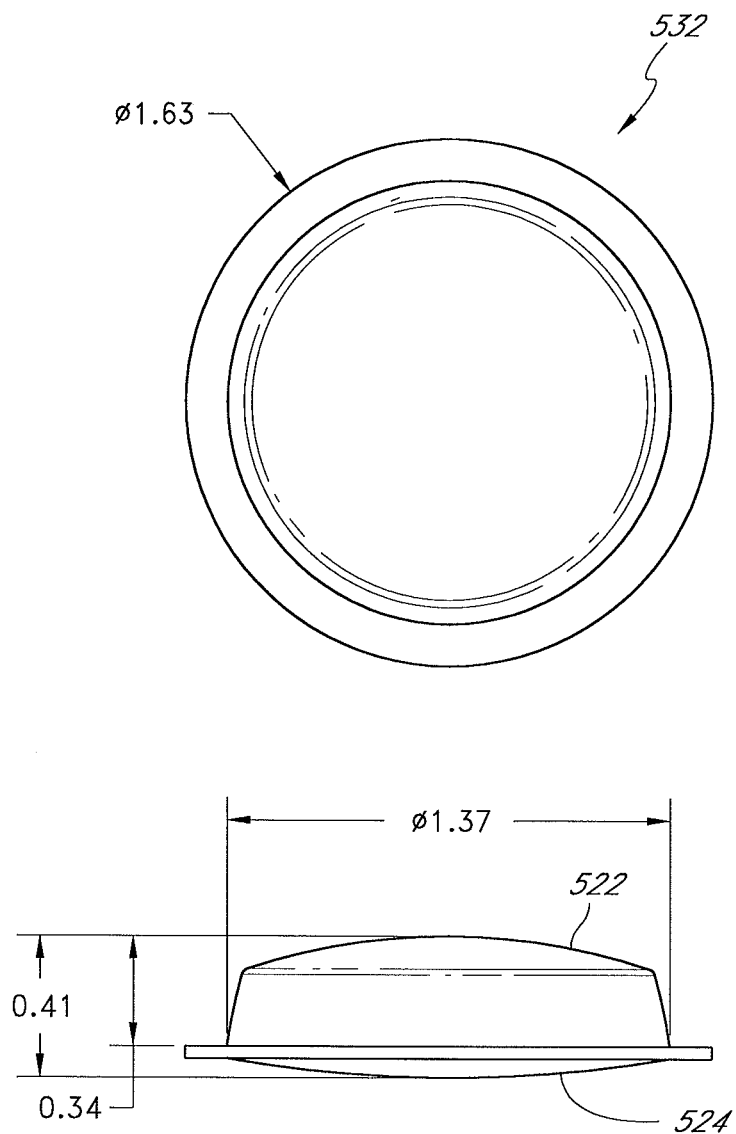
FIG. 22A schematically illustrates an example optical component with example dimensions in inches.

In certain embodiments, the optical component 532 comprises a substantially transmissive (e.g., substantially transparent or substantially translucent) bag comprising a flexible material (which can be biocompatible). FIG. 22A schematically illustrates an example optical component 532 with example dimensions in inches. The bag of FIG. 22A comprises an inflatable container which contains a substantially transmissive liquid (e.g., water) or gel. In certain embodiments, the bag has an outer diameter within a range between about 0.5 inch and about 3 inches. For example, the bag of FIG. 22A has an outer diameter of about 1.37 inches. In certain embodiments, the bag has a volume in a range between about 2 cubic centimeters and about 50 cubic centimeters.

Both the bag and the liquid contained within the bag are substantially transmissive to light having wavelengths to be applied to the patient's brain (e.g., wavelength of approximately 810 nanometers). In certain embodiments, the liquid has a refractive index which substantially matches a refractive index of the patient's scalp, thereby advantageously providing an optical match between the element 520 and the patient's scalp. While the example optical component 532 of FIG. 22A comprises a single bag, in certain other embodiments, the optical component 532 comprises a plurality of bags filled with a substantially transparent liquid.

Figure 22B:
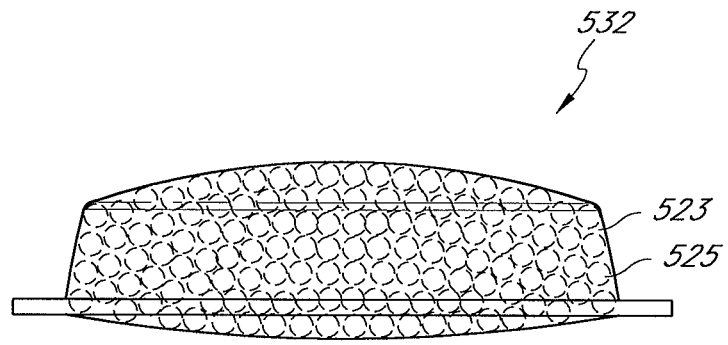
FIGS. 22B and 22C schematically illustrate other example optical components in accordance with certain embodiments described herein.
Figure 22C:
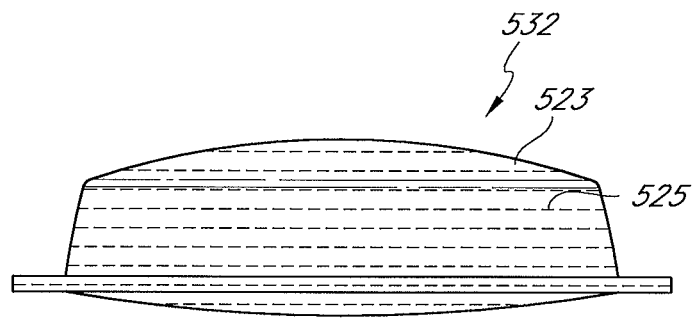

FIGS. 22B and 22C schematically illustrate other example optical components 532 in which the bag contains a composite material. For example, in FIGS. 22B and 22C, the bag contains a first material 523 and a second material 525. In certain embodiments, the first material 523 comprises a soft, substantially transmissive, thermally insulative material (e.g., gel). Example gels compatible with certain embodiments described herein include, but are not limited to, OC-431A-LVP, OCK-451, and OC-462 optical gels available from Nye Corporation of Fairhaven, Mass. In certain embodiments, the second material 525 comprises a rigid, substantially transmissive, thermally conductive material (e.g., silica).

In certain embodiments, as schematically illustrated in FIG. 22B, the second material 525 comprises a plurality of balls distributed within the first material 523. The balls of certain embodiments have diameters less than about 2 millimeters. In certain other embodiments, as schematically illustrated in FIG. 22C, the first material 523 comprises a first plurality of layers and the second material 525 comprises a second plurality of layers. The first plurality of layers is stacked with the second plurality of layers, thereby forming a stack having alternating layers of the first material 523 and the second material 525. In certain embodiments, each layer of the first plurality of layers has a thickness less than about 2 millimeters and each layer of the second plurality of layers has a thickness less than about 2 millimeters. In certain other embodiments, each layer of the first plurality of layers and each layer of the second plurality of layers has a thickness less than about 0.5 millimeter. Other configurations of the first material 523 and the second material 525 within the optical component 532 are also compatible with certain embodiments described herein.

The optical component 532 of certain embodiments advantageously deforms in response to pressure applied to the first portion 522 and the second portion 524. For example, without a load being applied, the optical component 532 of FIG. 22A has a thickness of approximately 0.41 inch, but with approximately four pounds of applied pressure, the optical component 532 of FIG. 22A has a thickness of approximately 0.315 inch. The first portion 522 of the optical component 532 advantageously deforms to substantially conform to a portion of the patient's skull to which the optical component 532 is pressed. For example, in certain embodiments, the first portion 522 comprises a conformable surface of the optical component 532. Thus, in certain such embodiments, the optical component 532 advantageously provides an interface with the patient's scalp which is substantially free of air gaps. The second portion 524 of the optical component 532 advantageously deforms to substantially conform to a light source being pressed thereon. For example, in certain embodiments, the second portion 524 comprises a conformable surface of the optical component 532. Thus, in certain such embodiments, the optical component 532 advantageously provides an interface with the light source which is substantially free of air gaps.

In certain embodiments, the optical component 532 advantageously serves as a heat sink to inhibit temperature increases at the patient's scalp caused by light which is transmitted through the optical component 532. In certain such embodiments, the optical component 532 has a sufficiently high heat capacity to provide an effective heat sink to the patient's scalp. For example, for a bag filled with water (which has a heat capacity of approximately 4180 joules/kilogram-K), a generally disk-shaped bag having a diameter of approximately 32 millimeters and a thickness of approximately 10 millimeters has a sufficient volume, and a sufficient heat capacity, to provide an effective heat sink. Thus, in certain embodiments, each element 520 advantageously inhibits temperature increases at the patient's scalp caused by the light transmitted through the element 520.

FIG. 23 schematically illustrates an example first support ring 534 with example dimensions in inches. In certain embodiments, the first support ring 534 comprises a substantially rigid material. Examples of compatible materials include, but are not limited to, plastic (e.g., acrylonitrile butadiene styrene or ABS). As illustrated in FIG. 23, the first support ring 534 of certain embodiments is configured to be mounted in a corresponding aperture 512 of the body 510. The example first support ring 534 illustrated in FIG. 23 comprises a generally flat portion 542, an annular portion 544, and one or more protrusions 546 configured to connect to the second support ring 536, described more fully below. The generally flat portion 542 has an outer diameter which is larger than the diameter of the corresponding aperture 512 of the body 510 and is configured to be mechanically coupled to the body 510 (e.g., by adhesive). The annular portion 544 has an outer diameter which is smaller than or equal to the diameter of the corresponding aperture 512 of the body 510 and is configured to fit through the aperture 512. The one or more protrusions 546 extend generally radially from the annular portion 544 such that the overall width of the protrusions 546 and the annular portion 544 is larger than the diameter of the corresponding aperture 512 of the body 510.

Figure 24:
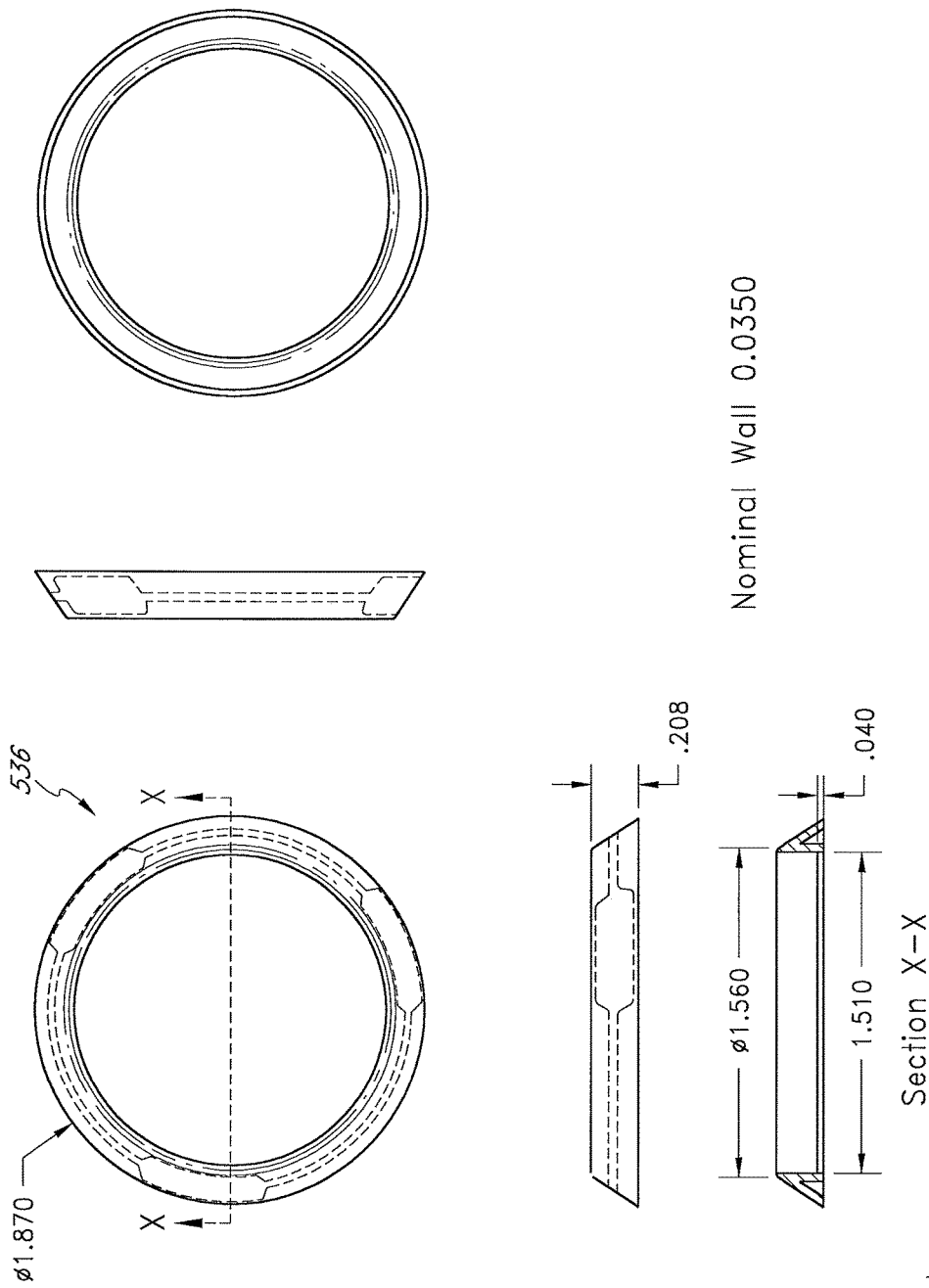
FIG. 24 schematically illustrates an example second support ring with example dimensions in inches.

FIG. 24 schematically illustrates an example second support ring 536 with example dimensions in inches. In certain embodiments, the second support ring 536 comprises a substantially rigid material. Examples of compatible materials include, but are not limited to, plastic (e.g., acrylonitrile butadiene styrene or ABS). As illustrated in FIG. 24, the second support ring 536 of certain embodiments is configured to be connected to the one or more protrusions 546 and the annular portion 544 of the first support ring 534. In certain embodiments, the second support ring 536 comprises one or more recesses (not shown) which are configured to fit with the one or more protrusions 546 of the first support ring 534. In certain such embodiments, the first support ring 534 and the second support ring 536 interlock together to advantageously hold the element 520 in place on the body 510. In certain other embodiments, the first support ring 534 comprises one or more recesses configured to mate with one or more corresponding protrusions of the second support ring 536.

Figure 25:
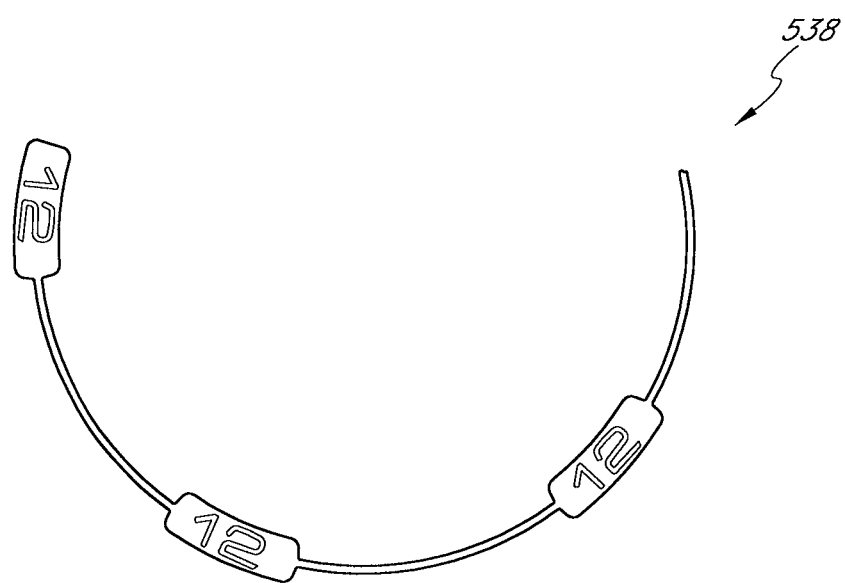
FIG. 25 schematically illustrates an example label compatible with certain embodiments described herein.

FIG. 25 schematically illustrates an example label 538 compatible with certain embodiments described herein. The labels 538 advantageously provide one or more numbers, letters, or symbols (e.g., bar codes) to each of the elements 520 to distinguish the various elements 520 from one another. In certain such embodiments, the labels 538 comprise a vinyl material and are mechanically coupled to the second support ring 536 (e.g., by adhesive) so as to be visible to users of the light therapy apparatus. Other types of labels 538 are also compatible with embodiments disclosed herein, including but not limited to, labels 538 which are painted or etched onto an outside surface of the second support ring 536.

Figure 26A:
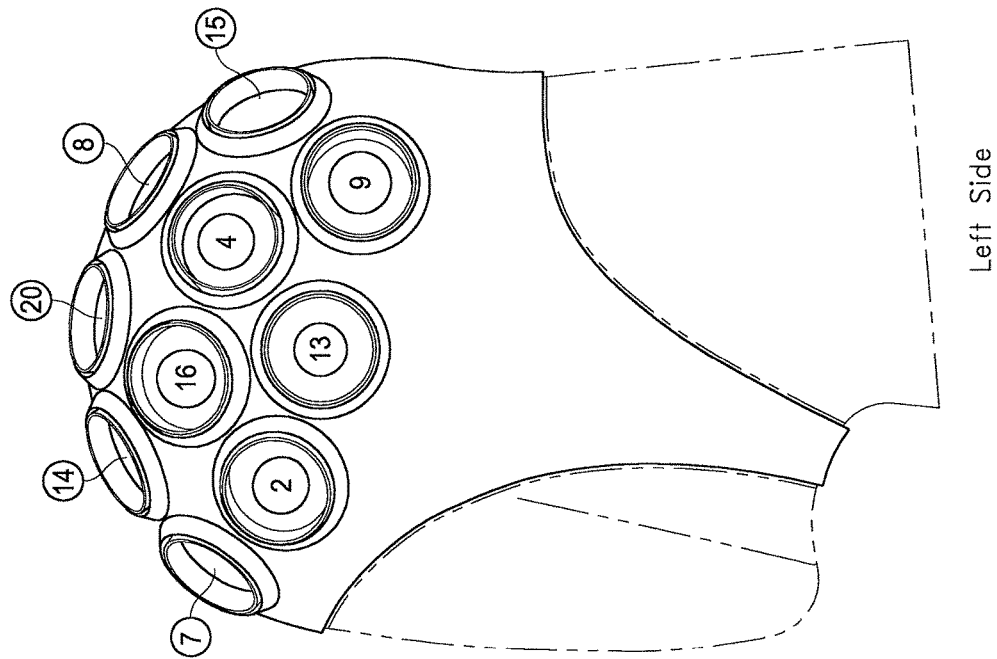
FIGS. 26A and 26B schematically illustrate an example labeling configuration for the apparatus on the left-side and right-side of the apparatus.
Figure 26B:
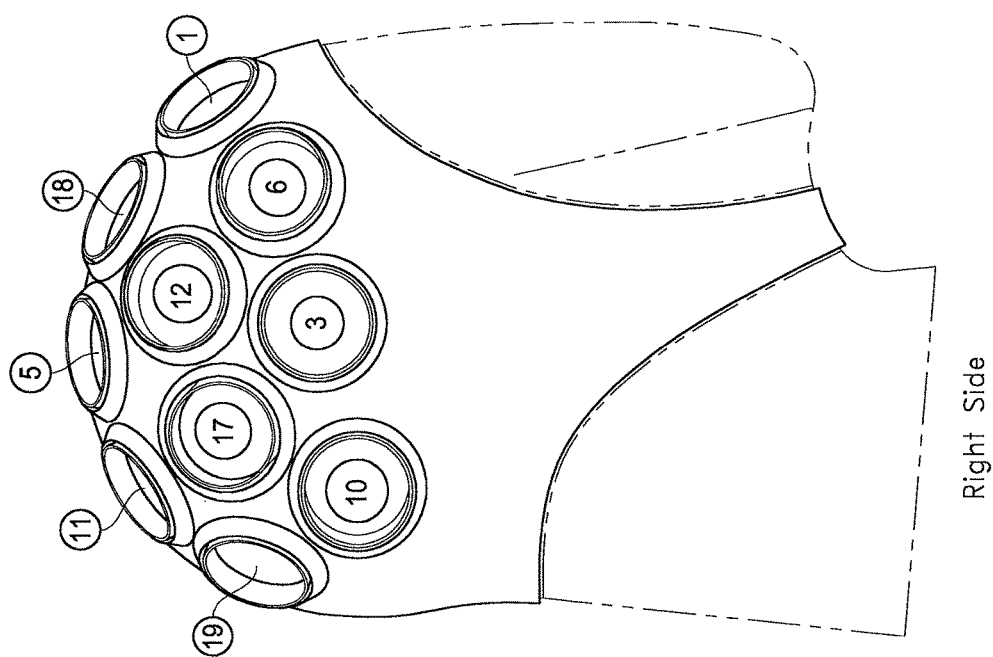
Figure 26C:
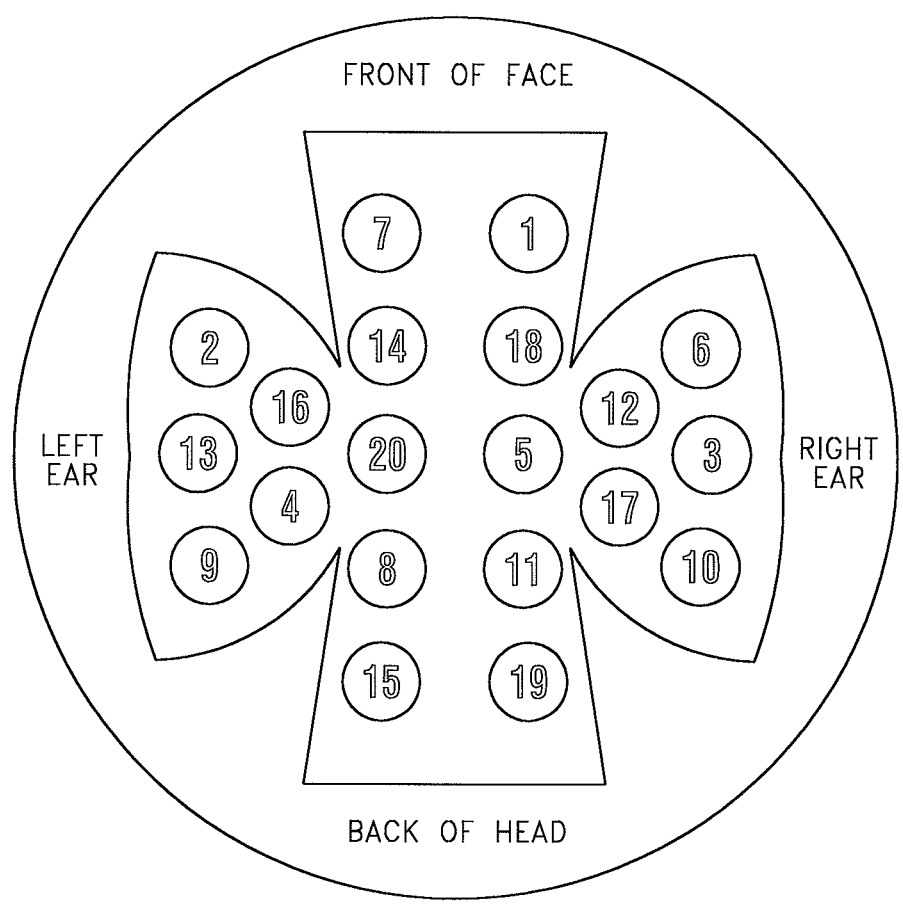
FIG. 26C schematically illustrates the example labeling configuration of FIGS. 26A and 26B from above a flattened view of the apparatus.

FIGS. 26A and 26B schematically illustrate the left-side and right-side of the apparatus 500, respectively, showing an example labeling configuration for the apparatus 500. FIG. 26C schematically illustrates the example labeling configuration of FIGS. 26A and 26B from above a flattened view of the apparatus 500. The labeling convention of FIGS. 26A-26C is compatible with irradiation of both halves of the patient's brain. Other labeling conventions are also compatible with embodiments described herein.

In certain embodiments, the labels 538 are advantageously used to guide an operator to irradiate the patient's brain at the various treatment sites sequentially at each of the treatment sites one at a time through the elements 520 in a predetermined order using a light source which can be optically coupled to sequential elements 520. For example, for the labeling configuration of FIGS. 26A-26C, the operator can first irradiate element "1," followed by elements "2," "3,", "4," etc. to sequentially irradiate each of the twenty treatment sites one at a time. In certain such embodiments, the order of the elements 520 is selected to advantageously reduce temperature increases which would result from sequentially irradiating elements 520 in proximity to one another.

In certain embodiments, the labels 538 are advantageously used to keep track of which elements 520 have been irradiated and which elements 520 are yet to be irradiated. In certain such embodiments, at least a portion of each label 538 (e.g., a pull-off tab) is configured to be removed from the apparatus 500 when the corresponding element 520 has been irradiated. In certain embodiments, the label 538 has a code sequence which the operator enters into the controller prior to irradiation so as to inform the controller of which element 520 is next to be irradiated. In certain other embodiments, each label 538 comprises a bar code or a radio-frequency identification device (RFID) which is readable by a sensor electrically coupled to the controller. The controller of such embodiments keeps track of which elements 520 have been irradiated, and in certain such embodiments, the controller only actuates the light source when the light source is optically coupled to the proper element 520.

Figure 27A:
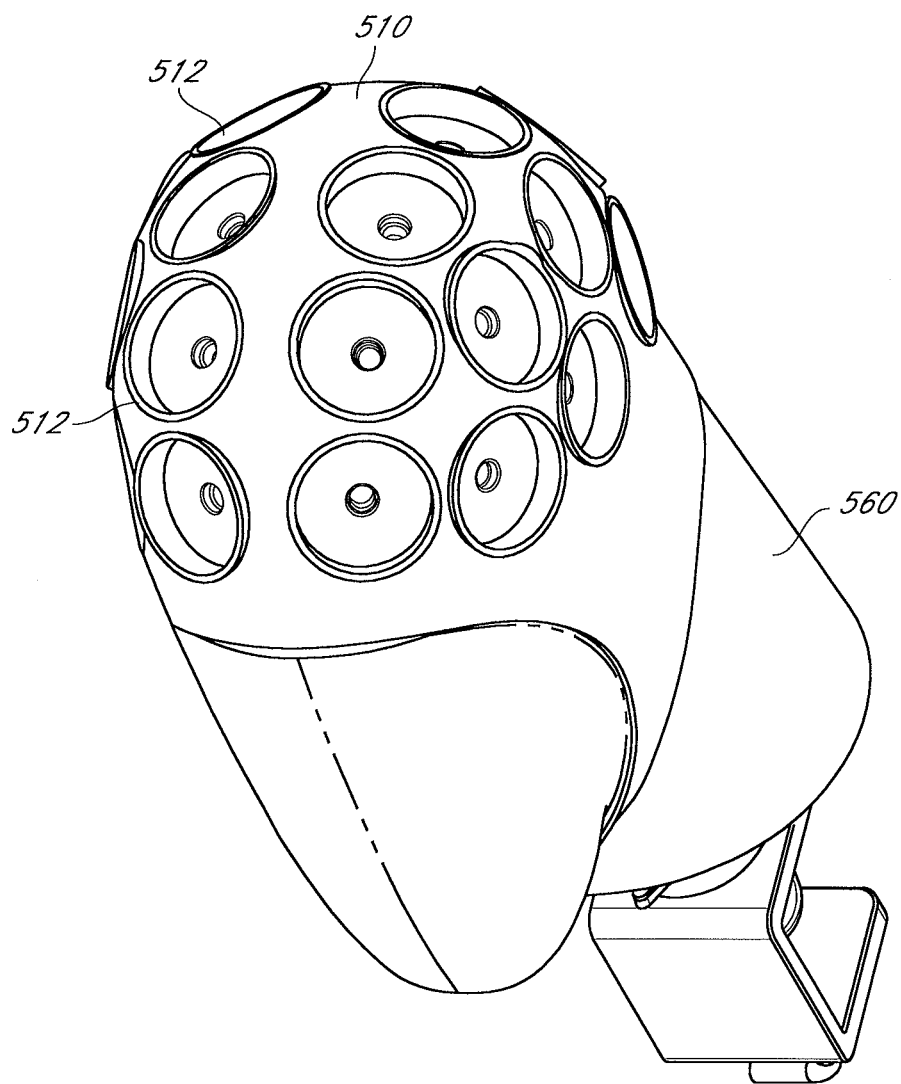
FIGS. 27A-27E schematically illustrate various stages of structures formed during the fabrication of the apparatus of FIGS. 20-25.
Figure 27B:
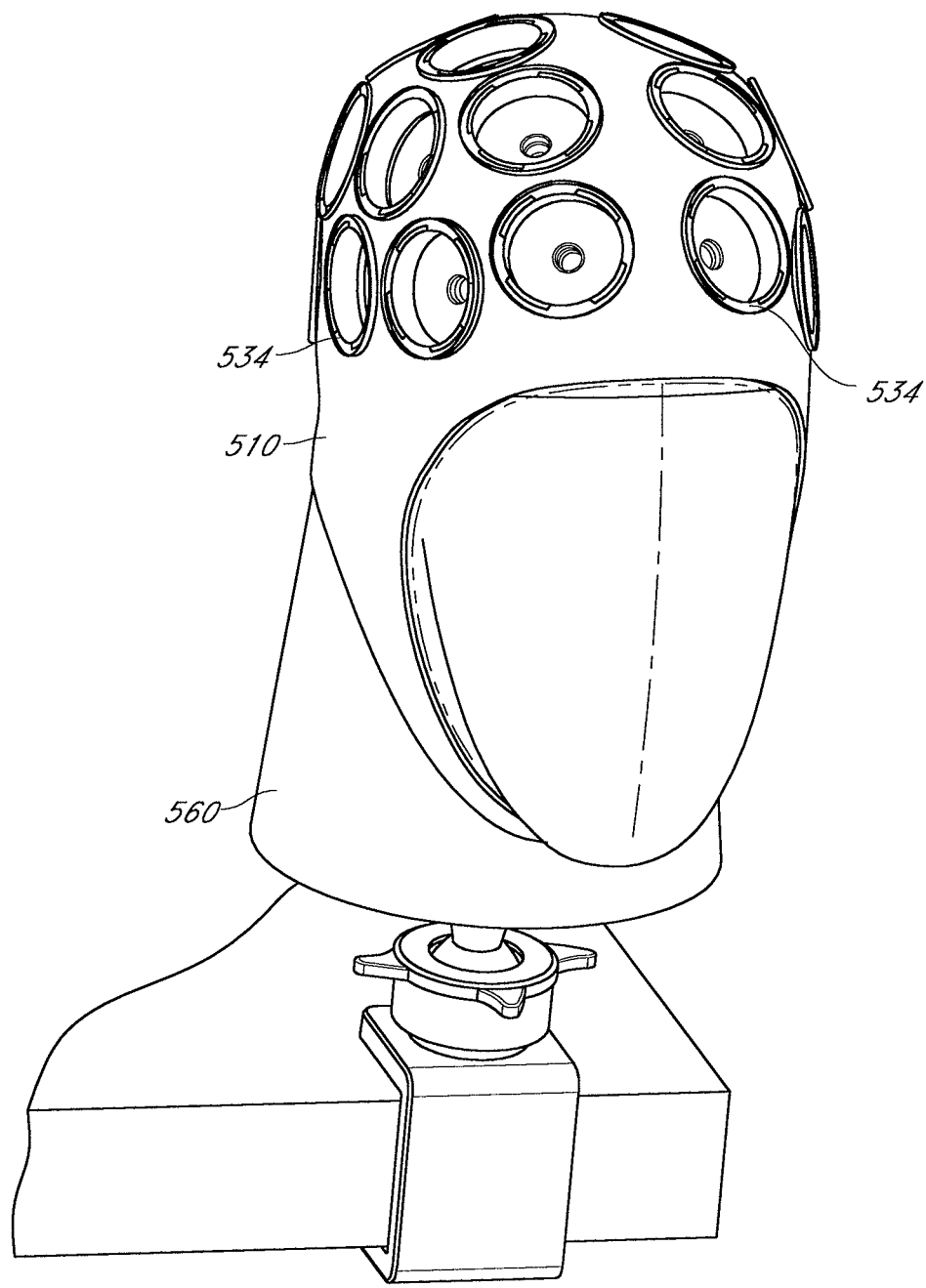
Figure 27C:
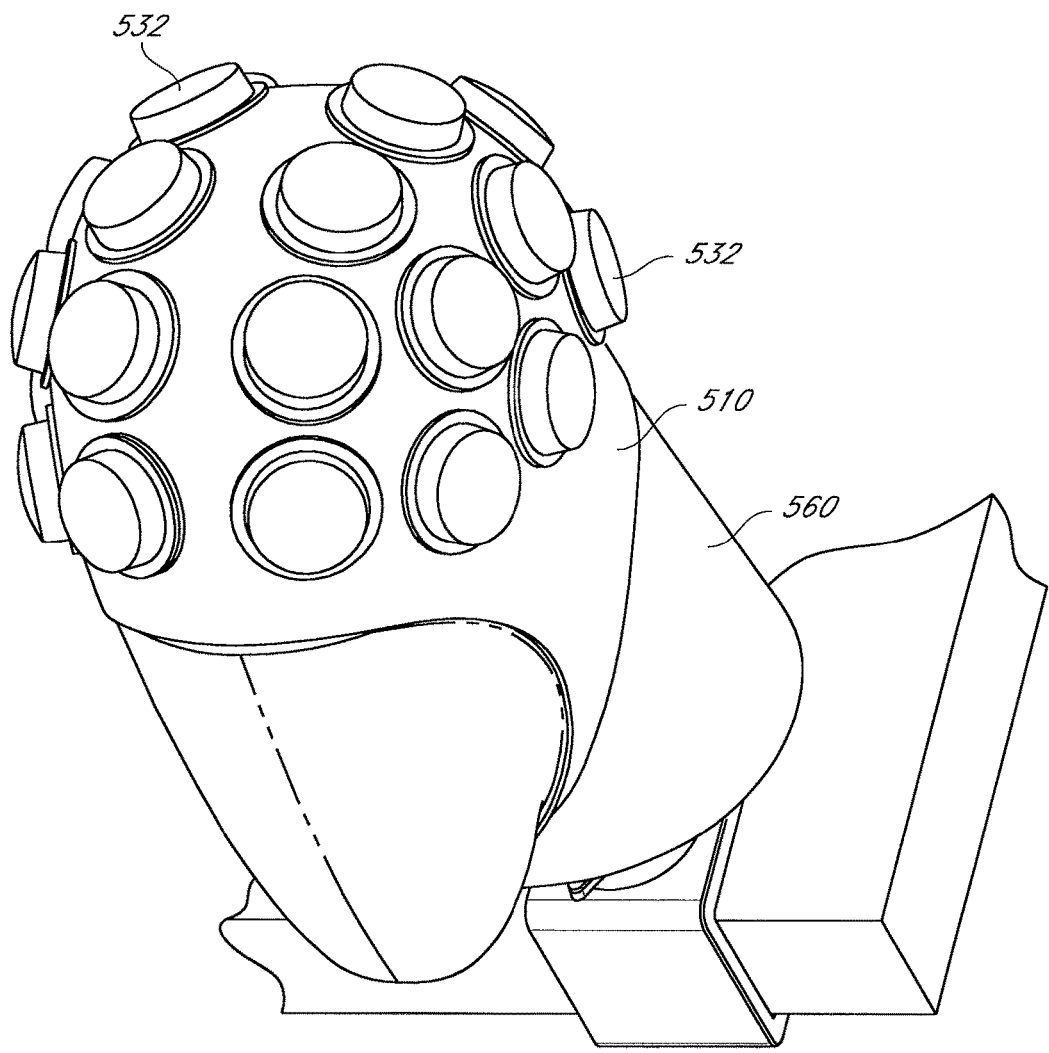
Figure 27D:
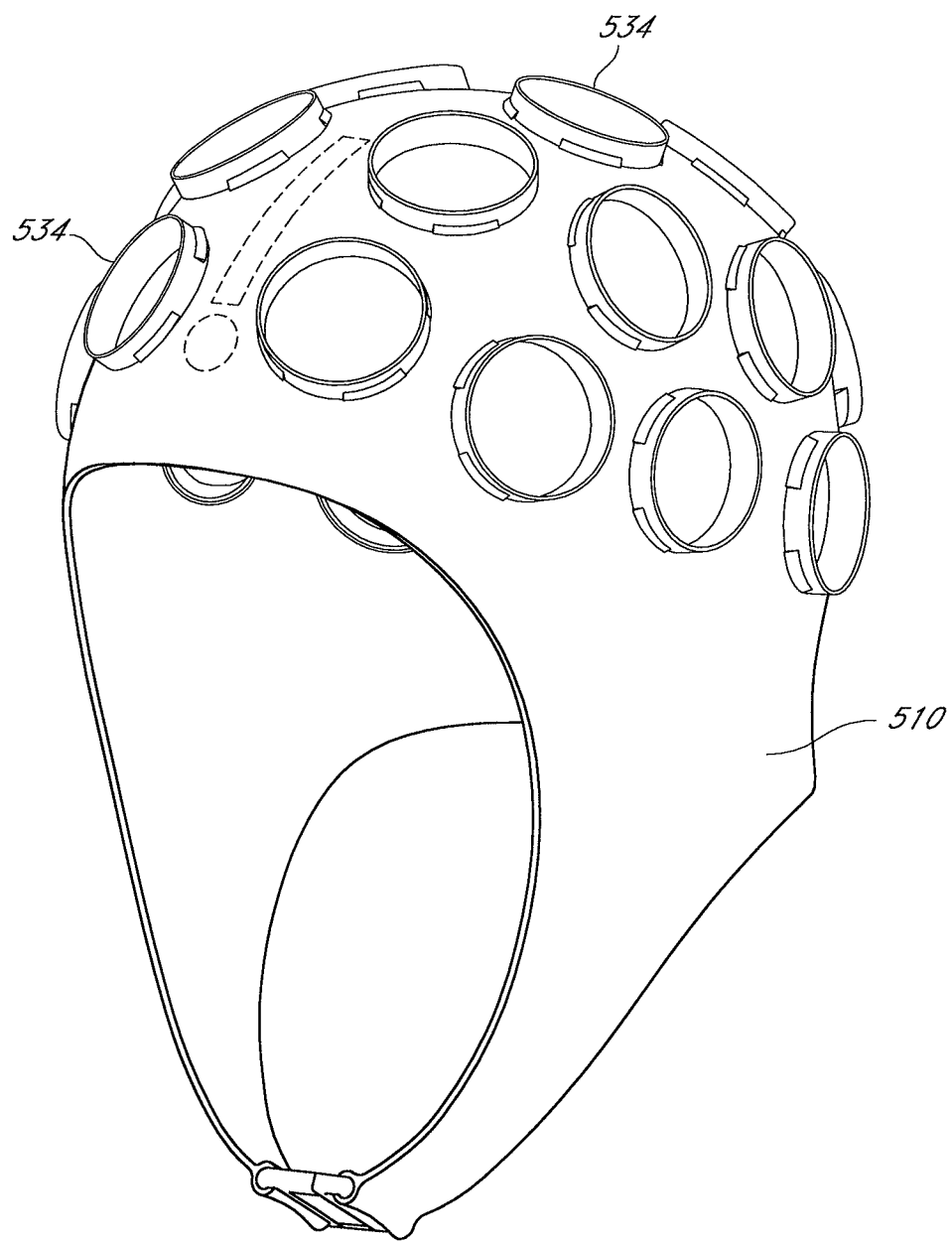
Figure 27E:
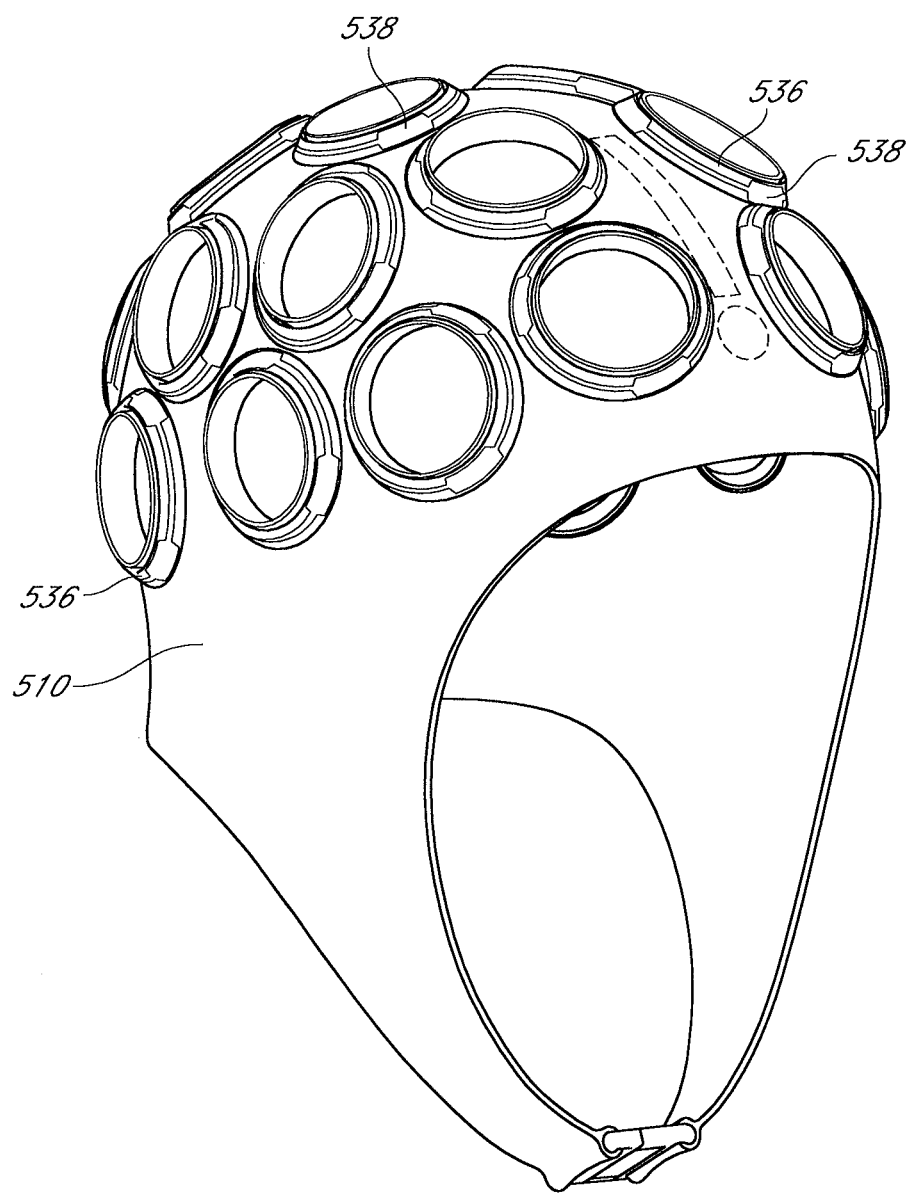

FIGS. 27A-27E schematically illustrate various stages of structures formed during the fabrication of the apparatus 500 of FIGS. 20-25. FIG. 27A schematically illustrates the body 510 mounted on a mannequin head fixture 560. The body 510 is mounted in an inside-out configuration and is shown in FIG. 27A after each of the apertures 512 has been cut in the body 510. In each of the apertures 512, a first support ring 534 is connected to the body 510, as shown in FIG. 27B. In certain embodiments, a layer of adhesive (e.g., CA40 Scotch-Weld™ instant adhesive available from 3M Company of Saint Paul, Minn.) is applied to a surface of the flat portion 542 which is then pressed onto the body 510 with the annular portion 544 extending through the aperture 512. FIG. 27C schematically illustrates the optical components 532 mounted on each of the first support rings 534. In certain embodiments, a layer of adhesive (e.g., Loctite® 3105 ultraviolet-cured adhesive available from Henkel Corporation of Rocky Hill, Conn.) is applied to a surface of the flat portion 542 which is then pressed together with a corresponding surface of the optical component 532 and the adhesive is cured by application of ultraviolet light. FIG. 27D schematically illustrates the body 510 after being removed from the mannequin head fixture 560 and returned to an right-side-out configuration. FIG. 27E schematically illustrates the apparatus 500 after the second support rings 536 have been mounted to the first support rings 534 and the labels 538 have been applied to the second support rings 536.

Example Light Emitting Apparatus

Figure 28:
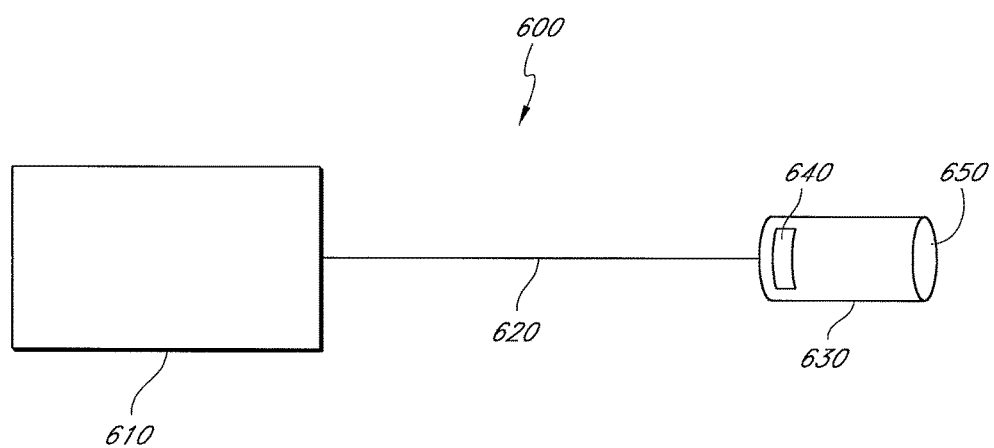
FIG. 28 schematically illustrates an apparatus which emits light for irradiating a patient's skin to treat portions of a patient's body underneath the patient's skin.

FIG. 28 schematically illustrates an apparatus 600 which emits light for irradiating a patient's skin to treat portions of a patient's body underneath the patient's skin. The apparatus 600 comprises a source 610 of light having a wavelength which is substantially transmitted by the patient's skin. The apparatus 600 further comprises an optical conduit 620 optically coupled to the source 610. The apparatus 600 further comprises an optical device 630 optically coupled to the optical conduit 620. The optical device 630 comprises an optical diffuser 640 optically coupled to the optical conduit 620. The optical device 630 further comprises an output optical element 650 comprising a rigid and substantially thermally conductive material. The output optical element 650 is optically coupled to the optical conduit 620 (e.g., via the optical diffuser 640). A portion of the light transmitted through the patient's skin irradiates at least a portion of the patient's body underneath the patient's skin with an efficacious power density of light.

In certain embodiments, the source 610 comprises a laser which emits light having at least one wavelength in a range between about 630 nanometers and about 1064 nanometers. The laser of certain other embodiments emits light having at least one wavelength in a range between about 780 nanometers and about 840 nanometers. In certain embodiments, the laser emits light having a center wavelength of approximately 808 nanometers. The laser of certain embodiments is capable of generating up to approximately 6 watts of laser light and has a numerical aperture of approximately 0.16.

Figure 29:
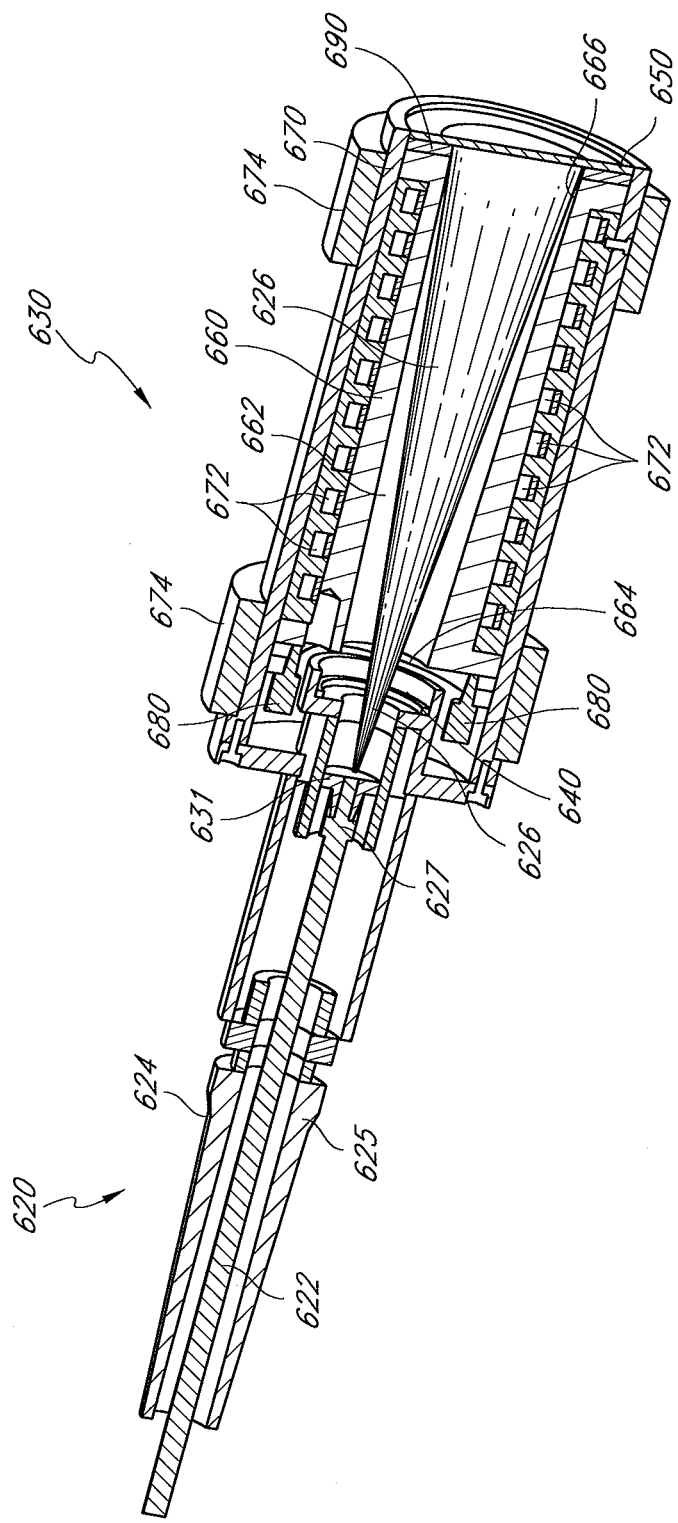
FIG. 29 schematically illustrates an example optical conduit optically coupled to an example optical device.

FIG. 29 schematically illustrates an example optical conduit 620 optically coupled to an example optical device 630. In certain embodiments, the optical conduit 620 comprises an optical fiber 622 and a protective sheath 624 around the optical fiber. The optical fiber 622 of certain embodiments is a step-index optical fiber having a numerical aperture of approximately 0.22 (e.g., a 1-millimeter diameter multimode fiber). In certain embodiments, the optical conduit 620 further comprises an electrically conductive conduit to transmit signals between the optical device 630 and the source 610 (e.g., from trigger switches or temperature sensors within the optical device 630) and/or to provide electrical power to the optical device 630 (e.g., for a thermoelectric cooler).

In certain embodiments, the protective sheath 624 comprises a strain relief apparatus 625 and a SMA connector 627 which mechanically couples to a corresponding adjustable SMA mount 631 of the optical device 630. The protective sheath 624 of certain embodiments has a plurality of rigid segments, with each segment having a generally cylindrical tubular shape and a longitudinal axis. Each segment is articulately coupled to neighboring segments such that an angle between the longitudinal axes of neighboring segments is limited to be less than a predetermined angle. In certain embodiments, the protective sheath 624 allows the optical conduit 620 to be moved and to bend, but advantageously limits the radius of curvature of the bend to be sufficiently large to avoid breaking the optical fiber 622 therein.

The example optical device 630 schematically illustrated by FIG. 29 comprises an optical diffuser 640 and an output optical element 650 (e.g., a lens). In certain embodiments, the output optical element 650 comprises glass (e.g., BK7 glass) which is substantially optically transmissive at wavelengths which are substantially transmitted by skin, but is not substantially thermally conductive. In certain other embodiments, the output optical element 650 is rigid, substantially optically transmissive at wavelengths which are substantially transmitted by skin, and substantially thermally conductive.

In certain embodiments, the output optical element 650 has a front surface facing generally towards the patient's scalp and a back surface facing generally away from the patient's scalp. In certain embodiments, the front surface is adapted to be placed in contact with either the skin or with an intervening material in contact with the skin during irradiation. In certain such embodiments, the thermal conductivity of the output optical element 650 is sufficient to allow heat to flow from the front surface of the output optical element 650 to a heat sink in thermal communication with the back surface of the output optical element 650. In certain embodiments, the output optical element 650 conducts heat from the front surface to the back surface at a sufficient rate to prevent, minimize, or reduce damage to the skin or discomfort to the patient from excessive heating of the skin due to the irradiation.

The existence of air gaps between the output optical element 650 and the scalp can create a problem in controlling the heating of the skin by the irradiation. In certain embodiments, the output optical element 650 is placed in contact with the skin of the scalp so as to advantageously avoid creating air gaps between the output optical element 650 and the skin. In certain other embodiments in which an intervening material is in contact with the skin and with the output optical element 650, the output optical element 650 is placed in contact with the intervening material so as to advantageously avoid creating air gaps between the output optical element 650 and the intervening material or between the intervening material and the skin.

In certain embodiments, the thermal conductivity of the output optical element 650 has a thermal conductivity of at least approximately 10 watts/meter-K. In certain other embodiments, the thermal conductivity of the output optical element 650 is at least approximately 15 watts/meter-K. Examples of materials for the output optical element 650 in accordance with certain embodiments described herein include, but are not limited to, sapphire which has a thermal conductivity of approximately 23.1 watts/meter-K, and diamond which has a thermal conductivity between approximately 895 watts/meter-K and approximately 2300 watts/meter-K.

In certain embodiments, the optical diffuser 640 receives and diffuses light 626 emitted from the optical coupler 620 to advantageously homogenize the light beam prior to reaching the output optical element 650. Generally, tissue optics is highly scattering, so beam non-uniformity less than approximately 3 millimeters in size has little impact on the illumination of the patient's cerebral cortex. In certain embodiments, the optical diffuser 640 advantageously homogenizes the light beam to have a non-uniformity less than approximately 3 millimeters. In certain embodiments, the optical diffuser 640 has a diffusing angle of approximately one degree.

In certain embodiments, the output optical element 650 receives the diffused light 626 propagating from the optical diffuser 640 and emits the light 626 out of the optical device 630. In certain embodiments, the output optical element 650 comprises a collimating lens. In certain embodiments, the light beam emitted from the output optical element 650 has a nominal diameter of approximately 30 millimeters. The perimeter of the light beam used to determine the diameter of the beam is defined in certain embodiments to be those points at which the intensity of the light beam is $1/e^2$ of the maximum intensity of the light beam. The maximum-useful diameter of certain embodiments is limited by the size of the patient's head and by the heating of the patient's head by the irradiation. The minimum-useful diameter of certain embodiments is limited by heating and by the total number of treatment sites that could be practically implemented. For example, to cover the patient's skull with a beam having a small beam diameter would correspondingly use a large number of treatment sites. In certain embodiments, the time of irradiation per treatment site can be adjusted accordingly to achieve a desired exposure dose. In certain embodiments, the beam intensity profile has a semi-Gaussian profile, while in certain other embodiments, the beam intensity profile has a "top hat" profile.

In certain embodiments, the optical device 630 comprises an optical lens which receives light from the optical conduit 620 and transmits the light to the output optical element 650. In certain such embodiments, the output optical element 650 comprises an optical diffuser. In certain embodiments, the output optical element 650 comprises both an optical lens and an optical diffuser.

In certain embodiments, the optical device 630 further comprises a heat sink 660 thermally coupled to the output optical element 650 (e.g., by a thermal adhesive, such as Resinlab EP1200 available from Ellsworth Adhesives of Germantown, Wis.). By having the thermally conductive output optical element 650 thermally coupled to the heat sink 660, certain embodiments advantageously provide a conduit for heat conduction away from the treatment site (e.g., the skin). In certain embodiments, the output optical element 650 is pressed against the patient's skin and transfers heat away from the treatment site. In certain other embodiments in which the output optical element 650 is pressed against an element 520 which contacts the patient's skin, as described above, the element 520 advantageously provides thermal conduction between the patient's skin and the output optical element 650.

As schematically illustrated by FIG. 29, the heat sink 660 of certain embodiments comprises a reflective inner surface 662, a first end 664, and a second end 666. The heat sink 660 is positioned so that light 626 from the optical diffuser 640 is transmitted into the first end 664, through the heat sink 660, out of the second end 666, and to the output optical element 650. The inner surface 662 of certain embodiments is substantially cylindrical, while for certain other embodiments, the inner surface 662 is substantially conical. In certain embodiments having a conical inner surface 662, the inner surface 662 at the first end 664 has a first inner diameter and the inner surface 662 at the second end 666 has a second inner diameter larger than the first inner diameter.

In certain embodiments, the heat sink 660 comprises aluminum and the reflective inner surface is gold-plated. In certain other embodiments, the reflective inner surface 662 is roughened (e.g., by grit sandblasting) to reduce specular reflections of light from the inner surface 662.

In certain embodiments, as schematically illustrated by FIG. 29, the optical device 630 further comprises a housing 670 comprising a plurality of ventilation slots 672. The ventilation slots 672 of certain embodiments allow air flow to remove heat from the heat sink 660, thereby cooling the heat sink 660.

In certain embodiments, the housing 670 is sized to be easily held in one hand (e.g., having a length of approximately 5½ inches). The housing 670 of certain embodiments further comprises one or more protective bumpers 674 comprising a shock-dampening material (e.g., rubber). The housing 670 of certain embodiments is configured so that the optical device 630 can be held in position and sequentially moved by hand to irradiate selected portions of the patient's skin.

In certain embodiments, as schematically illustrated by FIG. 29, the optical device 630 further comprises at least one trigger switch 680. The trigger switch 680 is electrically coupled to the source 610. The trigger switch 680 of certain embodiments is actuated by pressing the output optical element 650 against a surface. The source 610 of certain embodiments is responsive to the trigger switch 680 by emitting light only when the trigger switch 680 is actuated. Therefore, in certain such embodiments, to utilize the optical device 630, the output optical element 650 is pressed against the patient's skin or against an element 520, such as described above.

In certain embodiments, the optical device 630 further comprises a thermoelectric cooler 690 thermally coupled to the output optical element 650, as schematically illustrated by FIG. 29. The thermoelectric cooler 690 of certain embodiments has a cool side thermally coupled to the output optical element 650 and a hot side which is thermally coupled to the heat sink 660. The thermoelectric cooler 690 of certain embodiments advantageously removes heat from the output optical element 650. Certain embodiments of the optical device 630 comprising a thermoelectric cooler 690 which actively cools the patient's skin thereby advantageously avoiding large temperature gradients at the patient's skin which would otherwise cause discomfort to the patient. In certain embodiments, the optical device 630 further comprises one or more temperature sensors (e.g., thermocouples, thermistors) which generate electrical signals indicative of the temperature of the output optical element 650 or other portions of the optical device 630.

Figure 30:
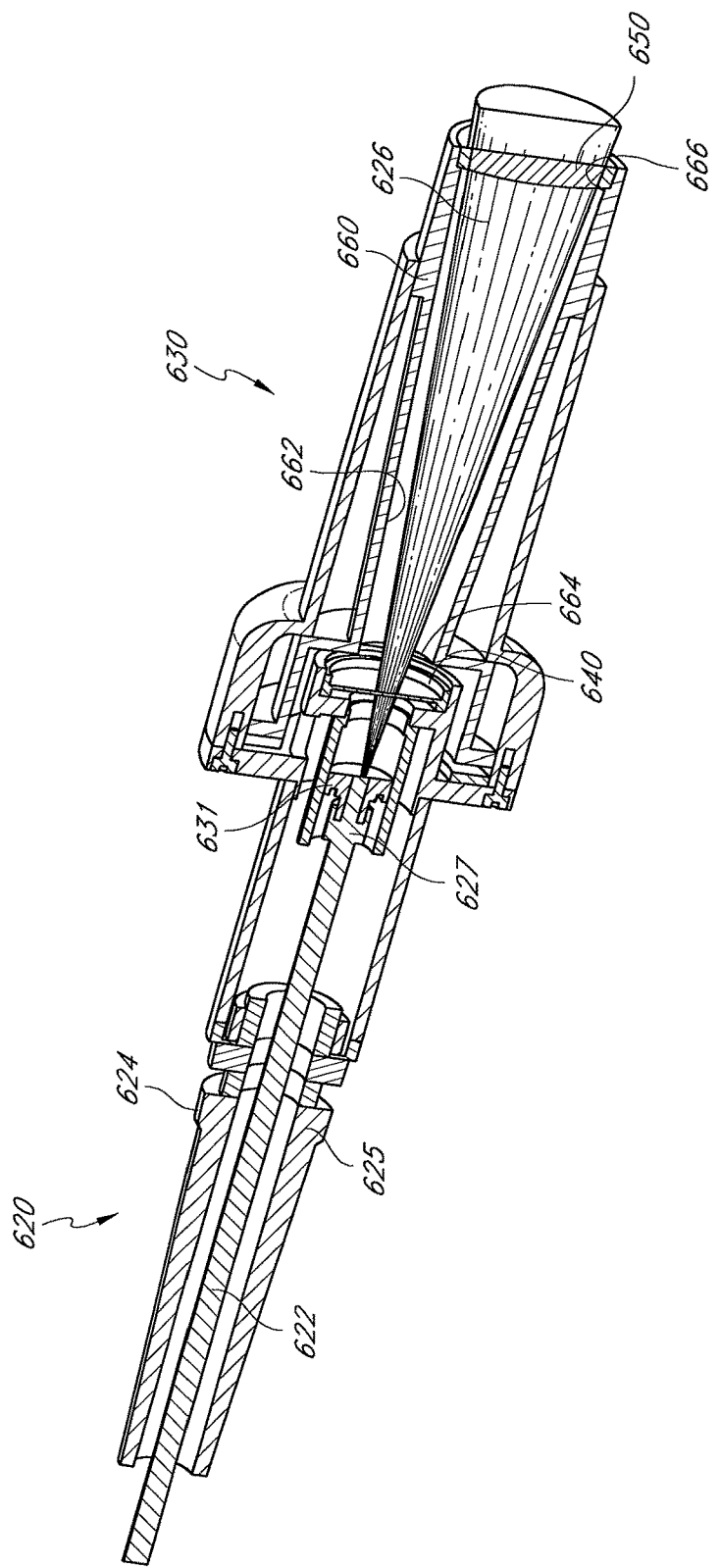
FIG. 30 schematically illustrates a simplified optical device compatible with certain embodiments described herein.

FIG. 30 schematically illustrates a simplified optical device 630 compatible with certain embodiments described herein. The optical device 630 of FIG. 30 has a smaller heat sink 660 and does not have a thermoelectric cooler. As schematically illustrated by FIG. 30, the heat sink 660 of certain embodiments comprises a reflective conical inner surface 662 having a first end 664 with a first inner diameter and a second end 666 with a second inner diameter larger than the first inner diameter. In certain embodiments, the optical device 630 of FIG. 30 is advantageously smaller, lighter, and more easily maneuvered by hand than the optical device 630 of FIG. 29.

Figure 31A:
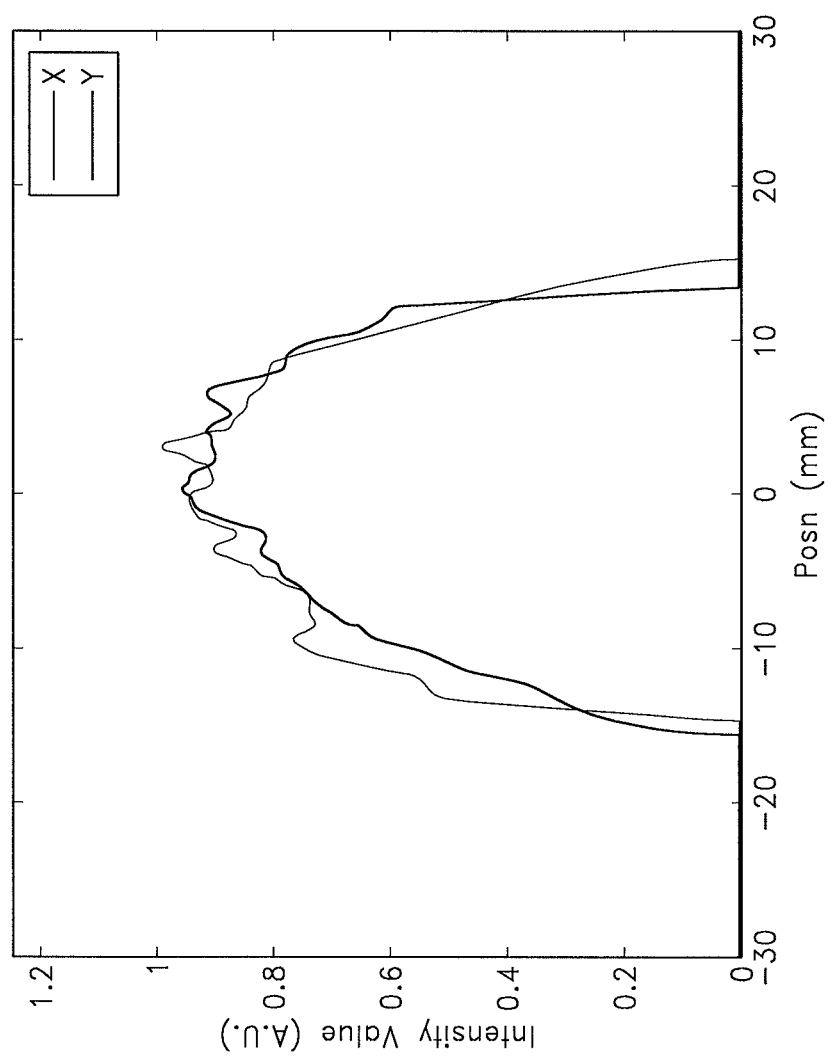
FIG. 31A illustrates two beam profile cross-sections of a light beam emitted from the optical device of FIG. 29 with the planes of the two cross-sections of FIG. 31A generally perpendicular to one another and to the output optical element.
Figure 31B:
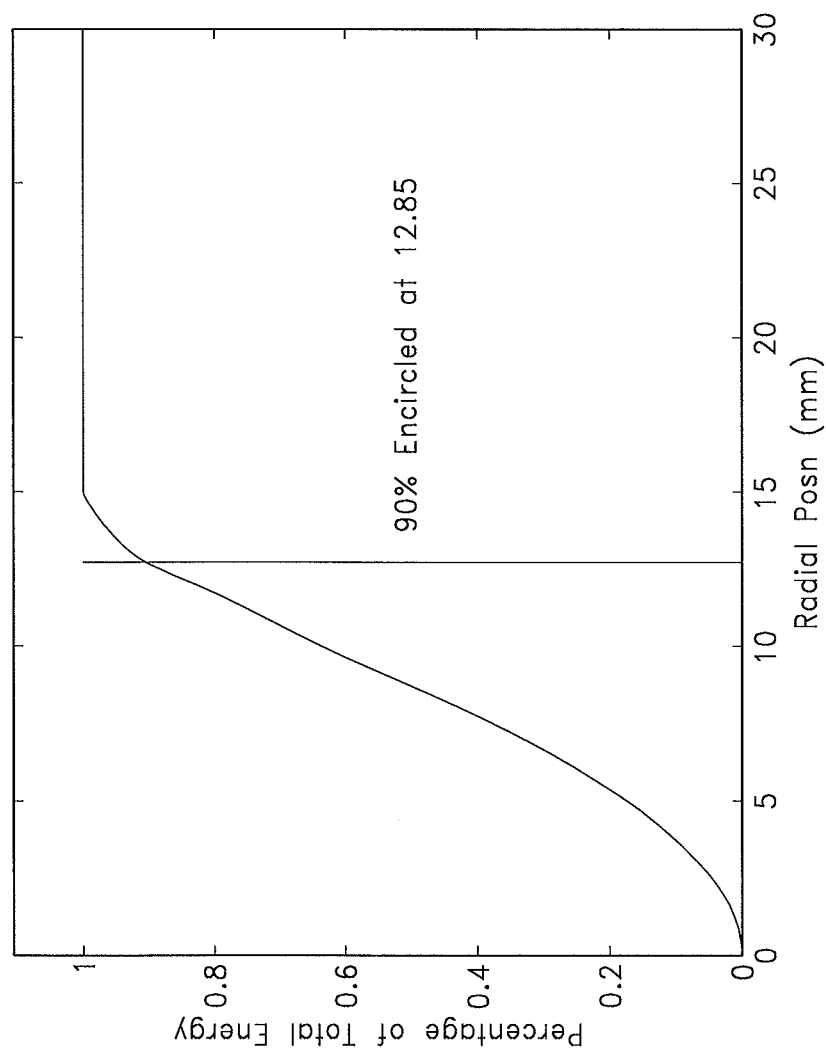
FIG. 31B illustrates the encircled energy of a light beam emitted from the optical device of FIG. 29.

FIG. 31A illustrates two beam profile cross-sections of a light beam emitted from the optical device 630 of FIG. 29 with the planes of the two cross-sections of FIG. 31A generally perpendicular to one another and to an output optical element 650 comprising a lens. The beam diameter of FIG. 31A is approximately 30 millimeters. FIG. 31B illustrates the encircled energy of a light beam emitted from the optical device 630 of FIG. 29. Approximately 90% of the encircled energy falls within a diameter of approximately 25.7 millimeters.

Figure 32A:
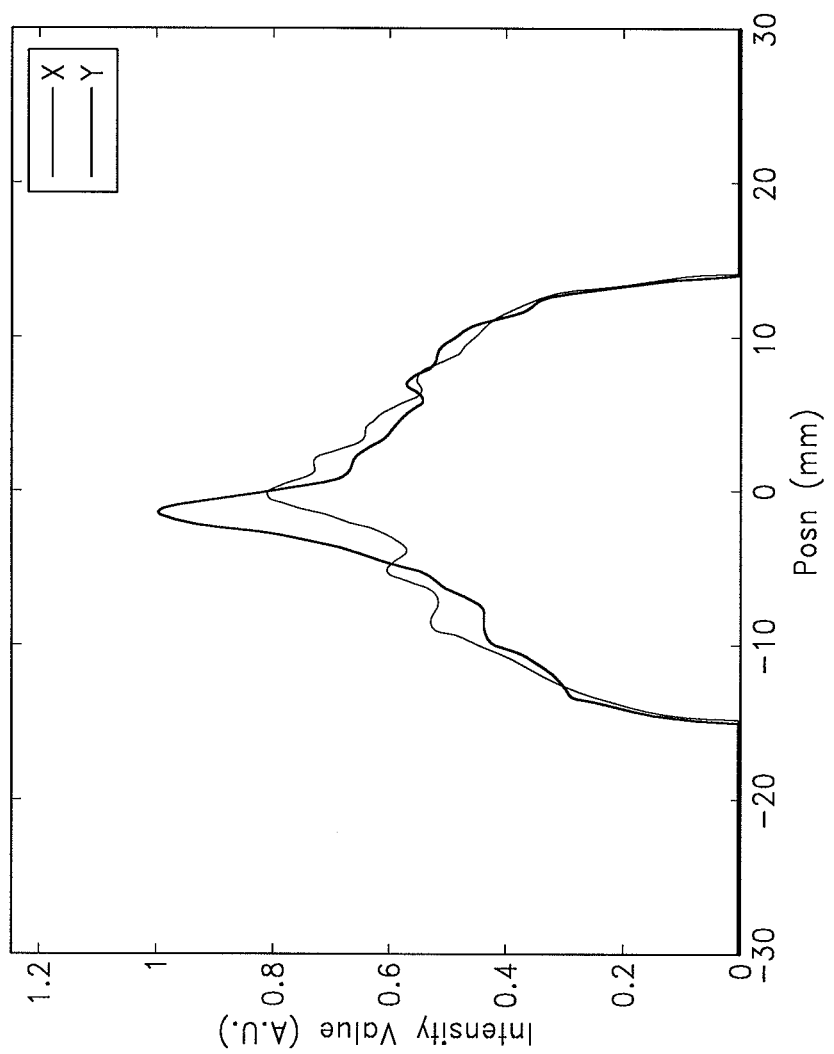
FIG. 32A illustrates two beam profile cross-sections of a light beam emitted from the optical device of FIG. 30 having a smooth gold-plated conical inner surface.
Figure 32B:
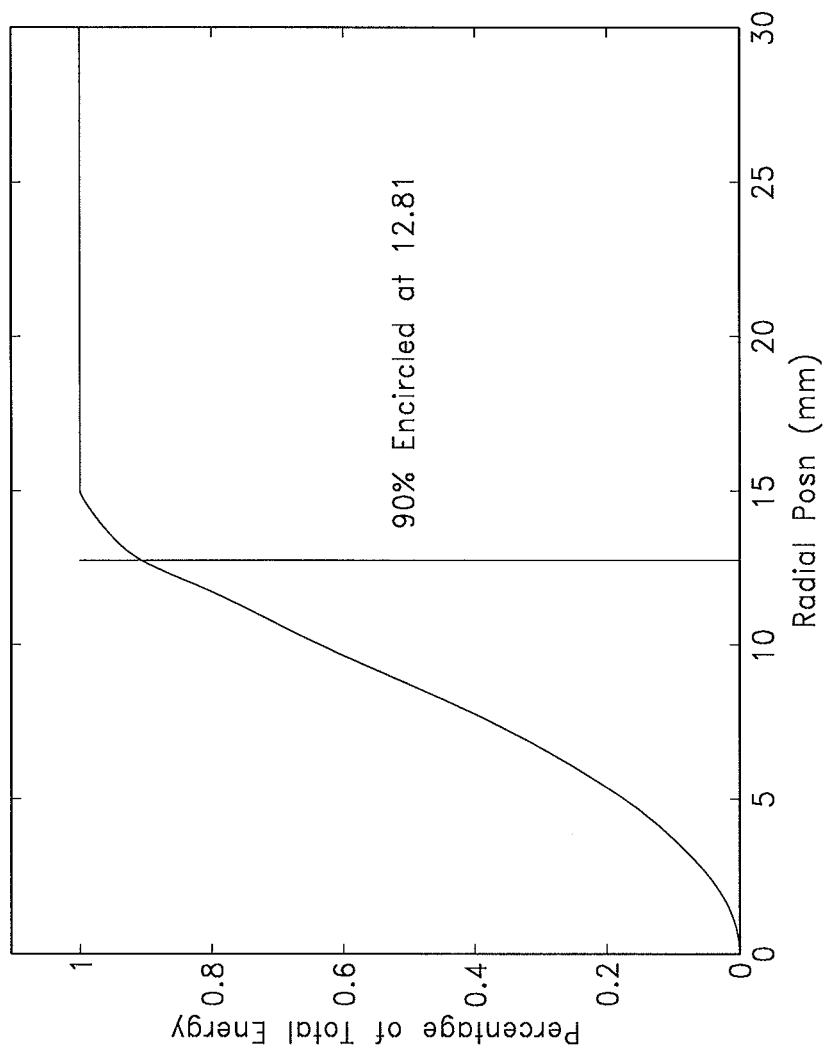
FIG. 32B illustrates the encircled energy of a light beam emitted from the optical device of FIG. 30.

FIG. 32A illustrates two beam profile cross-sections of a light beam emitted from the optical device 630 of FIG. 30 having a smooth gold-plated conical inner surface 662. The planes of the two cross-sections of FIG. 32A are generally perpendicular to one another and to the output optical element 650. The beam diameter of FIG. 32A is approximately 30 millimeters. The light beam has a high flux region near the center of the beam profile. This high flux region qualifies as a hot spot, where a hot spot is defined as regions of the light beam in which the local flux, averaged over a 3 millimeter by 3 millimeter area, is more than 10% larger than the average flux. FIG. 32B illustrates the encircled energy of a light beam emitted from the optical device 630 of FIG. 30. Approximately 90% of the encircled energy falls within a diameter of approximately 25.6 millimeters.

Figure 33:
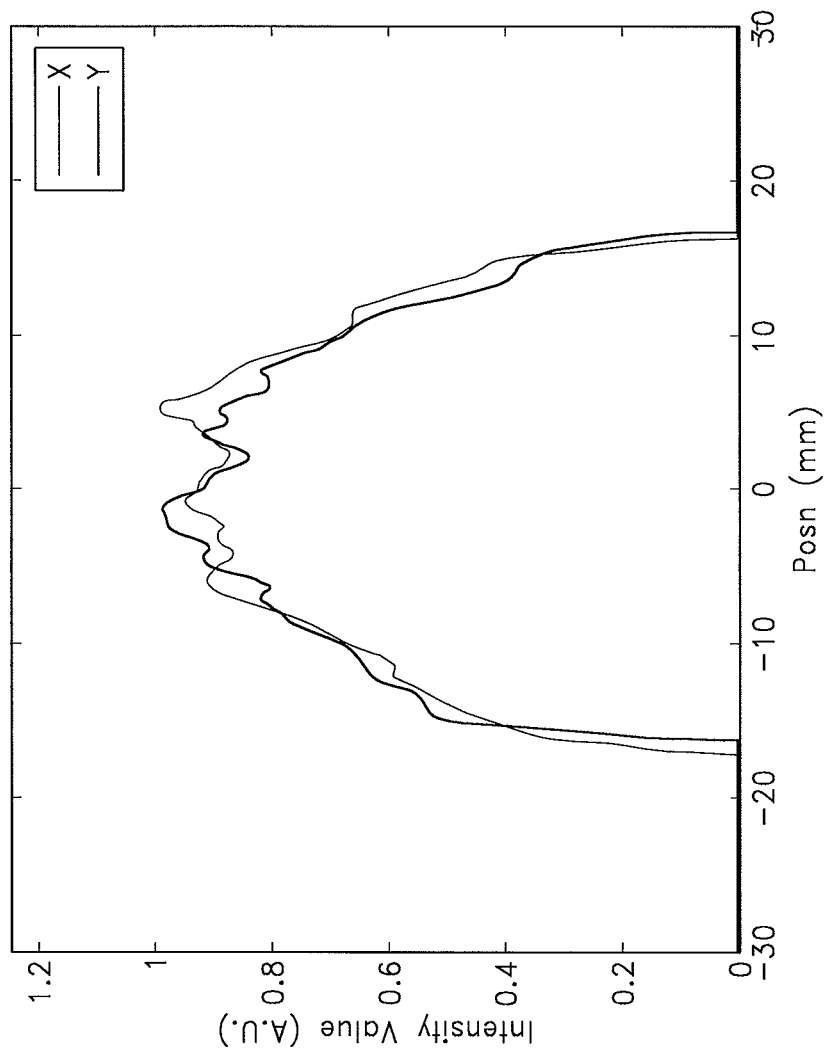
FIG. 33 illustrates two beam profile cross-sections of a light beam emitted from the optical device of FIG. 30 having a grit sandblasted conical inner surface.

In certain embodiments having a smooth inner surface 662, multiple reflections of light emitted from the optical fiber 622 at large enough angles are focused near the output optical element 650, contributing to the hot spot region of the beam profile. FIG. 33 illustrates two beam profile cross-sections of a light beam emitted from the optical device 630 of FIG. 30 having a grit sandblasted conical inner surface 662. This inner surface 662 is roughened to reduce the amount of specular reflections from the inner surface 662. In certain such embodiments, the beam profile does not have a hot spot region. Certain embodiments of the optical device 630 advantageously generate a light beam substantially without hot spots, thereby avoiding large temperature gradients at the patient's skin which would otherwise cause discomfort to the patient.

Figure 34A:
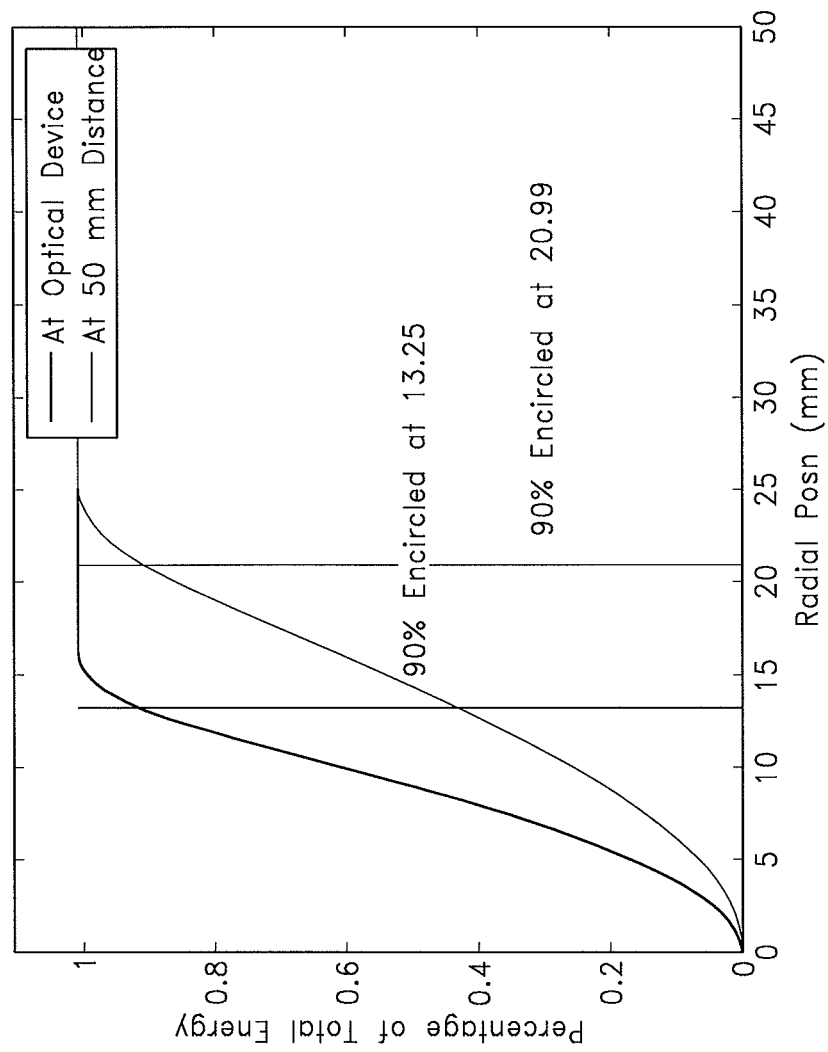
FIGS. 34A and 34B illustrate the beam divergence for the optical device of FIG. 29 and of FIG. 30 (with a sandblasted inner surface), respectively.
Figure 34B:
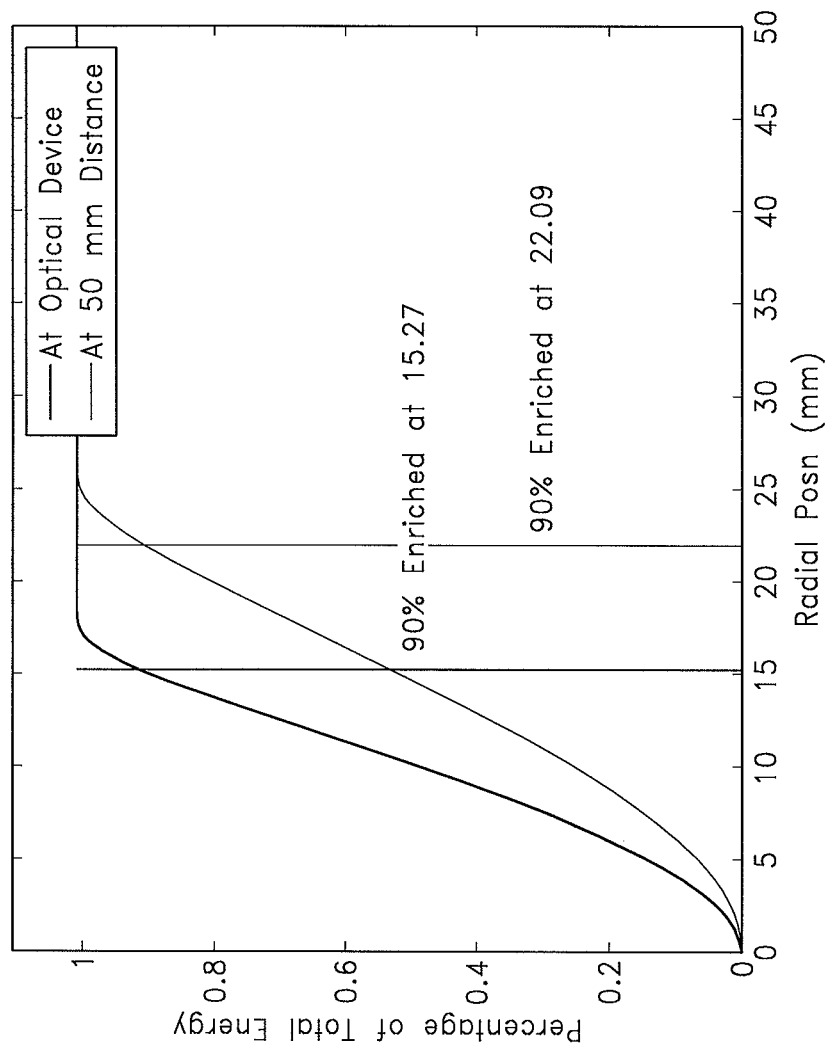

In certain embodiments, the beam divergence emitted from the output optical element 650 is significantly less than the scattering angle of light inside the body tissue being irradiated, which is typically several degrees. FIGS. 34A and 34B illustrate the beam divergence for the optical device 630 of FIG. 29 and of FIG. 30 (with the sandblasted inner surface 622), respectively. The beam divergence was measured by measuring the beam profile at two separate planes and comparing the increase in beam diameter (e.g., the diameter that encircled 90% of the energy) further from the output optical element 650. In certain embodiments, the beam divergence has a full angle of about 12 degrees. The numerical aperture of the optical device 630 of FIG. 29 is approximately 0.152 and the numerical aperture of the optical device 630 of FIG. 30 is approximately 0.134, which equates to a difference of less than approximately 2.5 degrees.

Methods of Light Delivery

In certain embodiments, a patient is treated by identifying a plurality of treatment sites (e.g., at least about 10) on the patient's scalp, directing an electromagnetic radiation source to each of the treatment sites, and propagating electromagnetic radiation from the source to each treatment site. In certain embodiments, the electromagnetic radiation from the source has a wavelength within a range between about 800 nanometers and about 830 nanometers.

As described more fully below, in certain embodiments, the treatment sites are identified using an apparatus comprising a plurality of optically transmissive elements, each of which corresponds to a treatment site. In certain such embodiments, each of the treatment sites is irradiated by electromagnetic radiation from a source placed in contact with each of the optically transmissive elements. In certain other embodiments, the treatment sites are instead identified by other indicia. For example, each of the treatment sites can be identified by markings made on the scalp, or by structures placed in proximity to the scalp. Each of the treatment sites can then be irradiated. In certain embodiments, each of the treatment sites is irradiated by an electromagnetic radiation source in contact with the scalp or in contact with an intervening optically transmissive element which contacts the scalp. In certain other embodiments, the scalp is not contacted by either the electromagnetic radiation source or an intervening element.

In certain embodiments, each of the treatment sites is irradiated using a single electromagnetic radiation source which is sequentially moved from one treatment site to another. In certain other embodiments, a plurality of sources are used to irradiate multiple treatment sites concurrently. In certain such embodiments, the number of sources is fewer than the number of treatments sites, and the plurality of sources are sequentially moved to sequentially irradiate the treatment sites.

Methods of Use of Wearable Apparatus and Light Emitting Apparatus

Figure 35:
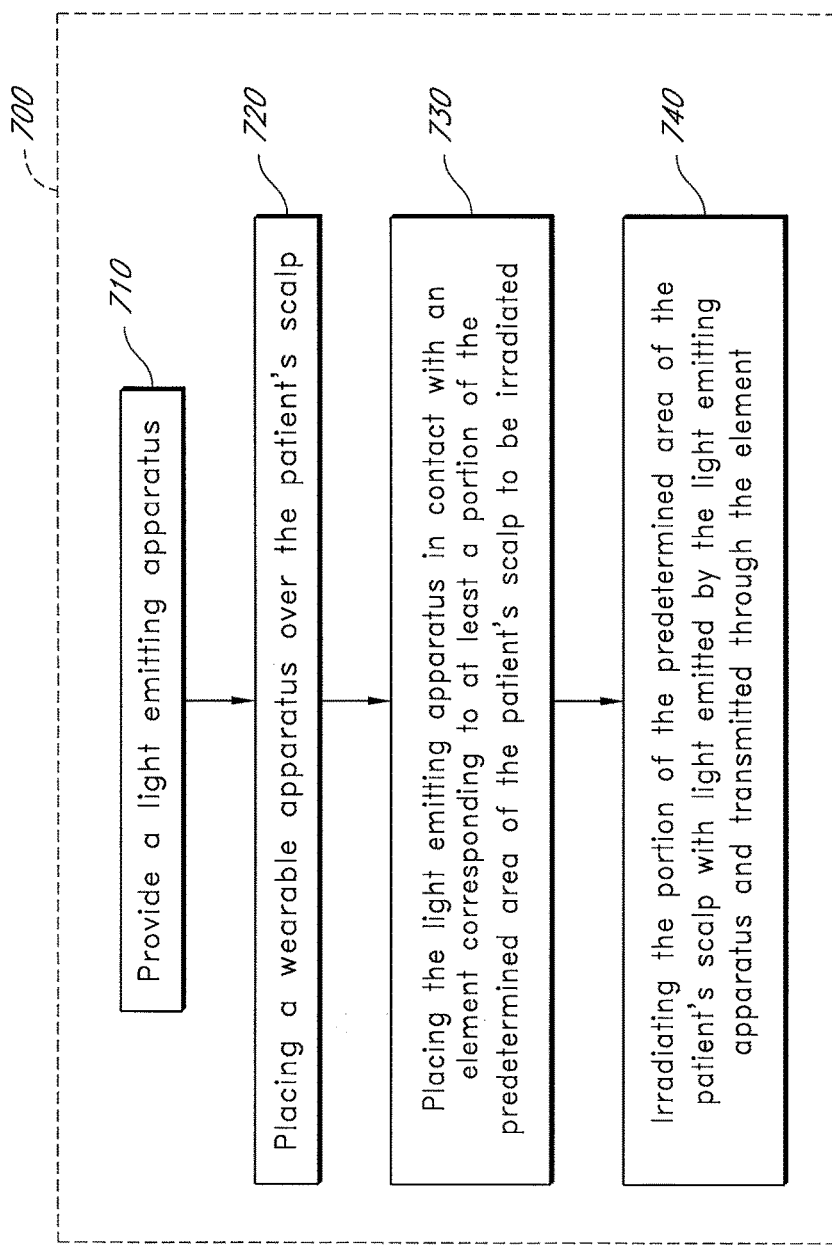
FIG. 35 is a flow diagram of an example method for controllably exposing at least one predetermined area of a patient's scalp to laser light to irradiate the patient's brain.

FIG. 35 is a flow diagram of an example method 700 for controllably exposing at least one predetermined area of a patient's scalp to laser light to irradiate the patient's brain. As described more fully below, the method 700 is described by referring to the wearable apparatus 500 and the light emitting apparatus 600 described herein. Other configurations of a wearable apparatus 500 and a light emitting apparatus 600 are also compatible with the method 700 in accordance with embodiments described herein.

The method 700 comprises providing a light emitting apparatus 600 in an operational block 710. In certain embodiments, the light emitting apparatus 600 comprises a source 610 of laser light, an optical conduit 620 optically coupled to the source 610, and an optical device 630 optically coupled to the optical conduit 620. Other configurations of the light emitting apparatus 600 besides those in FIGS. 28-34 are also compatible with certain embodiments described herein.

The method 700 further comprises placing a wearable apparatus 500 over the patient's scalp in an operational block 720. The apparatus 500 comprises a body 510 and a plurality of elements 520. Each element 520 has a first portion 522 which conforms to a corresponding portion of the patient's scalp when the apparatus 500 is worn by the patient. Each element 520 also has a second portion 524 which conforms to the optical device 630 when the optical device 630 contacts the element 520. Each element 520 is substantially transmissive to laser light emitted by the optical device 630. Other configurations of the wearable apparatus 500 besides those in FIGS. 19-27E are also compatible with certain embodiments described herein.

The method 700 further comprises placing the light emitting apparatus 600 in contact with an element 520 corresponding to at least a portion of the predetermined area of the patient's scalp to be irradiated in an operational block 730. The method 700 further comprises irradiating the portion of the predetermined area of the patient's scalp with light emitted by the light emitting apparatus 600 and transmitted through the element 520 in an operational block 740.

In certain embodiments, providing the light emitting apparatus 600 in the operational block 710 comprises preparing the light emitting apparatus 600 for use to treat the patient. In certain embodiments, preparing the light emitting apparatus 600 comprises cleaning the portion of the light emitting apparatus 600 through which laser light is outputted. In certain embodiments, preparing the light emitting apparatus 600 comprises verifying a power calibration of laser light outputted from the light emitting apparatus 600. Such verification can comprise measuring the light intensity output from the light emitting apparatus 600 and comparing the measured intensity to an expected intensity level.

In certain embodiments, placing the wearable apparatus 500 over the patient's scalp in the operational block 720 comprises preparing the patient's scalp for treatment. For example, in certain embodiments, preparing the patient's scalp for treatment comprises removing hair from the predetermined areas of the patient's scalp to be irradiated. Removing the hair (e.g., by shaving) advantageously reduces heating of the patient's scalp by hair which absorbs laser light from the light emitting apparatus 600. In certain embodiments, placing the wearable apparatus 500 over the patient's scalp in the operational block 720 comprises positioning the wearable apparatus 500 so that each element 520 is in contact with a corresponding portion of the patient's scalp.

In certain embodiments, placing the light emitting apparatus 600 in contact with the element 520 in the operational block 730 comprises pressing the light emitting apparatus 600 to the element 520 so that the first portion 522 of the element 520 conforms to the patient's scalp and the second portion 524 of the element 520 conforms to the light emitting apparatus 600. In certain embodiments, by pressing the light emitting apparatus 600 against the element 520 in this way, pressure is applied to the portion of the patient's scalp in contact with the element 520 so as to advantageously blanch the portion of the patient's scalp in contact with the element 520.

In certain embodiments, irradiating the portion of the predetermined area of the patient's scalp in the operational block 740 comprises triggering the outputting of light from the light emitting apparatus 600 by pressing the light emitting apparatus 600 against the element 520 with a predetermined level of pressure. In certain embodiments, the outputting of light from the light emitting apparatus 600 continues only if a predetermined level of pressure is maintained by pressing the light emitting apparatus 600 against the element 520. In certain embodiments, light is outputted from the light emitting apparatus 600 through the element 520 for a predetermined period of time.

In certain embodiments, the method further comprises irradiating additional portions of the predetermined area of the patient's scalp during a treatment process. For example, after irradiating a first portion of the predetermined area corresponding to a first element 520, as described above, the light emitting apparatus 600 can be placed in contact with a second element 520 corresponding to a second portion of the predetermined area and irradiating the second portion of the predetermined area with light emitted by the light emitting apparatus 600 and transmitted through the element 520. The various portions of the predetermined area of the patient's scalp can be irradiated sequentially to one another in a predetermined sequence. In certain embodiments, the predetermined sequence is represented by indicia corresponding to the elements 520 of the wearable apparatus 500. In certain such embodiments, the laser emitting apparatus 600 comprises an interlock system which interfaces with the indicia of the wearable apparatus 500 to prevent the various portions of the predetermined area from being irradiated out of the predetermined sequence.

In certain embodiments, a system for treating a patient comprises a support (e.g., a wearable apparatus 500 as described herein) for identifying a plurality of sites on a patient's scalp for the application of therapeutic electromagnetic energy in a wavelength range between about 800 nanometers and about 830 nanometers. The system further comprises an instruction for use of the support in combination with an electromagnetic light source (e.g., a light emitting apparatus 600 as described herein) of the therapeutic electromagnetic energy. The instruction for use in certain embodiments comprises instructions compatible with the method 700 described herein.

In certain embodiments, a system for treating a patient comprises an electromagnetic light source (e.g., a light emitting apparatus 600 as described herein). The system further comprises an instruction for use of the electromagnetic radiation source by optically coupling the source to a patient's scalp at a plurality of locations to deliver a therapeutic electromagnetic energy to the patient's brain. The instruction for use in certain embodiments comprises instructions compatible with the method 700 described herein.

Methods of Phototherapy

Preferred methods of phototherapy are based at least in part on the finding described above that, for a selected wavelength, the power density (light intensity or power per unit area, in $W/cm^2$) or the energy density (energy per unit area, in $J/cm^2$, or power density multiplied by the exposure time) of the light energy delivered to tissue is an important factor in determining the relative efficacy of the phototherapy, and efficacy is not as directly related to the total power or the total energy delivered to the tissue. In the methods described herein, power density or energy density as delivered to a portion of the patient's brain 20, which can include the area of infarct after a stroke, appears to be important factors in using phototherapy to treat and save surviving but endangered neurons in a zone of danger surrounding the infarcted area. Certain embodiments apply optimal power densities or energy densities to the intended target tissue, within acceptable margins of error.

In certain embodiments, the apparatus and methods of phototherapy described herein increase the cerebral blood flow of the patient. In certain such embodiments, the cerebral blood flow is increased by 10%, 15%, 20%, or 25% immediately post-irradiation, as compared to immediately prior to irradiation.

In certain embodiments, the apparatus and methods of phototherapy described herein are used to treat strokes or other sources of neurodegeneration. As used herein, the term "neurodegeneration" refers to the process of cell destruction resulting from primary destructive events such as stroke or CVA, as well as from secondary, delayed and progressive destructive mechanisms that are invoked by cells due to the occurrence of the primary destructive event. Primary destructive events include disease processes or physical injury or insult, including stroke, but also include other diseases and conditions such as multiple sclerosis, amylotrophic lateral sclerosis, heat stroke, epilepsy, Alzheimer's disease, dementia resulting from other causes such as AIDS, cerebral ischemia including focal cerebral ischemia, and physical trauma such as crush or compression injury in the CNS, including a crush or compression injury of the brain, spinal cord, nerves or retina, or any acute injury or insult producing neurodegeneration. Secondary destructive mechanisms include any mechanism that leads to the generation and release of neurotoxic molecules, including apoptosis, depletion of cellular energy stores because of changes in mitochondrial membrane permeability, release or failure in the reuptake of excessive glutamate, reperfusion injury, and activity of cytokines and inflammation. Both primary and secondary mechanisms contribute to forming a "zone of danger" for neurons, wherein the neurons in the zone have at least temporarily survived the primary destructive event, but are at risk of dying due to processes having delayed effect.

As used herein, the term "neuroprotection" refers to a therapeutic strategy for slowing or preventing the otherwise irreversible loss of neurons due to neurodegeneration after a primary destructive event, whether the neurodegeneration loss is due to disease mechanisms associated with the primary destructive event or secondary destructive mechanisms.

The term "cognitive function" as used herein refers to cognition and cognitive or mental processes or functions, including those relating to knowing, thinking, learning, perception, memory (including immediate, recent, or remote memory), and judging. Symptoms of loss of cognitive function can also include changes in personality, mood, and behavior of the patient. Diseases or conditions affecting cognitive function include Alzheimer's disease, dementia, AIDS or HIV infection, Cruetzfeldt-Jakob disease, head trauma (including single-event trauma and long-term trauma such as multiple concussions or other traumas which may result from athletic injury), Lewy body disease, Pick's disease, Parkinson's disease, Huntington's disease, drug or alcohol abuse, brain tumors, hydrocephalus, kidney or liver disease, stroke, depression, and other mental diseases which cause disruption in cognitive function, and neurodegeneration.

The term "motor function" as used herein refers to those bodily functions relating to muscular movements, primarily conscious muscular movements, including motor coordination, performance of simple and complex motor acts, and the like.

The term "neurologic function" as used herein includes both cognitive function and motor function.

The terms "cognitive enhancement" and "motor enhancement" as used herein refer to the improving or heightening of cognitive function and motor function, respectively.

The term "neurologic enhancement" as used herein includes both cognitive enhancement and motor enhancement.

As used herein, the term "neuroprotective-effective" as used herein refers to a characteristic of an amount of light energy, wherein the amount is a power density of the light energy measured in $mW/cm^2$. A neuroprotective-effective amount of light energy achieves the goal of preventing, avoiding, reducing, or eliminating neurodegeneration, which should result in cognitive enhancement and/or motor enhancement.

The term "neurologic function enhancement effective" as used herein refers to a characteristic of an amount of light energy, wherein the amount is a power density of the light energy measured in $mW/cm^2$. The amount of light energy achieves the goal of neuroprotection, motor enhancement, and/or cognitive enhancement.

Thus, a method for the treatment of stroke or for the enhancement of neurologic function in a patient in need of such treatment involves delivering a neurologic function enhancement effective amount or a neuroprotective-effective amount of light energy having a wavelength in the visible to near-infrared wavelength range to a target area of the patient's brain 20. In certain embodiments, the target area of the patient's brain 20 includes the area of infarct, i.e. to neurons within the "zone of danger." In other embodiments, the target area includes portions of the brain 20 not within the zone of danger. Without being bound by theory or by a specific mechanism, it is believed that irradiation of healthy tissue in proximity to the zone of danger increases the production of ATP and copper ions in the healthy tissue and which then migrate to the injured cells within the region surrounding the infarct, thereby producing beneficial effects. Additional information regarding the biomedical mechanisms or reactions involved in phototherapy is provided by Tiina I. Karu in "Mechanisms of Low-Power Laser Light Action on Cellular Level", Proceedings of SPIE Vol. 4159 (2000), Effects of Low-Power Light on Biological Systems V, Ed. Rachel Lubart, pp. 1-7, which is incorporated in its entirety by reference herein.

In certain embodiments, delivering the neuroprotective amount of light energy includes selecting a surface power density of the light energy at the scalp 30 corresponding to the predetermined power density at the target area of the brain 20. As described above, light propagating through tissue is scattered and absorbed by the tissue. Calculations of the power density to be applied to the scalp 30 so as to deliver a predetermined power density to the selected target area of the brain 20 preferably take into account the attenuation of the light energy as it propagates through the skin and other tissues, such as bone and brain tissue. Factors known to affect the attenuation of light propagating to the brain 20 from the scalp 30 include, but are not limited to, skin pigmentation, the presence and color of hair over the area to be treated, amount of fat tissue, the presence of bruised tissue, skull thickness, and the location of the target area of the brain 20, particularly the depth of the area relative to the surface of the scalp 30. For example, to obtain a desired power density of 50 mW/cm$^2$ in the brain 20 at a depth of 3 cm below the surface of the scalp 30, phototherapy may utilize an applied power density of 500 mW/cm$^2$. The higher the level of skin pigmentation, the higher the power density applied to the scalp 30 to deliver a predetermined power density of light energy to a subsurface site of the brain 20.

In certain embodiments, treating a patient suffering from the effects of stroke comprises placing the therapy apparatus 10 in contact with the scalp 30 and adjacent the target area of the patient's brain 20. The target area of the patient's brain 20 can be previously identified such as by using standard medical imaging techniques. In certain embodiments, treatment further includes calculating a surface power density at the scalp 30 which corresponds to a preselected power density at the target area of the patient's brain 20. The calculation of certain embodiments includes factors that affect the penetration of the light energy and thus the power density at the target area. These factors include, but are not limited to, the thickness of the patient's skull, type of hair and hair coloration, skin coloration and pigmentation, patient's age, patient's gender, and the distance to the target area within the brain 20. The power density and other parameters of the applied light are then adjusted according to the results of the calculation.

The power density selected to be applied to the target area of the patient's brain 20 depends on a number of factors, including, but not limited to, the wavelength of the applied light, the type of CVA (ischemic or hemorrhagic), and the patient's clinical condition, including the extent of the affected brain area. The power density of light energy to be delivered to the target area of the patient's brain 20 may also be adjusted to be combined with any other therapeutic agent or agents, especially pharmaceutical neuroprotective agents, to achieve the desired biological effect. In such embodiments, the selected power density can also depend on the additional therapeutic agent or agents chosen.

In preferred embodiments, the treatment per treatment site proceeds continuously for a period of about 10 seconds to about 2 hours, more preferably for a period of about 1 to about 10 minutes, and most preferably for a period of about 1 to 5 minutes. For example, the treatment time per treatment site in certain embodiments is about two minutes. In other embodiments, the light energy is preferably delivered for at least one treatment period of at least about five minutes, and more preferably for at least one treatment period of at least ten minutes. The minimum treatment time of certain embodiments is limited by the biological response time (which is on the order of microseconds). The maximum treatment time of certain embodiments is limited by heating and by practical treatment times (e.g., completing treatment within about 24 hours of stroke onset). The light energy can be pulsed during the treatment period or the light energy can be continuously applied during the treatment period.

In certain embodiments, the treatment may be terminated after one treatment period, while in other embodiments, the treatment may be repeated for at least two treatment periods. The time between subsequent treatment periods is preferably at least about five minutes, more preferably at least about 1 to 2 days, and most preferably at least about one week. In certain embodiments in which treatment is performed over the course of multiple days, the apparatus 10 is wearable over multiple concurrent days (e.g., embodiments of FIGS. 1, 3, 9A, 10, and 13). The length of treatment time and frequency of treatment periods can depend on several factors, including the functional recovery of the patient and the results of imaging analysis of the infarct. In certain embodiments, one or more treatment parameters can be adjusted in response to a feedback signal from a device (e.g., magnetic resonance imaging) monitoring the patient.

During the treatment, the light energy may be continuously provided, or it may be pulsed. If the light is pulsed, the pulses are preferably at least about 10 nanosecond long and occur at a frequency of up to about 100 kHz. Continuous wave light may also be used.

The thrombolytic therapies currently in use for treatment of stroke are typically begun within a few hours of the stroke. However, many hours often pass before a person who has suffered a stroke receives medical treatment, so the short time limit for initiating thrombolytic therapy excludes many patients from treatment. In contrast, phototherapy treatment of stroke appears to be more effective if treatment begins no earlier than several hours after the ischemic event has occurred. Consequently, the present methods of phototherapy may be used to treat a greater percentage of stroke patients.

In certain embodiments, a method provides a neuroprotective effect in a patient that had an ischemic event in the brain. The method comprises identifying a patient who has experienced an ischemic event in the brain. The method further comprises estimating the time of the ischemic event. The method further comprises commencing administration of a neuroprotective effective amount of light energy to the brain. The administration of the light energy is commenced no less than about two hours following the time of the ischemic event. In certain embodiments, phototherapy treatment can be efficaciously performed preferably within 24 hours after the ischemic event occurs, and more preferably no earlier than two hours following the ischemic event, still more preferably no earlier than three hours following the ischemic event, and most preferably no earlier than five hours following the ischemic event. In certain embodiments, one or more of the treatment parameters can be varied depending on the amount of time that has elapsed since the ischemic event.

Without being bound by theory or by a specific mechanism, it is believed that the benefit in delaying treatment occurs because of the time needed for induction of ATP production, and/or the possible induction of angiogenesis in the region surrounding the infarct. Thus, in accordance with one preferred embodiment, the phototherapy for the treatment of stroke occurs preferably about 6 to 24 hours after the onset of stroke symptoms, more preferably about 12 to 24 hours after the onset of symptoms. It is believed, however, that if treatment begins after about 2 days, its effectiveness will be greatly reduced.

In certain embodiments, the phototherapy is combined with other types of treatments for an improved therapeutic effect. Treatment can comprise directing light through the scalp of the patient to a target area of the brain concurrently with applying an electromagnetic field to the brain. In such embodiments, the light has an efficacious power density at the target area and the electromagnetic field has an efficacious field strength. For example, the apparatus 50 can also include systems for electromagnetic treatment, e.g., as described in U.S. Pat. No. 6,042,531 issued to Holcomb, which is incorporated in its entirety by reference herein. In certain embodiments, the electromagnetic field comprises a magnetic field, while in other embodiments, the electromagnetic field comprises a radio-frequency (RF) field. As another example, treatment can comprise directing an efficacious power density of light through the scalp of the patient to a target area of the brain concurrently with applying an efficacious amount of ultrasonic energy to the brain. Such a system can include systems for ultrasonic treatment, e.g., as described in U.S. Pat. No. 5,054,470 issued to Fry et al., which is incorporated in its entirety by reference herein.

PHOTOTHERAPY EXAMPLES

Example 1

An in vitro experiment was done to demonstrate one effect of phototherapy on neurons, namely the effect on ATP production. Normal Human Neural Progenitor (NHNP) cells were obtained cryopreserved through Clonetics of Baltimore, Md., catalog # CC-2599. The NHNP cells were thawed and cultured on polyethyleneimine (PEI) with reagents provided with the cells, following the manufacturers' instructions. The cells were plated into 96 well plates (black plastic with clear bottoms, Becton Dickinson of Franklin Lakes, N.J.) as spheroids and allowed to differentiate into mature neurons over a period of two weeks.

A Photo Dosing Assembly (PDA) was used to provide precisely metered doses of laser light to the NHNP cells in the 96 well plates. The PDA included a Nikon Diaphot inverted microscope (Nikon of Melville, N.Y.) with a LUDL motorized x,y,z stage (Ludl Electronic Products of Hawthorne, N.Y.). An 808 nanometer laser was routed into the rear epi-fluorescent port on the microscope using a custom designed adapter and a fiber optic cable. Diffusing lenses were mounted in the path of the beam to create a "speckled" pattern, which was intended to mimic in vivo conditions after a laser beam passed through human skin. The beam diverged to a 25 millimeter diameter circle when it reached the bottom of the 96 well plates. This dimension was chosen so that a cluster of four adjacent wells could be lased at the same time. Cells were plated in a pattern such that a total of 12 clusters could be lased per 96 well plate. Stage positioning was controlled by a Silicon Graphics workstation and laser timing was performed by hand using a digital timer. The measured power density passing through the plate for the NHNP cells was 50 mW/cm$^2$.

Two independent assays were used to measure the effects of 808 nanometer laser light on the NHNP cells. The first was the CellTiter-Glo Luminescent Cell Viability Assay (Promega of Madison, Wis.). This assay generates a "glow-type" luminescent signal produced by a luciferase reaction with cellular ATP. The CellTiter-Glo reagent is added in an amount equal to the volume of media in the well and results in cell lysis followed by a sustained luminescent reaction that was measured using a Reporter luminometer (Turner Biosystems of Sunnyvale, Calif.). Amounts of ATP present in the NHNP cells were quantified in Relative Luminescent Units (RLUs) by the luminometer.

The second assay used was the alamarBlue assay (Biosource of Camarillo, Calif.). The internal environment of a proliferating cell is more reduced than that of a non-proliferating cell. Specifically, the ratios of NADPH/NADP, FADH/FAD, FMNH/FMN and NADH/NAD, increase during proliferation. Laser irradiation is also thought to have an effect on these ratios. Compounds such as alamarBlue are reduced by these metabolic intermediates and can be used to monitor cellular states. The oxidization of alamarBlue is accompanied by a measurable shift in color. In its unoxidized state, alamarBlue appears blue; when oxidized, the color changes to red. To quantify this shift, a 340PC microplate reading spectrophotometer (Molecular Devices of Sunnyvale, Calif.) was used to measure the absorbance of a well containing NHNP cells, media and alamarBlue diluted 10% v/v. The absorbance of each well was measured at 570 nanometers and 600 nanometers and the percent reduction of alamarBlue was calculated using an equation provided by the manufacturer.

The two metrics described above, (RLUs and % Reduction) were then used to compare NHNP culture wells that had been lased with 50 mW/cm$^2$ at a wavelength of 808 nanometers. For the CellTiter-Glo assay, 20 wells were lased for 1 second and compared to an unlased control group of 20 wells. The CellTiter-Glo reagent was added 10 minutes after lasing completed and the plate was read after the cells had lysed and the luciferase reaction had stabilized. The average RLUs measured for the control wells was 3808+/−3394 while the laser group showed a two-fold increase in ATP content to 7513+/−6109. The standard deviations were somewhat high due to the relatively small number of NHNP cells in the wells (approximately 100 per well from visual observation), but a student's unpaired t-test was performed on the data with a resulting p-value of 0.02 indicating that the two-fold change is statistically significant.

The alamarBlue assay was performed with a higher cell density and a lasing time of 5 seconds. The plating density (calculated to be between 7,500-26,000 cells per well based on the certificate of analysis provided by the manufacturer) was difficult to determine since some of the cells had remained in the spheroids and had not completely differentiated. Wells from the same plate can still be compared though, since plating conditions were identical. The alamarBlue was added immediately after lasing and the absorbance was measured 9.5 hours later. The average measured values for percent reduction were 22%+/−7.3% for the 8 lased wells and 12.4%+/−5.9% for the 3 unlased control wells (p-value=0.076). These alamarBlue results support the earlier findings in that they show a similar positive effect of the laser treatment on the cells.

Increases in cellular ATP concentration and a more reduced state within the cell are both related to cellular metabolism and are considered to be indications that the cell is viable and healthy. These results are novel and significant in that they show the positive effects of laser irradiation on cellular metabolism in in-vitro neuronal cell cultures.

Example 2

In a second example, transcranial laser therapy was investigated using a low-energy infrared laser to treat behavioral deficits in a rabbit small clot embolic stroke model (RSCEM). This example is described in more detail by P. A. Lapchak et al., "*Transcranial Infrared Laser Therapy Improves Clinical Rating Scores After Embolic Strokes in Rabbits,*" Stroke, Vol. 35, pp. 1985-1988 (2004), which is incorporated in its entirety by reference herein.

RSCEM was produced by injection of blood clots into the cerebral vasculature of anesthetized male New Zealand White rabbits, resulting in ischemia-induced behavioral deficits that can be measured quantitatively with a dichotomous rating scale. In the absence of treatment, small numbers of microclots caused no grossly apparent neurologic dysfunction while large numbers of microclots invariably caused encephalopathy or death. Behaviorally normal rabbits did not have any signs of impairment, whereas behaviorally abnormal rabbits had loss of balance, head leans, circling, seizure-type activity, or limb paralysis.

For laser treatment, a laser probe was placed in direct contact with the skin. The laser probe comprised a low-energy laser (wavelength of 808±5 nanometers) fitted with an OZ Optics Ltd. fiber-optic cable and a laser probe with a diameter of approximately 2 centimeters. Instrument design studies showed that these specifications would allow for laser penetration of the rabbit skull and brain to a depth of 2.5 to 3 centimeters, and that the laser beam would encompass the majority of the brain if placed on the skin surface posterior to bregma on the midline. Although the surface skin temperature below the probe was elevated by up to 3° C., the focal brain temperature directly under the laser probe was increased by 0.8° C. to 1.8° C. during the 10-minute laser treatment using the 25 mW/cm$^2$ energy setting. Focal brain temperature returned to normal within 60 minutes by laser treatment.

The quantitative relationship between clot dose and behavioral or neurological deficits was evaluated using logistic (S-shaped) curves fitted by computer to the quantal dose-response data. These parameters are measures of the amount of microclots (in mg) that produced neurologic dysfunction in 50% of a group of animals ($P_{50}$). A separate curve was generated for each treatment condition, with a statistically significant increase in the $P_{50}$ value compared with control being indicative of a behavioral improvement. The data were analyzed using the t test, which included the Bonferroni correction when appropriate.

To determine if laser treatment altered physiological variables, 14 rabbits were randomly divided into 2 groups, a control group and a laser-treated group (25 mW/cm$^2$ for 10 minutes). Blood glucose levels were measured for all embolized rabbits using a Bayer Elite XL 3901B Glucometer, and body temperature was measured using a Braun Thermoscan Type 6013 digital thermometer. Within 60 minutes of embolization, there was an increase in blood glucose levels in both the control group and the laser-treated group that was maintained for the 2 hours post-embolization observation time. Blood glucose levels returned to control levels by 24 hours, regardless of the extent of stroke-induced behavioral deficits. Laser treatment did not significantly affect glucose levels at any time. Neither embolization nor laser treatment significantly affected body temperature in either group of rabbits.

Figure 17A:
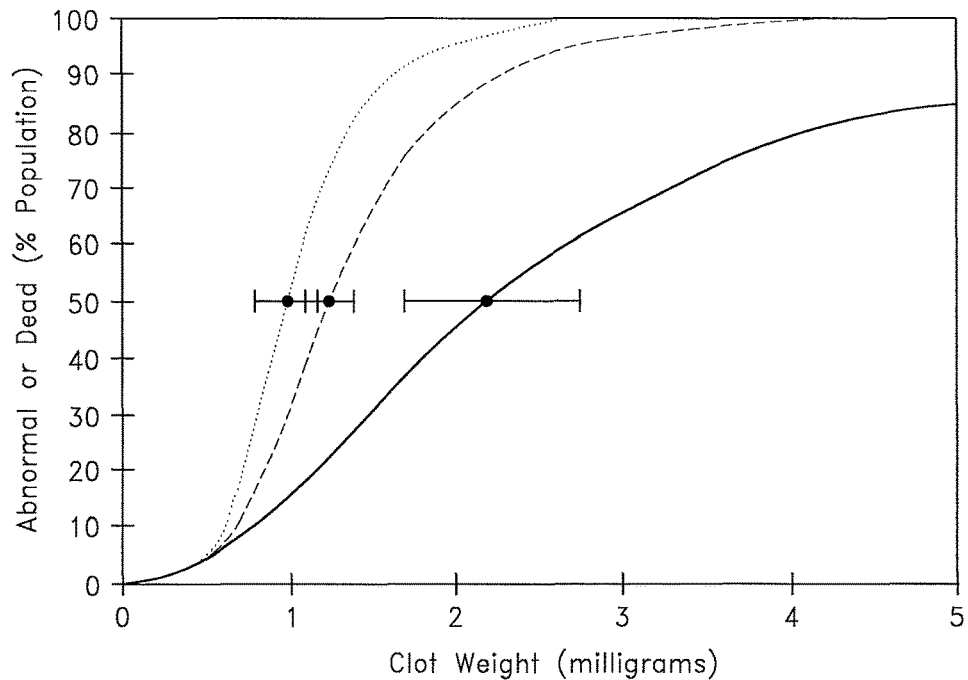
FIG. 17A is a graph of the effects of laser treatment of 7.5 $mW/cm^2$ for a treatment duration of 2 minutes on a population of rabbits having small clot embolic stroke.

FIG. 17A is a graph for the percentage of the population which was either abnormal or dead as a function of the clot weight in milligrams for laser treatment of 7.5 mW/cm$^2$ for a treatment duration of 2 minutes. As shown by FIG. 17A, the control curve (dotted line) has a $P_{50}$ value of 0.97±0.19 mg (n=23). Such laser treatment initiated 3 hours after the stroke significantly improved behavioral performance, with the $P_{50}$ value increased to 2.21±0.54 mg (n=28, *P=0/05) (solid line). The effect was durable and was measurable 3 weeks after embolization. However, the same setting did not improve behavior if there was a long delay (24 hours) after embolization (dashed line) ($P_{50}$=1.23±0.15 mg, n=32).

Figure 17B:
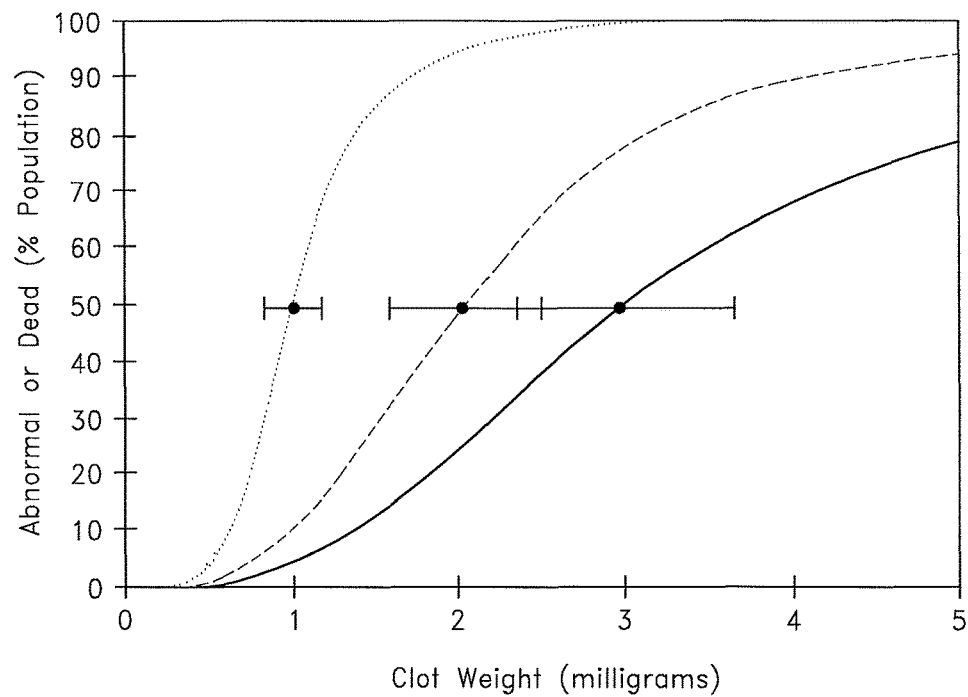
FIG. 17B is a graph of the effects of laser treatment of 25 $mW/cm^2$ for a treatment duration of 10 minutes on a population of rabbits having small clot embolic stroke.

FIG. 17B is a graph for the percentage of the population which was either abnormal or dead as a function of the clot weight in milligrams for laser treatment of 25 mW/cm$^2$ for a treatment duration of 10 minutes. As shown by FIG. 17B, the control curve (dotted line) has a $P_{50}$ value of 1.10±0.17 mg (n=27). Such laser treatment initiated 1 (dashed line) or 6 (solid line) hours after embolization also significantly increased behavioral performance, with the $P_{50}$ value increased to 2.02±0.46 mg (n=18, *P<0.05) and 2.98±0.65 mg (n=26, *P<0.05), respectively.

Figure 18:
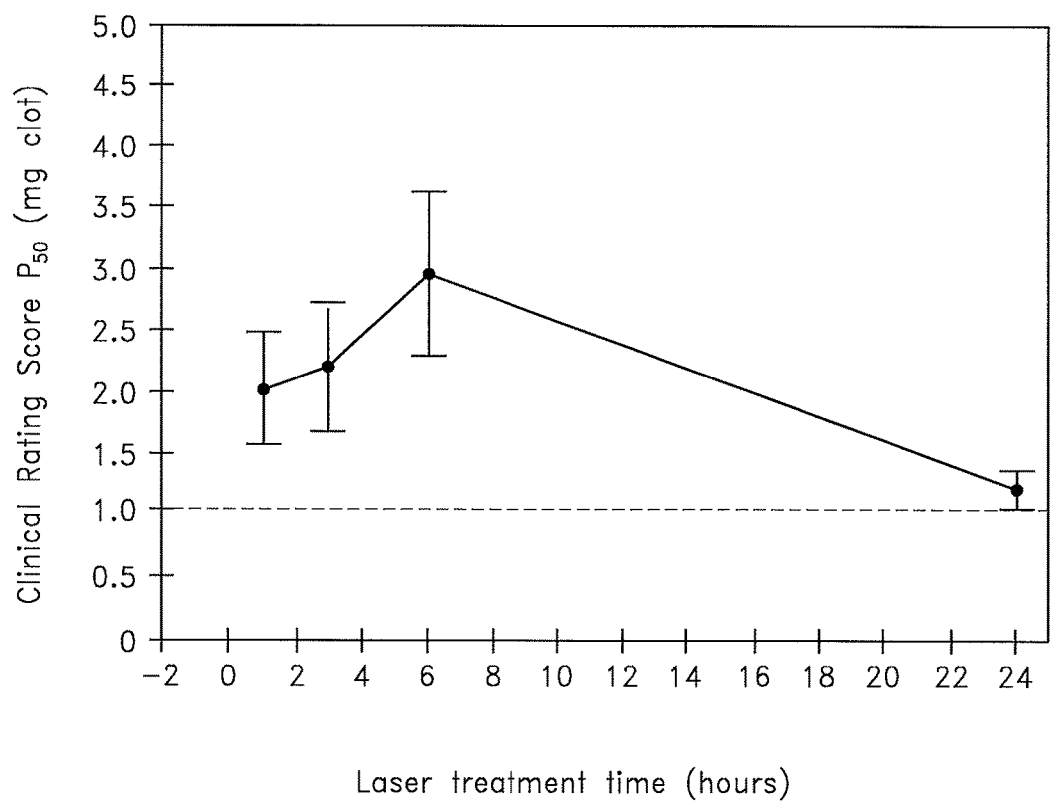
FIG. 18 is a graph showing the therapeutic window for laser-induced behavioral improvements after small-clot embolic strokes in rabbits.

FIG. 18 is a graph showing the therapeutic window for laser-induced behavioral improvements after small-clot embolic strokes in rabbits. Results are shown as clinical rating score $P_{50}$ (mg clot) given as mean±SEM for the number of rabbits per time point (number in brackets) for laser treatment initiated 1, 3, 6, or 24 hours after embolization as shown on the x-axis. The horizontal line represents the mean of the control $P_{50}$ values (*P<0.05).

The results in the RSCEM showed that laser treatment significantly improved behavioral rating scores after embolic strokes in rabbits without affecting body temperature and blood glucose levels. In addition, laser treatment was effective when initiated up to 6 hours after strokes, which is later than any other previously effective single therapy in the same preclinical stroke model. Moreover, the effect was durable and was measurable up to 21 days after embolization. The magnitudes of laser-induced improvement in rabbits are similar to previously tested thrombollytics (alteplase, tenecteplase, and microplasmin) and neuroprotective compounds (NXY-059), which are undergoing clinical development.

Neurologic Function Scales

Neurologic function scales can be used to quantify or otherwise characterize the efficacy of various embodiments described herein. Neurologic function scales generally use a number of levels or points, each point corresponding to an aspect of the patient's condition. The number of points for a patient can be used to quantify the patient's condition, and improvements in the patient's condition can be expressed by changes of the number of points. One example neurologic function scale is the National Institute of Health Stroke Scale (NIHSS) which can be used for short-term measurements of efficacy (e.g., at 24 hours). The NIHSS is a comprehensive and objective scale which utilizes a seven-minute physical exam, a 13 item scale, and 42 points. Zero points corresponds to a normal exam, 42 points (the maximum) corresponds to basically comatose, and over 15-20 points indicates that the effects of the stroke are particularly severe. The NIHSS has previously been used for tPA trials in the treatment of ischemic stroke, with a 4-point change over 24 hours and an overall score of 0 or 1 at three months indicative of a favorable outcome. Other neurologic function scales include, but are not limited to, modified Rankin Scale (mRS), Barthel Index (BI), Glasgow Outcome, Glasgow Coma Scale, Canadian Neurologic Scale, and stroke impact scales such as SIS-3 and SIS-16. In some scales, an improvement in the patient's condition is indicated by a reduction in the number of points. For example, the mRS has six points total, with zero corresponding to normal functioning, and six corresponding to death. In other scales, an improvement in the patient's condition is indicated by an increase in the number of points. For example, in the Glasgow Outcome which has five points, zero corresponds to death and five corresponds to full recovery. In certain embodiments, two or more of the neurologic function scales can be used in combination with one another, and can provide longer-term measurements of efficacy (e.g., at three months).

For stroke, the U.S. Food and Drug Administration (FDA) and the neurologic community have expressed interest in clinical patient outcomes at 90 days post stroke. Two of the most common and accepted instruments for measuring efficacy are the NIHSS and mRS. The FDA is flexible in the way that neurologic function scales can be used. For example, it is acceptable to used the mRS (i) in dichotomized fashion with success at score of 0-1 or (ii) it can be analyzed looking at shifts in the scale showing improvement of patients along the five-point scale.

In certain embodiments described herein, a patient exhibiting symptoms of an ischemic stroke is treated by irradiating a plurality of treatment sites on the patient's scalp. The irradiation is performed utilizing irradiation parameters (e.g., wavelength, power density, time period of irradiation, etc.) which, when applied to members of a treated group of patients, produce at least a 2% average difference between the treated group and a placebo group on at least one neurologic function scale analyzed in dichotomized or any other fashion and selected from the group consisting of: NIHSS, mRS, BI, Glasgow Outcome, Glasgow Coma Scale, Canadian Neurologic Scale, SIS-3, and SIS-16. Certain other embodiments produce at least a 4% average difference, at least a 6% average difference, or at least a 10% average difference between treated and placebo groups on at least one of the neurologic function scales analyzed in dichotomized or any other fashion and selected from the group consisting of: NIHSS, mRS, BI, Glasgow Outcome, Glasgow Coma Scale, Canadian Neurologic Scale, SIS-3, and SIS-16. In certain embodiments, the irradiation of the patient's scalp produces a change in the patient's condition. In certain such embodiments, the change in the patient's condition corresponds to a change in the number of points indicative of the patient's condition. In certain such embodiments, the irradiation produces a change of one point, a change of two points, a change of three points, or a change of more than three points on a neurologic function scale.

Possible Action Mechanisms

The following section discusses theories and potential action mechanisms, as they presently appear to the inventors, for certain embodiments of phototherapy described herein. The scope of the claims of the present application is not to be construed to depend on the accuracy, relevance, or specifics of any of these theories or potential action mechanisms. Thus the claims of the present application are to be construed without being bound by theory or by a specific mechanism.

It is well known that light can produce profound biological effects such as vision, regulation of circadian hormones, melanin production, and Vitamin D synthesis. It has also been shown that specific wavelengths of light targeted at the cytochrome C receptor in the mitochondria can dramatically preserve function, as well as, reduce the size of myocardial infarcts and stroke. It has also been shown that these effects can be reproduced across multiple species. This is not surprising since the mitochondrial target receptor (i.e., copper ions in cytochrome C) is conserved between species. These effects may be due to production of new cells (neurogenesis), preservation of existing tissue (neuroprotection) or a combination of both.

The clinical and cellular responses to light for in vivo treatment efficacy of ischemic conditions of acute myocardial infarction and stroke has been demonstrated in multiple validated animal models. As described more fully below, these effects are wavelength-specific. Without being bound by theory or by a specific mechanism, the wavelength specificity may be dependent upon a known mitochondrial receptor (cyctochrome C oxidase). Targeting of this receptor may result in formation of adenosine triphosphate (ATP), enhanced mitochondrial survival, and maintenance of cytochrome C oxidase activity.

In stroke, the occlusion of a major artery results in a core area of severe ischemia (e.g., with blood flow reduced to less than 20% of pre-occlusion levels). The core area has a rapid loss of ATP and energy production, and the neurons are depolarized. This core of the infarct is surrounded by an ischemic penumbra which can be up to twice as large as the core of the infarct. Cells within the penumbra show less severe decreases in loss of blood flow (e.g., 20 to 40% of normal). Neurons in the penumbra tend to be hyperpolarized and electrically silent. In the penumbra, the cells undergo progression of cell death lasting from hours to days after the infarct. Also, inflammation after infarct can play a role in determining the final infarct size and anti-inflammatory modulators can reduce infarct size. The infarct is dynamic, with different parts of the infarct being affected to different degrees over a period of hours to days. Photon therapy has been implicated in a number of physiological processes that could favor cell survival in the penumbral region of a stroke.

In Vitro

The action of light on a cell is mediated by one or more specific photo acceptors. A photo acceptor molecule first absorbs the light. After this absorptive event and promotion of an electron to an excited state, one or more primary molecular processes from these high energy states can lead to a measurable biological effect at the cellular level. An action spectra represents the biological activity as a function of wavelength, frequency or photon energy. Karu was the first researcher to propose that the action spectra should resemble the absorption spectra of the photoacceptor molecule. Since an absorptive event occurs for a transfer of energy to take place, the stimulatory wavelengths of the action spectra falls within the absorptive spectra of the photo acceptor.

Karu was also the first to propose a specific mechanism for photon therapy at the cellular level (see, e.g., T. Karu, "*Photobiological Fundamentals of Low Power Laser Therapy,*" *IEEE Journal of Quantum Electronics,* 1987, Vol. 23, page 1703; T. Karu, "*Mechanisms of interaction of monochromatic visible light with cells,*" *Proc. SPIE,* 1995, Vol. 2630, pages 2-9). Karu's hypothesis was based on the absorption of monochromatic visible and near infrared radiation by components of the cellular respiratory chain. Absorption and promotion of electronically excited states cause changes in redox properties of these molecules and acceleration of electron transfer (primary reactions). Primary reactions in mitochondria of eukaryotic cells are followed by a cascade of secondary reactions occurring in the cytoplasm, cell membrane, and nucleus. Karu defined the action spectra for mammalian cells of several secondary reactions (DNA, RNA synthesis, cellular adhesion). The action spectra for all of these secondary markers were very similar, suggesting a common photo acceptor. Karu then compared these action spectra with absorption spectra of the copper centers of cytochrome C oxidase in both reduced and oxidized states. Cytochrome C oxidase contains four redox active metal centers and has a strong absorbance in the near infrared spectral range. The spectral absorbance of cytochrome C oxidase and the action spectra were very similar. Based on this, Karu suggested that the primary photoacceptors are mixed valence copper centers within cytochrome C oxidase.

Cytochrome C oxidase is the terminal enzyme of the mitochondrial electron transport chain of all eukaryotes and is required for the proper function of almost all cells, especially those of highly metabolically active organs, such as the brain and heart. Cytochrome C has also been suggested to be the critical chromophore responsible for stimulatory effects of irradiation with infrared light to reverse the reduction in cytochrome C oxidase activity produced by the blockade of voltage dependent sodium channels with tetrodotoxin and up regulated cytochrome C activity in primary neuronal cells. It has been demonstrated by researchers (see, e.g., M. T. Wong-Riley et al., *NeuroReport*, 2001, Vol. 12, pages 3033-3037; J. T. Eells et al., *Proceedings National Academy of Science*, 2003, Vol. 100, pages 3439-3444) that in vivo, rat retinal neurons are protected from damage induced by methanol intoxication. Methanol's toxic metabolite is formic acid which inhibits cytochrome C.

Several investigators have demonstrated the increased synthesis of ATP from infrared irradiation both in vitro and in vivo. Karu has shown that irradiation of cells in vitro at wavelengths of 632 nanometers, 670 nanometers, and 820 nanometers can increase mitochondrial activity.

In Vivo

There are numerous studies, both published and unpublished, demonstrating the effectiveness of photon therapy in animal models for acute myocardial infarction (AMI) and ischemic stroke. These studies suggest that photon therapy induces a cascade of signaling events initiated by the initial absorption of light by cytochrome C. These signaling events apparently up-and-down regulate genes, transcription factors, as well as increase mitochondrial function.

Without being bound by theory or a specific mechanism, in stroke, reduction of infarct volume may occur in one of two ways or a combination of both: (i) preservation of existing tissue (neuroprotection), and (ii) generation of new tissue (neurogenesis). A number in vitro and in vivo studies appear to support both of these potential mechanisms. The potential effects of NIR light on neurogenesis are straightforward; it either increases the number of new cells, or it prevents the loss of new cells that are generated as a result of the ischemic insult. Neuroprotection can result from at least three mechanisms: (i) direct stimulation of tissue survival; (ii) indirect stimulation of tissue survival (e.g., increased growth factor activity); and (iii) decrease in toxic factors.

Figure 36:
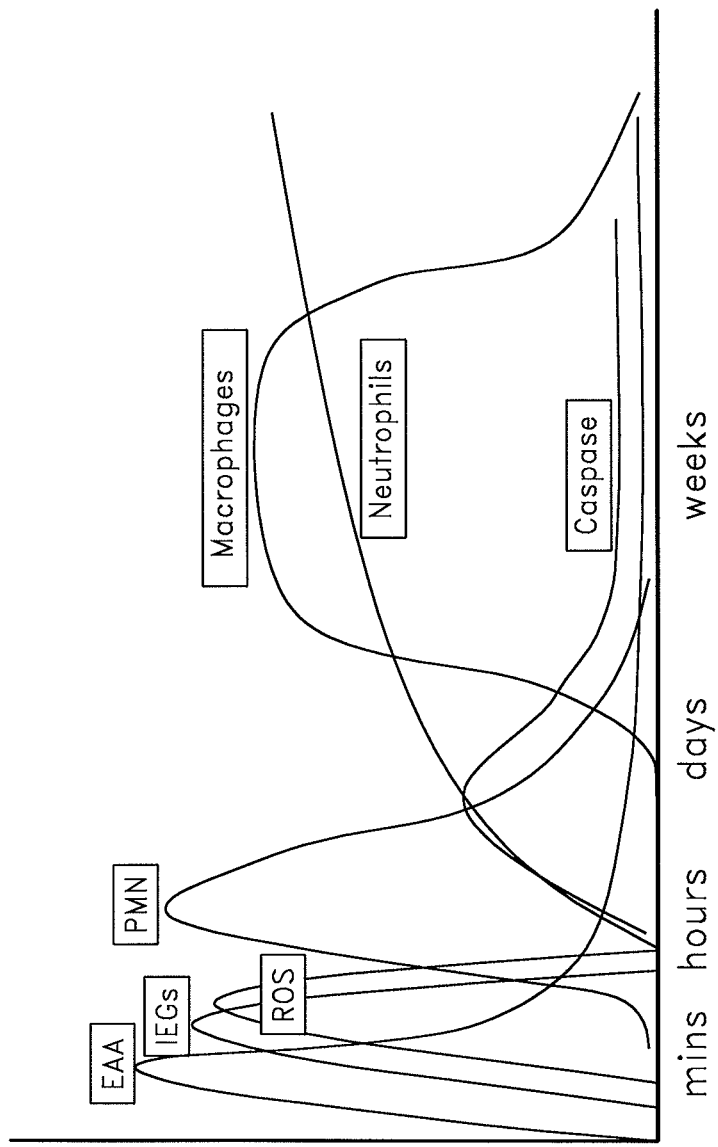
FIG. 36 is a graph which shows mediators responsible for ischemic stroke tissue damage and the time points at which they occur.

FIG. 36 is a graph which shows mediators responsible for ischemic stroke tissue damage and the time points at which they occur. FIG. 36 illustrates several potential places where photon therapy could potentially intervene to reduce infarct severity. Early after ischemic stroke, excitatory amino acids (EAAs) induce $Ca^{2+}$ influx via NMDA receptor activation leading to neuronal and glial cell injury. A number of immediately early genes (IEGs) express such as c-fos, c-jun, within 30 minutes. Reactive oxygen species (ROSs) create lipid peroxidation and activated phagocytes which create further injury. ROSs damage most cellular components. Cytokines are then expressed causing migration of polymorphonuclear neutrophils (PMNs) into the ischemic brain. Macrophages and neutrophils follow into the brain parenchyma. Apoptosis occurs via caspase activation which further increases stroke damage.

Preservation of existing tissue (neuroprotection) can result from direct stimulation of the tissue (e.g., by ATP synthesis or by prevention of cytochrome C release from mitochondria). Ischemia results in depletion of ATP in the ischemic zone due to lack of oxygen and glucose. The resultant lack of ATP, depending on severity, results in decreased cellular function. In extreme cases, energy depletion leads to cell depolarization, calcium influx, and activation of necrotic and apoptotic processes. Near-infrared radiation (NIR) stimulates the production of ATP in a variety of cell types in culture, and in cardiac tissue. A single irradiation of infarcted cardiac tissue results in a statistically significant 3-fold increase in tissue ATP levels four hours after treatment. The effect of NIR is prolonged long after irradiation is ceased. The prolonged effect could also be due, in part, to preservation of mitochondrial function. NIR irradiated, infarcted cardiac tissue has exhibited over a 50% reduction in damaged mitochondria. After ischemia, the myocardial tissue that is not immediately lost is in a "stunned" state, and can remain stunned for a period of days. In particular, it is the mitochondria in the tissue that are stunned. Stunned mitochondria are still intact, but with characteristic morphological changes that are indicative of mitochondria that are not metabolically active. As such, even with restored blood flow, the mitochondria are unable to convert oxygen and glucose to useable energy (ATP).

Neuroprotection can also result from direct stimulation of the tissue by preventing cytochrome C release from mitochondria. The release of cytochrome C from the mitochondria into the cytoplasm is a potent apoptotic signal. Cytochrome C release results in the activation of caspase-3 and activation of apoptotic pathways. The apoptotic cells appear as soon as a few hours after stroke, but the cell numbers peak at 24 to 48 hours after reperfusion. In rat models of stroke, cytoplasmic cytochrome C can be detected out to at least 24 hours after the occlusion. In vitro 810-nanometer light can prevent the TTX-induced decrease in cytochrome oxidase activity. Photon therapy may also be able to maintain cytochrome oxidase activity in vivo by preventing release of cytochrome C into the cytoplasm, resulting in the prevention of apoptosis. The release of cytochrome C is regulated by the Bcl/Bax system. Bax promotes release and Bcl decreases release. In myofiber cultures in vitro, NIR light promotes Bcl-2 expression and inhibits Bax expression, which fits with the prevention of cytochrome C release data.

Neuroprotection can also result from indirect stimulation (e.g., by angiogenesis or by up-regulation of cell survival genes and/or growth factors). Regarding angiogenesis and stroke, recent research indicates that the reduction in cerebral blood flow (CBF) can lead to compensatory neovascularization in the affected regions. The low CBF results in the up regulation of hypoxia inducible factor-1 (HIF-1), vascular endothelial growth factor (VEGF), and VEGF receptors. In the rat pMCAo model, infusion of VEGF results in a reduction of infarct size. In AMI models, VEGF is increased with photon therapy.

Regarding up-regulation of cell survival genes and/or growth factors, it has been shown that photon therapy may up-, and down-regulate certain beneficial genes. It is possible that these gene products can prevent or ameliorate apoptosis, which is known to occur throughout the stoke penumbra and in stunned myocardium of AMI. In AMI models, expression of the cardioprotective molecules HSP70 and VEGF are increased. In stroke, equivalent neuroprotective molecules could be up-regulated, preserving tissue and resulting in reduction of infarct volumes. A variety of factors have been implicated in neuroprotection in addition to VEGF, including BDNF, GDNF, EGF, FGF, NT-3, etc. There are a number of factors that could be up-regulated to promote neuronal survival, at least one of which is increased due to NIR light treatment.

Neuroprotection can also result from decreases in toxic factors (e.g., antioxidant protection or by reduction of deleterious factors to tissue function and survival). Regarding antioxidant protection, NIR light may reduce damage induced by free radicals. By-products of free radical damage are found in damaged brain tissue following stroke. This damage is thought to be mediated by neutrophils during reperfusion injury. The nominal spin-trap agent NXY-059 (a free radical scavenger) reduces infarct size if given within 2.25 hours of a stroke (in rat, although it is more effective if given sooner). NIR light can induce the expression of catalase in AMI models. Catalase is a powerful anti-oxidant which can prevent free radical damage and, if produced in the area of the stroke, it may prevent loss via the same mechanism as NXY-059. Axon survival is known to be improved by catalase.

In addition, a number of cytokines and other factors are produced during reperfusion that are deleterious to tissue function and survival. These factors promote activity of existing phagocytic and lymphocytic cells as well as attract additional cells to the area of damage. NIR light can decrease the levels of cytokines in models of neuronal damage. In particular, IL-6 and MCP-1 (pro-inflammatory cytokines) are induced in models of spinal cord damage. NIR light significantly reduces IL-6 and MCP-1 and promotes regrowth of the spinal cords neurons. IL-6 is thought to play a significant role in spinal cord damage in man also.

Regarding neurogenesis, in the last several years, it has been become well-established that the brain has the ability to generate new nerve cells in certain instances. Neural stem cells have been shown to exist in the periventricular areas and in the hippocampus. Naturally-occurring growth factors in the adult human brain can spur the production of new nerve cells from these stem cells. After a stroke, neurogenesis commences in the hippocampus with some cells actually migrating to the damaged area and becoming adult neurons.

NIR light may be effective by either increasing the number of new cells that are formed, or by preventing the loss of the newly formed cells. The latter may be more significant and the majority of newly-formed cells die within 2 to 5 weeks after the stroke (rat model). In an unpublished study by Oron, NIR light has been shown to increase the survival of cardiomyocytes implanted into infarcted heart. Other studies have shown the human neural progenitor cells can be induced to differentiate with stimulation of 810-nanometer irradiation without the presence of specific growth factors that are normally required for differentiation. These data suggest that neurogenesis could occur if the infrared irradiation were to act as a stimulating signal much like a growth factor. Early data from a porcine study of AMI has shown that the 810-nanometer-irradiated pig myocardium showed evidence of cardiogenesis. This result was demonstrated by the presence of significant desmin staining in the laser treated group over control, and by ultrastructural analysis which demonstrated the presence of what appears to be developing cardiomyocytes.

Wavelength Selection

The following section discusses theories and potential action mechanisms, as they presently appear to the inventors, regarding the selection of wavelengths for certain embodiments of phototherapy described herein. The scope of the claims of the present application is not to be construed to depend on the accuracy, relevance, or specifics of any of these theories or potential action mechanisms. Thus the claims of the present application are to be construed without being bound by theory or by a specific mechanism.

In certain embodiments, non-invasive delivery and heating by the electromagnetic radiation place practical limits on the ranges of electromagnetic radiation wavelengths to be used in the treatment of the patient's brain. In certain embodiments, the wavelength of electromagnetic radiation used in the treatment of the patient's brain is selected in view of one or more of the following considerations: (1) the ability to stimulate mitochondrial function in vitro; (2) the ability to penetrate tissue; (3) the absorption in the target tissue; (4) the efficacy in other ischemia models in vivo; and (5) the availability of laser sources with the desired power at the desired wavelength or wavelengths. The combination of these effects offers few wavelengths to be used as a therapeutic agent in vivo. These factors can be combined in certain embodiments to create an efficiency factor for each wavelength. Wavelengths around 800 nanometers are particularly efficient. In addition, 808-nanometer light has previously been found to stimulate mitochondrial function and to work in the myocardial infarction models in rat and dog. The following discussion deals with these considerations in more detail.

Photostimulation Effects on Mitochondria

The mitochondria convert oxygen and a carbon source to water and carbon dioxide, producing energy (as ATP) and reducing equivalents (redox state) in the process. The process details of the electron transport chain in mitochondria are schematically diagrammed in FIG. 37. The chemical energy released from glucose and oxygen is converted to a proton gradient across the inner membrane of the mitochondria. This gradient is, in turn, used by the ATPase complex to make ATP. In addition, the flow of electrons down the electron transfer chain produces NADPH and NADH (and other factors such as FAD). These cofactors are important for maintaining the redox potential inside the cell within the optimal range. This process has been called the chemiosmotic theory of mitochondrial function (Dr. Peter Mitchell was awarded a Nobel Prize in chemistry for elucidating these key processes).

Figure 37:
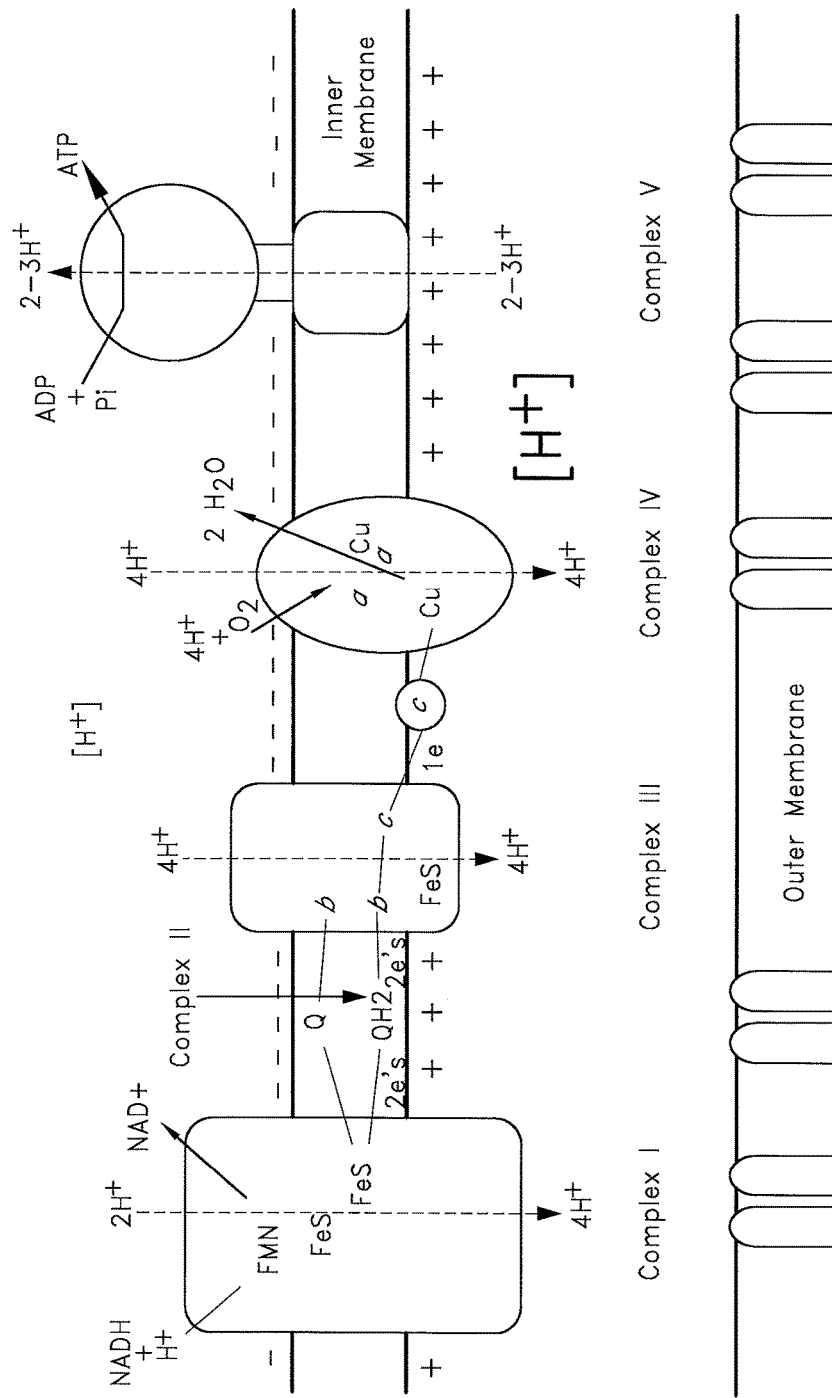
FIG. 37 is a schematic diagram of the electron transport chain in mitochondria.

There are five large components of the electron transfer chain, Complexes I-IV and the ATPase (also called Complex V), with each complex containing a number of individual proteins (see FIG. 37). One of the critical complexes, Complex IV (cytochrome oxidase), is the component responsible for the metabolism of oxygen. The cytochrome C oxidase protein is a key player in the electron transfer in Complex IV through its copper centers. These copper centers have been proposed as important chromophores (photoacceptors) for the absorption of light energy in the near infra-red region.

As an aside, cytochrome C oxidase has enjoyed a renaissance in the last few years as an important factor in the regulation of apoptosis (programmed cell death). Release of cytochome C oxidase from the mitochondria into the cytosol is a pro-apoptotic signal.

Figure 38:
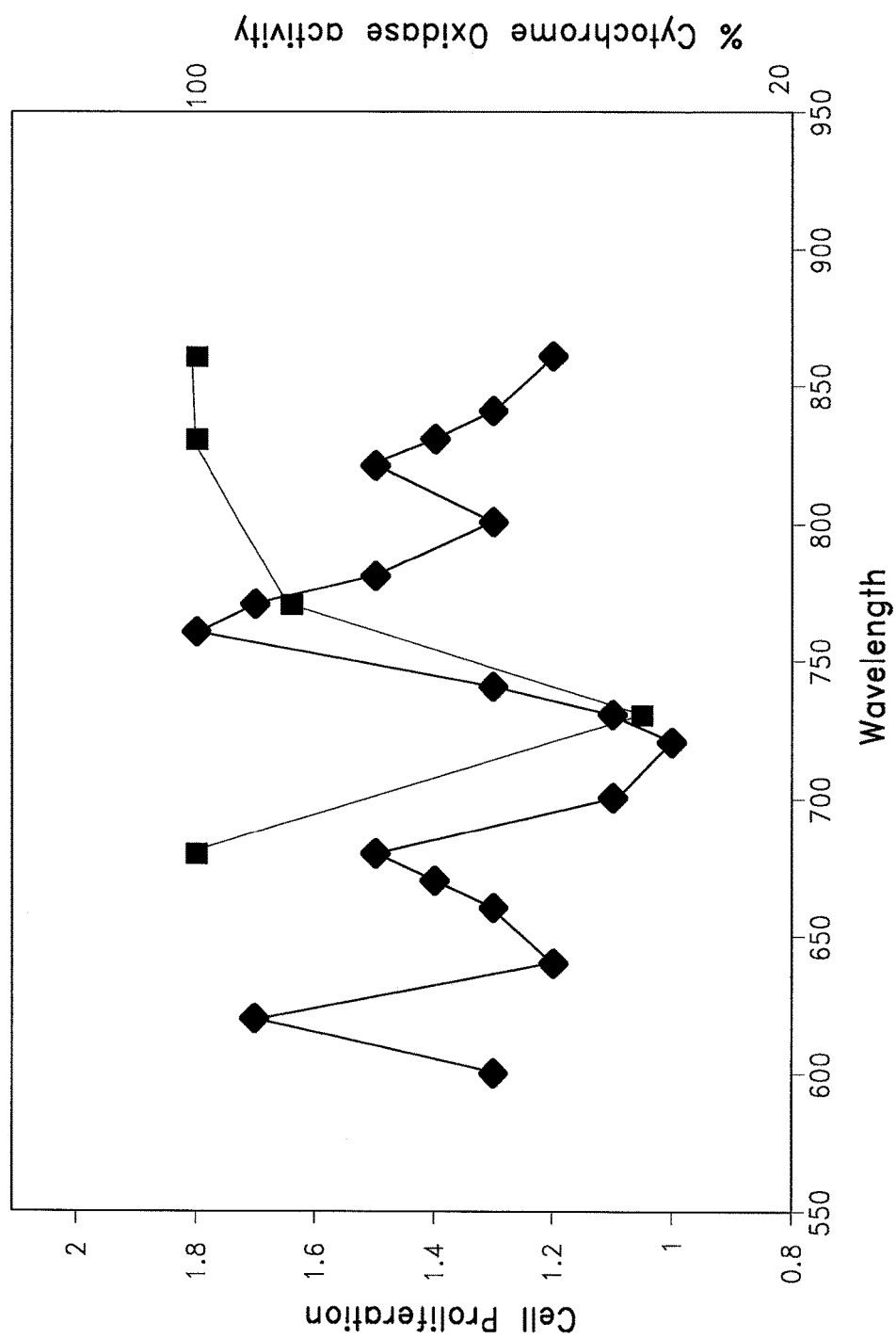
FIG. 38 is a graph of cell proliferation and cytochrome oxidase activity percentage as functions of the wavelength of light used to stimulate mammalian cells.

It has been postulated by others that light can directly activate Complex IV and indirectly driving the production of ATP via ATPase (and reducing equivalents). For example, Karu studied the activation spectra of these processes and found that wavelengths that maximally stimulated energy-dependant cellular functions corresponded to the absorption bands of the copper centers in cytochrome C oxidase. FIG. 38 is a graph of cell proliferation and cytochrome oxidase activity percentage as functions of the wavelength of light used to stimulate mammalian cells. Based on these results, wavelengths of 620, 680, 760, and 820 nanometers (±10 nanometers) promote cellular activities. The 620 and 820 nanometer wavelengths are close to the strongest copper absorption maxima of 635 and 810 nanometers.

Additional data from other groups suggest that cytochrome C oxidase is an important target. Light (670 nanometers) can rescue primary neurons from the toxic effects of the sodium channel blocker tetrodotoxin (TTX). TTX reduces cytochome oxidase activity in treated neurons, and this reduction is reversed by light treatment (an increase in cytochrome oxidase activity). In an in vivo model, 670 nanometer light is used to rescue retinal function in a methanol-mediated model of retinal damage. Methanol is metabolized to formate, a selective mitochondrial toxin targeted at cytochome C oxidase. Irradiation with light (670 nanometers) rescued the retina from damage induced by methanol.

Tissue Penetration and Absorption

In vitro and near in vitro like conditions (retinal studies) have previously demonstrated that light can induce beneficial effects in animals. Yet these effects required little if any ability to penetrate non-involved tissues. For treatments of stroke and myocardial infarction by irradiation through intervening tissue, only wavelengths that can penetrate to the affected tissue have the potential to treat the disease.

Light can be absorbed by a variety of chromophores. Some chromophores, such as cytochrome C oxidase can convert the light energy into chemical energy for the cell. Other chromophores can be simple and the light energy is converted to heat, for example water. The absorption of light energy is wavelength dependent and chromophore dependant.

Some chromophores, such as water or hemoglobin, are ubiquitous and absorb light to such a degree that little or no penetration of light energy into a tissue occurs. For example, water absorbs light above approximately 1300 nanometers. Thus energy in this range has little ability to penetrate tissue due to the water content. However, water is transparent or nearly transparent in wavelengths between 300 and 1300 nanometers. Another example is hemoglobin, which absorbs heavily in the region between 300 and 670 nanometers, but is reasonably transparent above 670 nanometers.

Based on these broad assumptions, one can define an "IR window" into the body. Within the window, there are certain wavelengths that are more or less likely to penetrate. This discussion does not include wavelength dependent scattering effects of intervening tissues.

Figure 39:
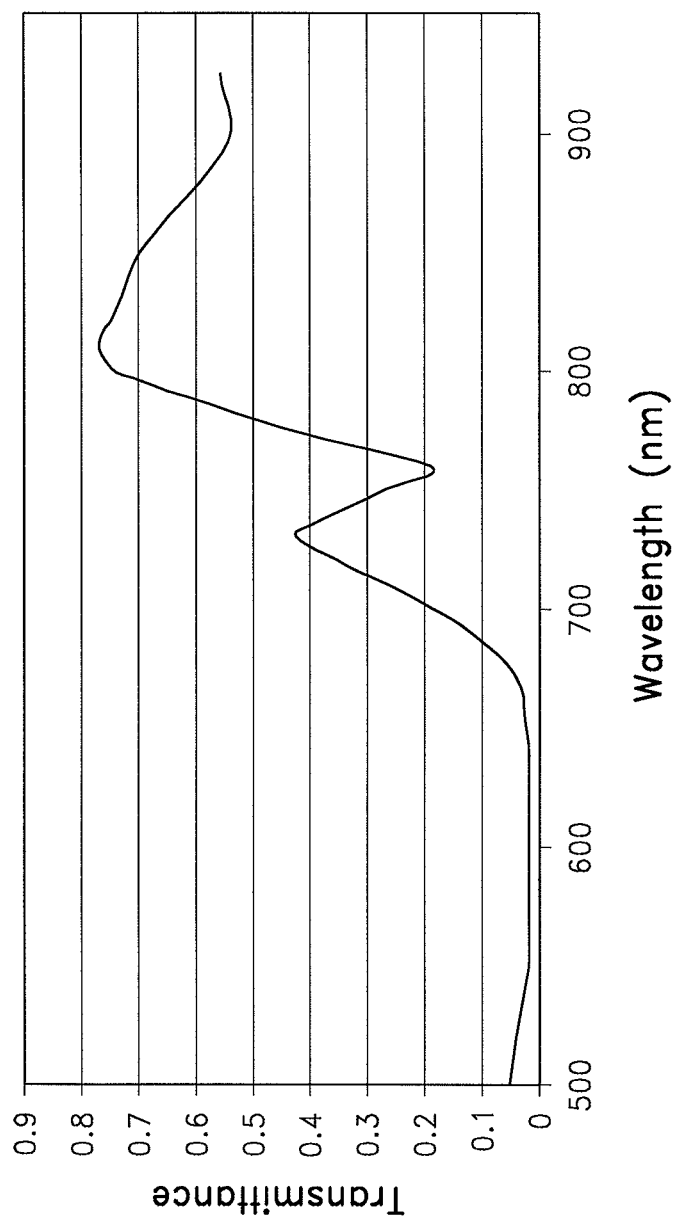
FIG. 39 is a graph of the transmittance of light through blood (in arbitrary units) as a function of wavelength.

The absorption/transmittance of various tissues have been directly measured to determine the utility of various wavelengths. FIG. 39 is a graph of the transmittance of light through blood (in arbitrary units) as a function of wavelength. Blood absorbs less in the region above 700 nanometers, and is particularly transparent at wavelengths above 780 nanometers. Wavelengths below 700 nanometers are heavily absorbed, and are not likely to be useful therapeutically (except for topical indications).

Figure 40:
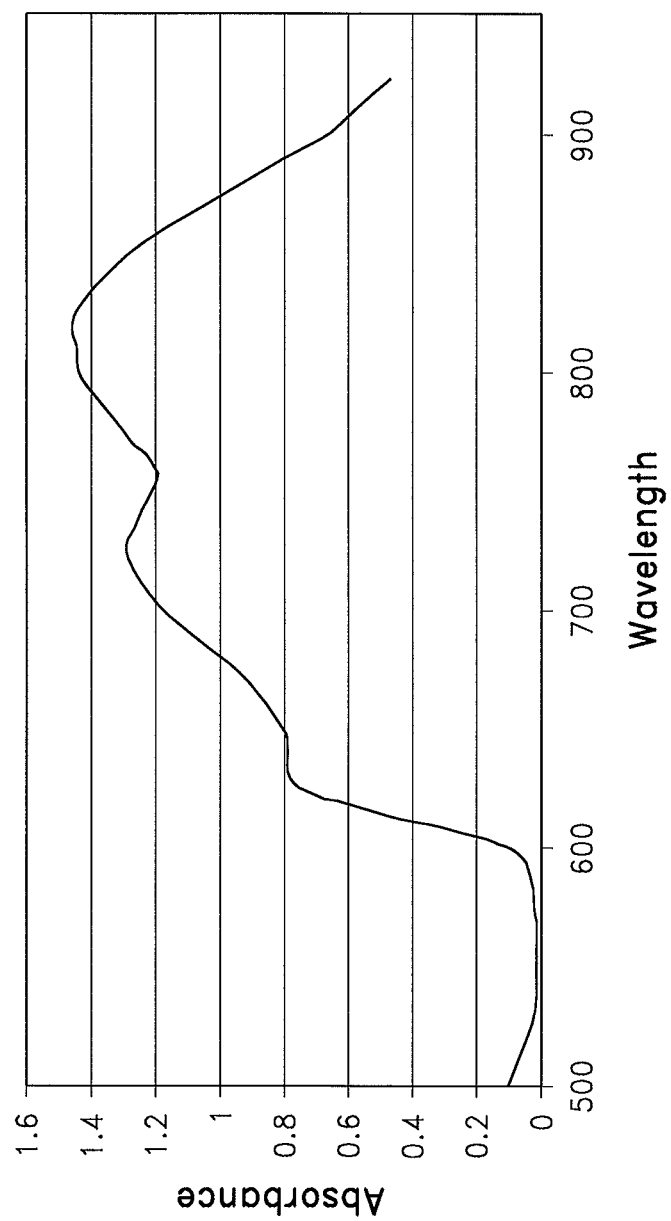
FIG. 40 is a graph of the absorption of light by brain tissue.

FIG. 40 is a graph of the absorption of light by brain tissue. Absorption in the brain is strong for wavelengths between 620 and 900 nanometers. This range is also where the copper centers in mitochondria absorb. The brain is particularly rich in mitochondria as it is a very active tissue metabolically (the brain accounts for 20% of blood flow and oxygen consumption). As such, the absorption of light in the 620 to 900 nanometer range is expected if a photostimulative effect is to take place.

Figure 41:
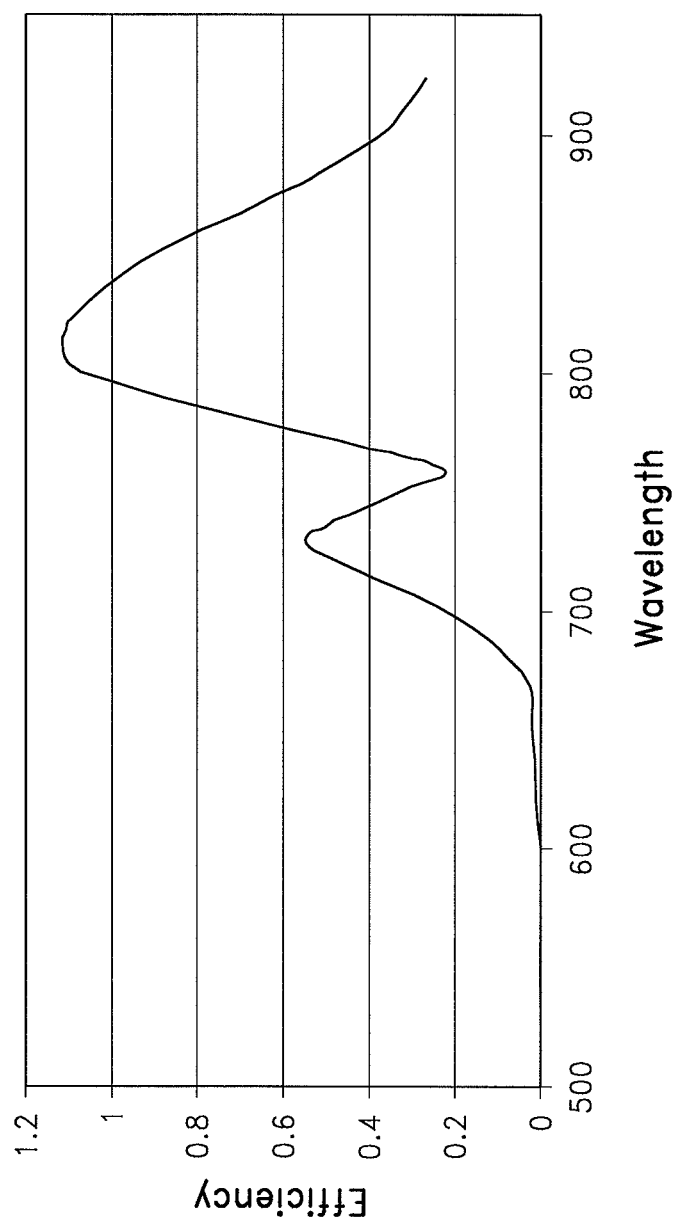
FIG. 41 is a graph of the efficiency of energy delivery as a function of wavelength.

By combining FIGS. 39 and 40, the efficiency of energy delivery as a function of wavelength can be calculated, as shown in FIG. 41. Wavelengths between 780 and 880 nanometers are preferable (efficiency of 0.6 or greater) for targeting the brain. The peak efficiency is about 800 to 830 nanometers (efficiency of 1.0 or greater). These wavelengths are not absorbed by water or hemoglobin, and are likely to penetrate to the brain. Once these wavelengths reach the brain, they will be absorbed by the brain and converted to useful energy.

Figure 42:
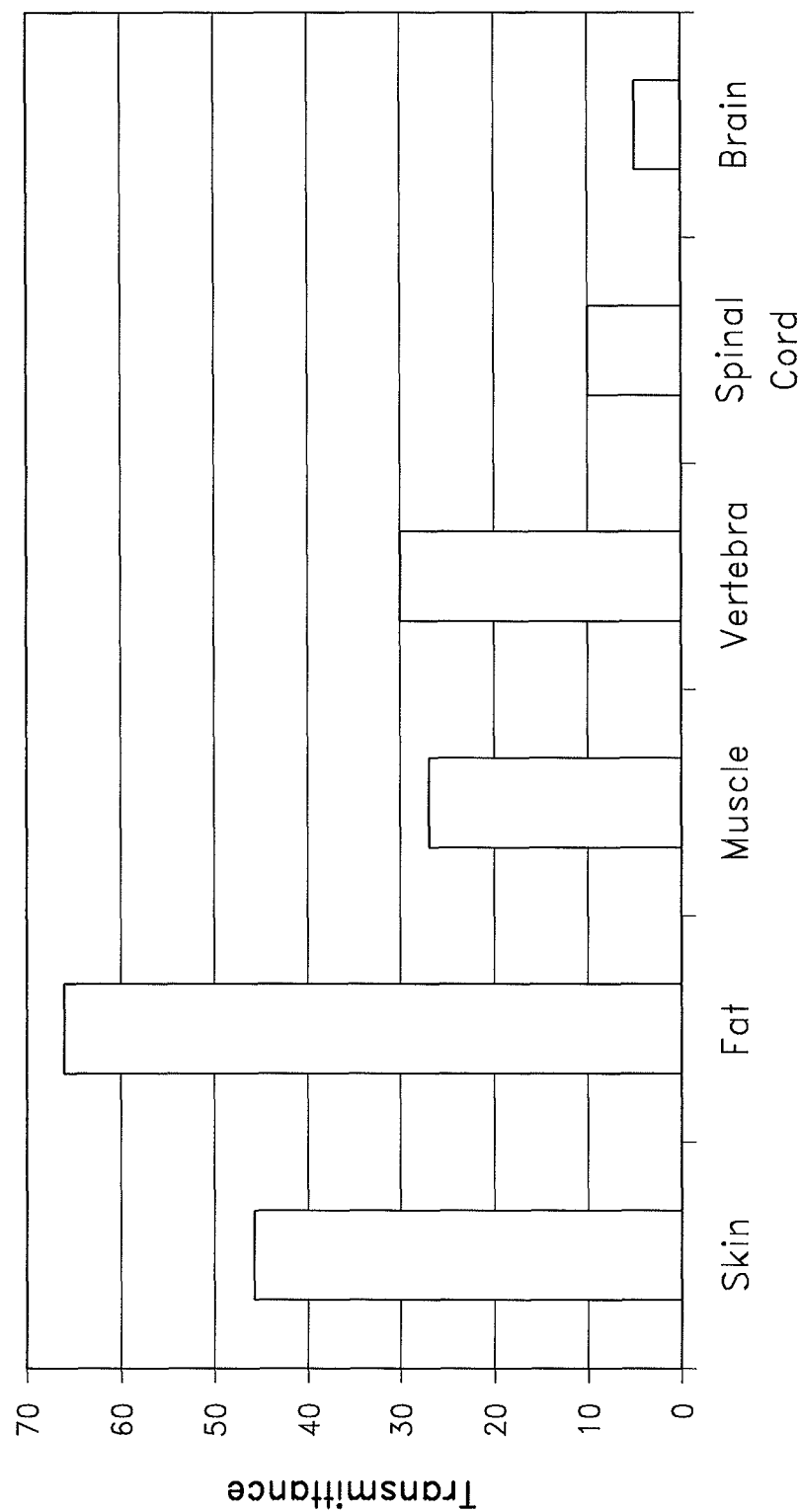
FIG. 42 is a bar graph of the absorption of 808 nanometer light through various rat tissues.

These effects have been directly demonstrated in rat tissues. The absorption of 808 nanometer light was measured through various rat tissues, as shown in FIG. 42. Soft tissues such as skin and fat absorb little light. Muscle, richer in mitochondria, absorbs more light. Even bone is fairly transparent. However, as noted above, brain tissue, as well as spinal cord tissue, absorb 808 nanometer light well.

Efficacy in Other Tissues

Two wavelengths have demonstrated efficacy in animal models of ischemia/mitochondrial damage, namely, 670 nanometers and 808 nanometers. Light having a wavelength of 670 nanometers has shown efficacy in retinal damage. Light having a wavelength of 808 nanometers has demonstrated efficacy in animal models of myocardial infarction (as well as soft tissue injury).

The effects of near infrared light on soft tissue injury have been established in FDA approved trials for carpal tunnel syndrome (830 nanometers) and knee tendonitis (830 nanometers). In both cases, 830 nanometer light was superior to placebo for resolution of symptoms.

Light having a wavelength of 808 nanometers was also used to reduce infarct volume and mortality in myocardial infarction (MI) models in rat, dog, and pig. The MI models are particularly relevant to wavelength selection as similar processes—apoptosis, calcium flux, mitochondrial damage—have been implicated in stroke and MI.

Certain wavelengths of light are associated with activation of biological processes, and others are not. In particular, light mediated mitochondrial activation has been used as a marker of biostimulation. Given the lack of in vivo markers, the use of in vitro markers of light activation was used to help narrow down the large number of potential wavelengths. Wavelengths that activate mitochondria were determined, and these wavelengths were used in vivo models.

Penetration to the target tissue is also of importance. If a biological effect is to be stimulated, then the stimulus must reach the target tissue and cell. In this regard, wavelengths between 800 and 900 nanometers are useful, as they can penetrate into the body. In particular, wavelengths of 800 to 830 nanometers are efficient at penetrating to the brain and then being absorbed by the brain.

The use of 808 nanometer light has a solid basis for the treatment of stroke. This wavelength of light can penetrate to the target tissue (brain), is absorbed by the target tissue, stimulates mitochondrial function, and works in a related animal model of ischemia (MI). This supposition is supported by the striking finding that 808 nanometer light can reduce the neurological deficits and infarct volume associated with stroke (in rats).

Other wavelengths have some of these properties. For example, 670 nanometer light can promote mitochondrial function and preserve retinal neurons. However, this wavelength does not penetrate tissue well as it is highly absorbed by hemoglobin. It is therefore not useful in treating stroke.

In certain embodiments, wavelengths from 630 to 904 nanometers may be used. This range includes the wavelengths that activate mitochondria in vitro, and that have effects in animal models. These wavelengths also include the predominant bands that can penetrate into the body.

Transmission in Human Brain

Power density (PD) measurements have been made to determine the transmission of laser light having a wavelength of approximately 808 nanometers through successive layers of human brain tissue. Laser light having a wavelength of (808±5) nanometers with a maximum output of approximately 35 Watts was applied to the surface of the cortex using a beam delivery system which approximated the beam profile after the laser light passes through the human skull. Peak power density measurements were taken through sections of human brain tissue using an Ocean Optics spectrophotometer Model USB 2000, Serial No. G1965 and beam diameter after scattering was approximated using a Sony Model DCR-IP220, Serial No. 132289.

A fresh human brain and spinal cord specimen (obtained within six hours after death) was collected and placed in physiologic Dakins solution. The pia layer, arachnoid layer, and vasculature were intact. The brain was sectioned in the midline sagittaly and the section was placed in a container and measurements taken at thicknesses of 4.0 centimeters (±0.5 centimeter), 2.5 centimeters (±0.3 centimeter), and 1.5 centimeters (±0.2 centimeter). The PD measurements are shown in Table 2:

TABLE 2

| Thickness | PD at cortex | Average PD at thickness |
|---|---|---|
| 4.0 cm | 20 $mW/cm^2$ | 4.9 $\mu W/cm^2$ |
| 2.5 cm | 20 $mW/cm^2$ | 20 $\mu W/cm^2$ |
| 1.5 cm | 10 $mW/cm^2$ | 148 $\mu W/cm^2$ |

Figure 43:
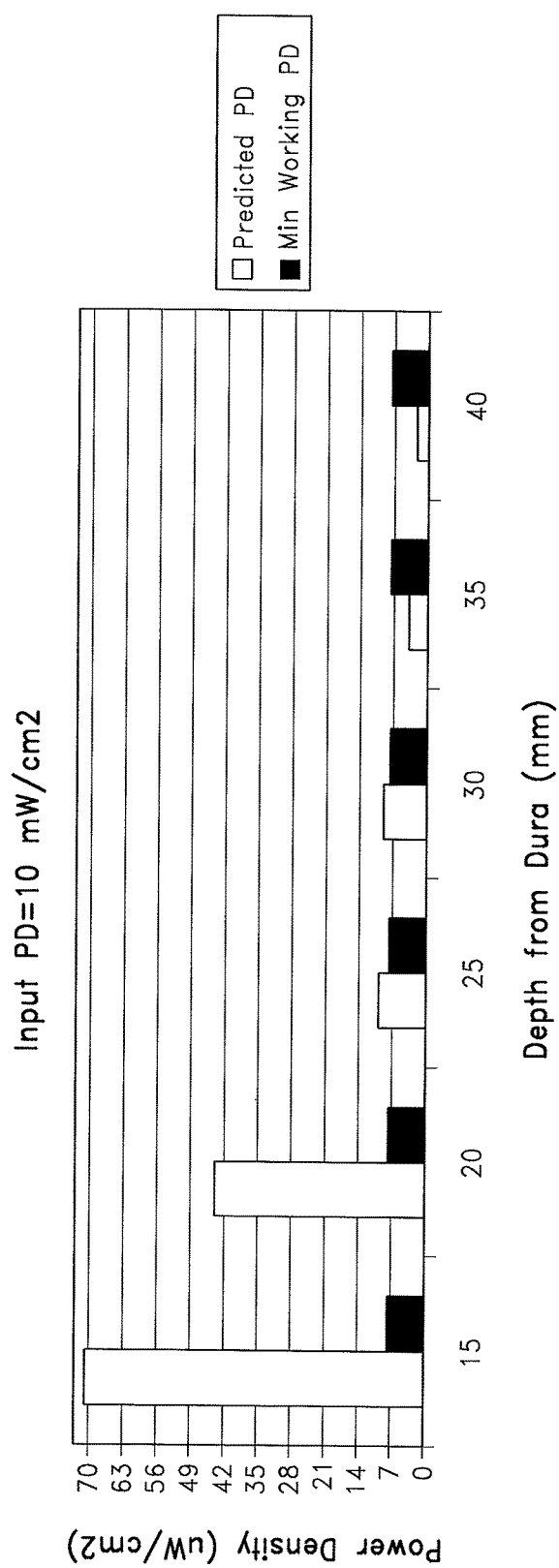
FIG. 43 is a graph of the PD versus the depth from the dura for an input PD of 10 mW/cm$^2$.

FIG. 43 is a graph of the PD versus the depth from the dura for an input PD of 10 $mW/cm^2$ with the light bars corresponding to predicted values of the PD and dark bars corresponding to an estimated minimum working PD of is 7.5 $\mu W/cm^2$, as described below.

Based upon prior animal experimentation, a conservative estimation of the minimum known PD within the tissue of the brain which is able to show efficacy in stroke animal models is 7.5 $\mu W/cm^2$. This estimated minimum working PD is drawn from an experiment in which 10 mW was applied to the rat brain surface, and 7.5 $\mu W/cm$ PD was directly measured 1.8 centimeters from the surface. This stroke model consistently produced significant efficacy, including for strokes 1.8 centimeters from the laser probe. Note that this 7.5 $\mu W/cm^2$ is a conservative estimate; the same power density at the brain surface also consistently produces significant efficacy in the 3 centimeter rabbit clot shower model. Note also that the power density measurements in the human brain experiment do not factor in the effect from the CNS-filled sulci, through which the laser energy should be readily transmitted. However, even conservatively assuming 7.5 $\mu W/cm^2$ as the minimum power density hurdle and ignoring expected transmission benefits from the sulci, the experiment described above confirms that approximately 10-15 $mW/cm^2$ transmitted upon the cortex (as per an example dosimetry in man) will be effective to at least 3.0 centimeters from the surface of the brain.

In Vivo Thermal Measurements

In vivo thermal measurements were made to determine the heating effect in living tissue of laser light having a wavelength of approximately 808 nanometers. A GaAlAs laser source of 808-nanometer light was placed in direct contact with the skin of the heads of live rabbits and rats. The laser source had an approximately Gaussian beam profile with a beam diameter of 2.5-4.0 millimeters ($1/e^2$). Thermocouple probes (Model Bat-12 from Physitemp Instruments Inc. of Clifton, N.J.) were placed in the subcutaneous tissue and below the dura and measurements were recorded at various power densities. The results of these measurements are shown in Table 3:

TABLE 3

| Animal | Probe location | Dose | Exposure time | Temperature increase |
|---|---|---|---|---|
| Rat | Subcutaneous | 15 $mW/cm^2$ | 4 minutes | approximately 3° C. |
| Rat | Subdural | 15 $mW/cm^2$ | 4 minutes | approximately 1° C. |
| Rat | Subcutaneous | 75 $mW/cm^2$ | 4 minutes | approximately 7° C. |
| Rat | Subdural | 75 $mW/cm^2$ | 4 minutes | approximately 7° C. |
| Rabbit | Subcutaneous | 7.5 $mW/cm^2$ | 5 minutes | less than 0.5° C. |
| Rabbit | Subdural | 7.5 $mW/cm^2$ | 5 minutes | less than 0.5° C. |
| Rabbit | Subcutaneous | 37.5 $mW/cm^2$ | 5 minutes | approximately 5.5° C. |
| Rabbit | Subdural | 37.5 $mW/cm^2$ | 5 minutes | less than 0.5° C. |

There is minimal heating (e.g., less than 0.5° C.) in the subdural region at four times the therapeutic energy density. The "heat sink" effect of living tissue that minimizes possible heating in the cortex is significantly larger in humans than in rats or rabbits, due to the larger heat sink and blood flow volume, which further limits the undesirable effects of heating in the region of stroke. Therefore, in certain embodiments described herein, a therapeutic dosage of energy is delivered to the area of a stroke without undesirable heating of the dura.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention.

What is claimed is:

1. An apparatus for irradiating at least a portion of a patient's brain with electromagnetic radiation to treat stroke, Parkinson's disease, Alzheimer's disease, or depression, the apparatus comprising:

a source of the electromagnetic radiation;

an output optical element comprising a rigid and substantially thermally conductive material, the output optical element comprising a first surface configured to face towards the patient's scalp and to be in thermal communication with the patient's scalp during treatment and a second surface configured to face away from the patient's scalp during treatment;

a cooler thermally coupled to the second surface of the output optical element to remove heat from the output optical element through the second surface; and a heat sink thermally coupled to the cooler, wherein the heat sink is positioned so that the electromagnetic radiation from the source propagates through the heat sink and through the output optical element.

2. The apparatus of claim 1, wherein the electromagnetic radiation has at least one wavelength in a range between about 780 nanometers and about 840 nanometers.

3. The apparatus of claim 1, wherein the rigid and substantially thermally conductive material comprises sapphire.

4. The apparatus of claim 1, wherein the apparatus is to actively cool an irradiated portion of the patient's scalp.

5. The apparatus of claim 1, further comprising an optical diffuser.

6. The apparatus of claim 5, wherein the output optical element comprises a lens and the optical diffuser.

7. The apparatus of claim 5, wherein the optical diffuser is optically coupled to the output optical element, and the electromagnetic radiation propagates through the optical diffuser prior to reaching the output optical element.

8. The apparatus of claim 1, wherein the cooler comprises a thermoelectric cooler.

9. The apparatus of claim 1, wherein the heat sink comprises a first portion and a second portion, the heat sink positioned so that the electromagnetic radiation is transmitted into the first portion, out of the second portion, and to the output optical element.

10. The apparatus of claim 9, wherein the heat sink further comprises a reflective inner surface between the first portion and the second portion, wherein the electromagnetic radiation propagates through a region bounded by the inner surface prior to reaching the output optical element.

11. The apparatus of claim 1, wherein the apparatus comprises at least one trigger switch, the trigger switch electrically coupled to the source, the trigger switch actuated by pressing the output optical element against a surface, the source responsive to the trigger switch by emitting light only when the trigger switch is actuated.

12. The apparatus of claim 1, wherein the apparatus is configured to be held in position by hand and sequentially moved to irradiate selected portions of the patient's body.

13. The apparatus of claim 1, wherein the output optical element is sufficiently thermally conductive to conduct heat from the patient's scalp at a sufficient rate to prevent, minimize, or reduce damage or discomfort to the patient from heating of the skin due to the irradiation.

14. An apparatus for irradiating at least a portion of a patient's brain with electromagnetic radiation to treat stroke, Parkinson's disease, Alzheimer's disease, or depression, the apparatus comprising:

a source of the electromagnetic radiation, the electromagnetic radiation having at least one wavelength in a range between about 780 nanometers and about 840 nanometers;

an output optical element comprising sapphire, the output optical element comprising a front surface configured to face towards the patient's scalp and to be in thermal communication with the patient's scalp during treatment and a back surface configured to face away from the patient's scalp during treatment;

a thermoelectric cooler thermally coupled to the back surface of the output optical element and configured to remove heat from the output optical element through the back surface and to actively cool an irradiated portion of the patient's scalp; and a heat sink thermally coupled to the thermoelectric cooler, wherein the heat sink is positioned so that the electromagnetic radiation from the source propagates through the heat sink and through the output optical element.

* * * * *

UNITED STATES PATENT AND TRADEMARK OFFICE
CERTIFICATE OF CORRECTION

PATENT NO. : 10,188,872 B2  
APPLICATION NO. : 12/496571  
DATED : January 29, 2019  
INVENTOR(S) : Luis De Taboada et al.

Page 1 of 1

It is certified that error appears in the above-identified patent and that said Letters Patent is hereby corrected as shown below:

In the Claims

In Column 47, Line 22, in Claim 4, Line 1, after "is" insert --configured--.

Signed and Sealed this  
Ninth Day of April, 2019

Andrei Iancu  
*Director of the United States Patent and Trademark Office*